(12) United States Patent
Locklin et al.

(10) Patent No.: US 12,319,828 B2
(45) Date of Patent: *Jun. 3, 2025

(54) SURFACES AND COATING COMPOSITIONS HAVING ANTIFOULING, ANTITHROMBOTIC, AND ANTIBACTERIAL PROPERTIES AND METHODS OF MAKING

(71) Applicant: University of Georgia Research Foundation, Inc., Athens, GA (US)

(72) Inventors: Jason J. Locklin, Bogart, GA (US); Qiaohong Liu, Athens, GA (US); Priyadarshini Singha, Athens, GA (US); Hitesh Handa, Athens, GA (US); Jitendra Pant, Athens, GA (US); Marcus J. Goudie, Athens, GA (US); Sean P. Hopkins, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 231 days.

This patent is subject to a terminal disclaimer.

(21) Appl. No.: 17/663,296

(22) Filed: May 13, 2022

(65) Prior Publication Data

US 2023/0053808 A1   Feb. 23, 2023

Related U.S. Application Data

(62) Division of application No. 16/757,701, filed as application No. PCT/US2018/056778 on Oct. 19, 2018, now Pat. No. 11,370,934.

(60) Provisional application No. 62/685,621, filed on Jun. 15, 2018, provisional application No. 62/617,418, filed on Jan. 15, 2018, provisional application No. 62/575,104, filed on Oct. 20, 2017.

(51) Int. Cl.
  *C09D 133/10* (2006.01)
  *A61K 31/197* (2006.01)
  *A61L 29/08* (2006.01)
  *A61L 29/16* (2006.01)

(52) U.S. Cl.
  CPC .......... *C09D 133/10* (2013.01); *A61K 31/197* (2013.01); *A61L 29/085* (2013.01); *A61L 29/16* (2013.01); *A61L 2300/21* (2013.01)

(58) Field of Classification Search
  CPC ........................... A61L 2300/114; A61L 29/08
  See application file for complete search history.

(56) References Cited

U.S. PATENT DOCUMENTS

| | | | |
|---|---|---|---|
| 7,384,490 B2 | 6/2008 | Nishikawa | |
| 10,323,132 B2 | 6/2019 | Ishihara et al. | |
| 2004/0073122 A1 | 4/2004 | Stofer et al. | |
| 2008/0286332 A1* | 11/2008 | Pacetti | A61P 9/10 623/1.42 |
| 2010/0145286 A1 | 6/2010 | Zhang et al. | |
| 2012/0059111 A1* | 3/2012 | Sandhu | C09D 133/062 526/263 |
| 2013/0261566 A1 | 10/2013 | Lockwood et al. | |
| 2015/0238662 A1 | 8/2015 | Handa et al. | |
| 2015/0366831 A1* | 12/2015 | Brisbois | A61K 31/197 424/484 |
| 2017/0028106 A1 | 2/2017 | Brisbois et al. | |
| 2018/0112405 A1 | 4/2018 | Kasprzak et al. | |
| 2019/0316054 A1 | 10/2019 | Ishihara et al. | |

FOREIGN PATENT DOCUMENTS

| | | |
|---|---|---|
| CN | 102325825 A | 1/2012 |
| WO | 2010/065960 A1 | 6/2010 |
| WO | 2015119678 A1 | 8/2015 |
| WO | 2016140259 A1 | 9/2016 |

OTHER PUBLICATIONS

Muir et al. ACS Appl Mater Interfaces, 2014, 6, 958-966.*
Pubchem: 2-methacrylo0yloxyethyl phosphorylcholine, 1 page.*
Smith et al., J Med Chem, 1996, 39, 1148-1156.*
Gierke et al., Sci Technol Adv Material, 12, 2011, 6 pgs.*
Brisbois et al, Biomaterials, 2013, 34, 2, 6957-6966.*
M.J. Goudie, E.J. Brisbois, J. Pant, A. Thompson, J.A. Potkay, H. Handa, Characterization of an S-nitroso-N-acetylpenicillamine-based nitric oxide releasing polymer from a translational perspective, Int. J. Polym. Mater. Polym. Biomater. 65(15) (2016) 769-778.
Y. Wo, Z. Li, E.J. Brisbois, A. Colletta, J. Wu, T.C. Major, C. Xi, R.H. Bartlett, A.J. Matzger, M.E. Meyerhoff, Origin of long-term storage stability and nitric oxide release behavior of carbosil polymer doped with S-nitroso-N-acetyl-D-penicillamine, ACS Appl. Mater. Interfaces 7(40) (2015) 22218-22227.
E.J. Brisbois, T.C. Major, M.J. Goudie, M.E. Meyerhoff, R.H. Bartlett, H. Handa, Attenuation of thrombosis and bacterial infection using dual function nitric oxide releasing central venous catheters in a 9day rabbit model, Acta Biomater. 44 (2016) 304-312.

(Continued)

*Primary Examiner* — Kyle A Purdy
(74) *Attorney, Agent, or Firm* — Thomas | Horstemeyer, LLP

(57) ABSTRACT

Coating compositions, coated articles including the coating compositions, and methods of making the coating compositions and coated articles are provided. In some aspects, the coating compositions are applied to a substrate having nitric oxide-releasing properties. The coating compositions can include copolymers having crosslinking agents that can be activated with mild UV light (about 345 nm to 365 nm) to avoid damaging the substrate while creating strong covalent bonds to the substrate. The copolymers can include hydrophilic repeat units, and in particular zwitterionic repeat units such as repeat units containing phosphorylcholine groups. In some aspects, the coating compositions are applied to a surface of a polymer substrate, wherein the polymer substrate had nitric oxide releasing properties. The coating compositions and the coated articles can have antifouling, antithrombotic, and/or antibacterial properties.

7 Claims, 25 Drawing Sheets

(56) References Cited

OTHER PUBLICATIONS

E.J. Brisbois, M. Kim, X. Wang, A. Mohammed, T.C. Major, J. Wu, J. Brownstein, C. Xi, H. Handa, R.H. Bartlett, Improved Hemocompatibility of Multi-Lumen Catheters via Nitric Oxide (NO) Release from S-Nitroso-N-acetylpenicillamine (SNAP) Composite Filled Lumen, ACS Appl. Mater. & Interfaces (2016).

Amoako Kagya A. et al: "Multimodal, Biomaterial-Focused Anticoagulation via Superlow Fouling Zwitterionic Functional Groups Coupled with Anti-Platelet Nitric Oxide Release", Advanced Materials Interfaces, vol. 3, No. 6, Mar. 1, 2016 (Mar. 1, 2016), p. 1500646.

Vasilis G Gavalas et al: "Enhancing the blood compatibility of ion-selective electrodes", Analytical and Bioanalytical Chemistry, Springer, Berlin, DE, vol. 384, No. 1, Jan. 1, 2006 (Jan. 1, 2006), pp. 65-72.

Marcus J. Goudie et al: "Liquid-infused nitric oxide-releasing (LINORel) silicone for decreased fouling, thrombosis, and infection of medical devices", Scientific Reports, vol. 7, No. 1, Jan. 1, 2017 (Jan. 1, 2017).

European Search Report for EP Application No. 18867545.8 mailed Jun. 7, 2021.

"Covalent Grafting of Antifouling Phosphorylcholine-Based Copolymers with Antimicrobial Nitric Oxide Releasing Polymers to Enhance Oct. 30, 2017 Infection-Resistant Properties of Medical Device Coatings", Liu et al. Langmuir 2017, 33, 13105-13113. DOI: 10.1021/acs.langmuir.7b02970.

International Search Report for PCT/US2018/056778 mailed Feb. 12, 2019.

Wo, Yaqi and Xu, Li-Chong and Li, Zi and Matzger, Adam J_ and Meyerhoff, Mark E. and Siedlecki, Christopher A., Antimicrobial nitric oxide releasing surfaces based on S-nitroso-N-acetylpenicillamine impregnated polymers combined With submicron-textured surface topography., Biomater. Sci., 2017 5(7), 1265-1278., The Royal Society of Chemistry.

EP office action for International Application No. 18 867 545.8-1109 mailed Jun. 29, 2023.

U.S. Appl. No. 16/757,701, US-2021-0198516-A1, Jul. 1, 2021.

* cited by examiner

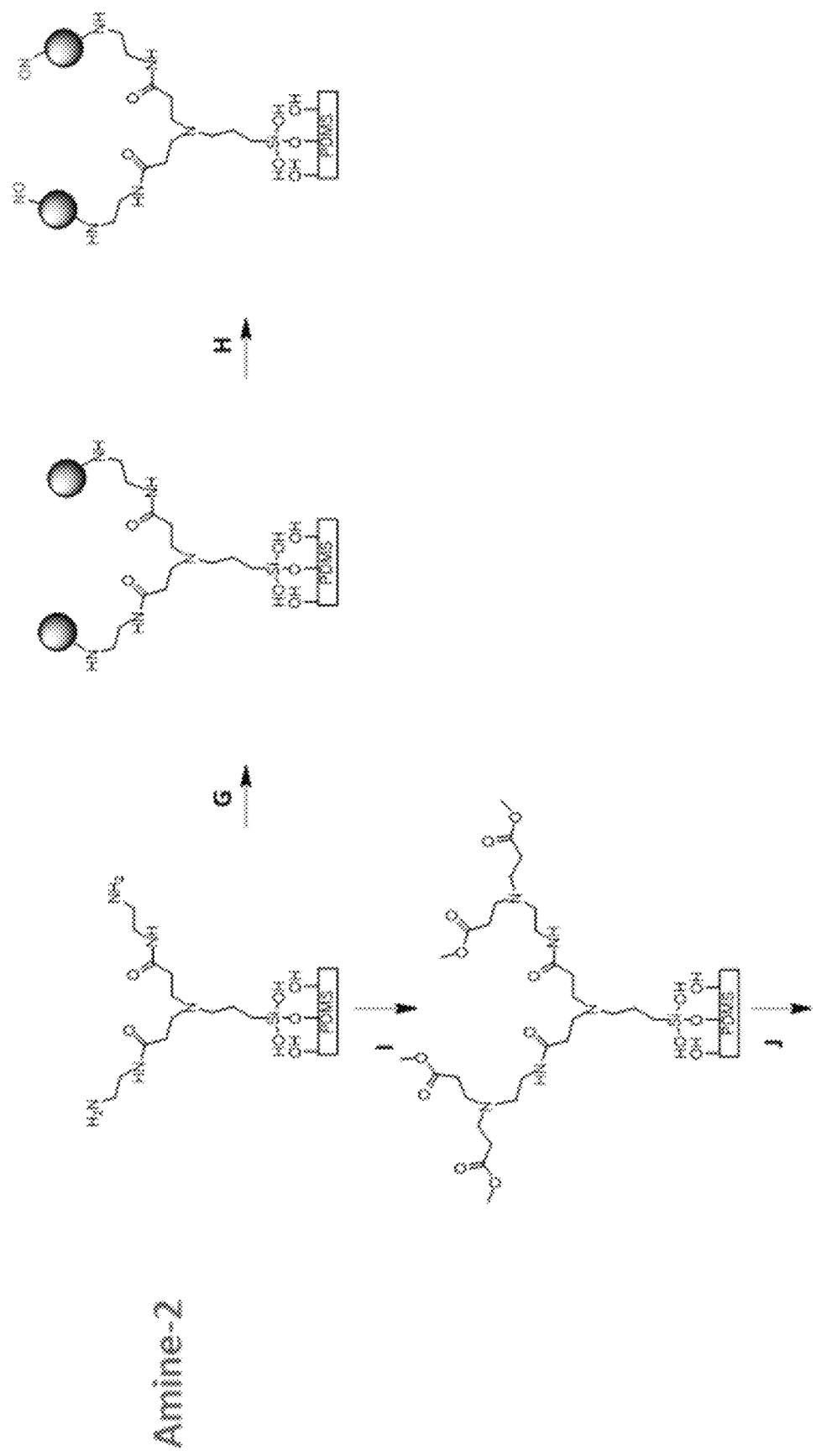
FIG. 16, continued

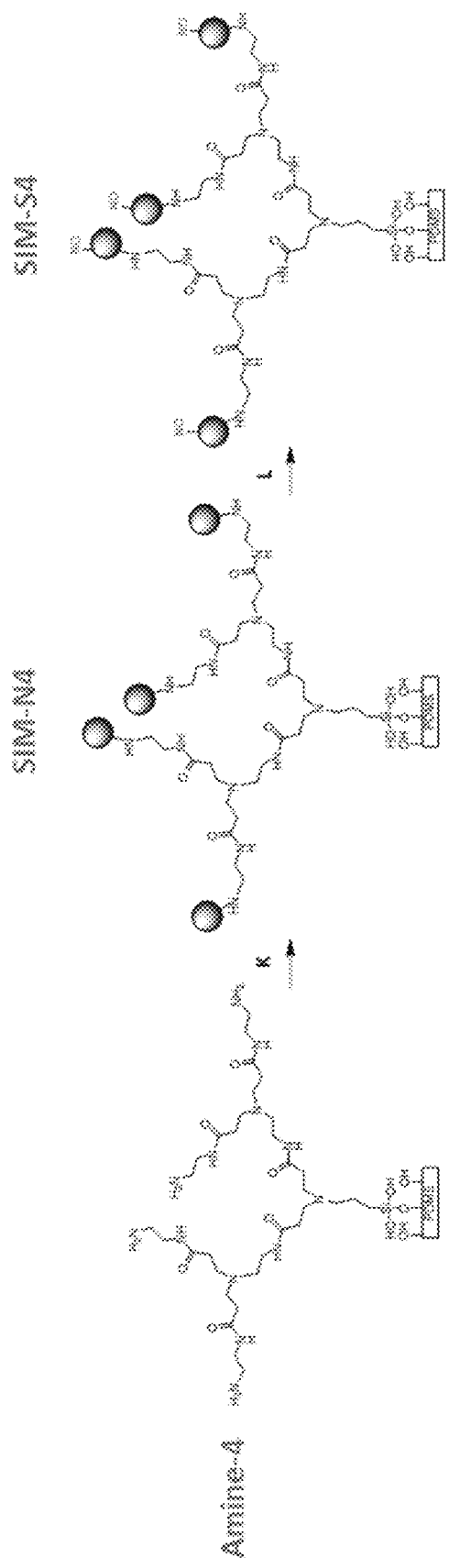
FIG. 16, continued

SURFACES AND COATING COMPOSITIONS HAVING ANTIFOULING, ANTITHROMBOTIC, AND ANTIBACTERIAL PROPERTIES AND METHODS OF MAKING

CROSS-REFERENCE TO RELATED APPLICATIONS

This application is a divisional application of U.S. non-provisional application Ser. No. 16/757,701, filed Apr. 20, 2020, which is a 35 U.S.C. § 371 national stage application of PCT application having serial number PCT/US2018/056778, filed on Oct. 19, 2018; which application also claims priority to, and the benefit of, U.S. provisional application entitled "SURFACES HAVING ANTIFOGGING AND ANTIFOULING CHARACTERISTICS, COATING COMPOSITIONS HAVING ANTIFOGGING AND ANTIFOULING CHARACTERISTICS, AND METHODS OF MAKING ANTIFOGGING AND ANTIFOULING SURFACES" having Ser. No. 62/617,418, filed Jan. 15, 2018; U.S. provisional application entitled "SURFACES AND COATING COMPOSITIONS HAVING ANTIFOULING CHARACTERISTICS, AND METHODS OF MAKING" having Ser. No. 62/575,104, filed Oct. 20, 2017; and U.S. provisional application entitled "SURFACES AND COATING COMPOSITIONS HAVING ANTIFOULING, ANTITHROMBOTIC, AND ANTIBACTERIAL PROPERTIES AND METHODS OF MAKING" having Ser. No. 62/685,621, filed Jun. 15, 2018, the contents of which are incorporated by reference in their entireties.

STATEMENT REGARDING FEDERALLY SPONSORED RESEARCH OR DEVELOPMENT

This invention was made with Government support under contracts K25HL111213, R01HL134899, and R01HL111213 awarded by the National Institutes of Health and contract 200-2016-91933 awarded by the Centers for Disease Control and Prevention. The Government has certain rights in the invention.

TECHNICAL FIELD

The present disclosure generally relates to coatings, coating compositions, coated articles, and methods of use and making thereof.

BACKGROUND

The non-specific adsorption of proteins has long been considered a grand challenge in many biomedical applications such as implants, contact lenses, catheters, and biosensors. In addition to medical device failure, the consequences of protein adsorption include thrombus formation, innate immune response, and bacterial infection. Preventing direct microbial contamination is also highly desired characteristic of medical devices, implants, and hospital equipment. Although significant progress has been made in understanding and reducing adsorption and contamination, the Centers for Disease Control and Prevention (CDC) still reported that, in 2011, there were an estimated 722,000 healthcare-associated infections (HAIs) in U.S. acute care hospitals. Additionally, about 75,000 patients with HAIs died during their hospitalization. On any given day, approximately 1 out of every 25 patients in the U.S. contracts at least one infection during their hospital care. Therefore, materials demonstrating antifouling and antimicrobial effects are highly desirable.

There remains a need for improved coating technologies, coating compositions, coatings, and coated articles that overcome the aforementioned deficiencies.

SUMMARY

In various aspects described herein, coating compositions, coated articles, and methods of making and using thereof are provided. In various aspects, the coated articles provide mechanisms for both active and passive antifouling, antimicrobial, and/or antithrombotic properties.

In some aspects, the coated articles include a nitric oxide-releasing substrate having at least one surface; and a zwitterionic polymer covalently attached to the at least one surface to form the coated article. The NO release can provide for prolonged active antifouling, antimicrobial, and/or antithrombotic properties. By presenting the zwitterionic groups on the surface, the coated articles are also capable of providing passive antifouling, antimicrobial, and/or antithrombotic properties that persist even once the NO release from the substrate has ceased.

In some aspects, the zwitterionic polymer is a copolymer comprising zwitterionic repeat units and tethering repeat units, and the tethering repeat units include covalent bonds to the at least one surface of the substrate. For instance, the zwitterionic polymer can be a random copolymer having a structure according to the following formula:

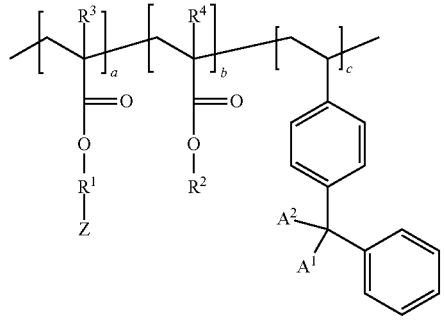

where each occurrence of Z is a zwitterionic moiety; where, in each instance, either (i) $A^1$ is none and $A^2$ is =O or (ii) $A^1$ is a covalent bond to the at least one surface of the substrate and $A^2$ is —OH; where each occurrence of $R^1$ is independently a covalent bond or a linear or branched, substituted or unsubstituted alkyl diradical having from 1 to 12 carbon atoms; where each occurrence of $R^2$, $R^3$, and $R^4$ is independently a linear or branched, substituted or unsubstituted alkyl having from 1 to 12 carbon atoms; and where a, b, and c are real number such that $0<a<1$, $0\le b<1$, $0<c<1$, and $a+b+c=1$.

Suitable nitric oxide-releasing substrates can include a polymer and nitric-oxide donor dispersed within the polymer; wherein the nitric-oxide donor is present in an amount from about 6 wt % to about 11 wt % based upon a total weight of the nitric oxide-releasing substrate. In some aspects, the substrates have surface hydrogens capable of forming covalent bonds to the tethering repeat units. The nitric-oxide donor dispersed in the polymer can be any suitable NO donor material such as an organic nitrate, a metal-NO complex, an N-nitrosamine, an S-nitrosothiol, or a combination thereof.

In some aspects, the coated articles include a substrate having nitric oxide-releasing groups covalently attached to the surface through branched alkylamine spacers. The alkylamine spacers can be covalently attached to the surface of the substrate such that the branched alkylamine spacer coupled to the surface of the polymer substrate provides passive antifouling, antithrombotic and antimicrobial properties, while the NO-donor moiety releases NO and provides active antimicrobial properties.

In various aspects, coating compositions including the polymers are provided as well as methods of making coated articles using the coating compositions. In particular, the polymers can include crosslinking agents that can be activated with mild UV light (about 345 nm to 365 nm) to avoid damaging the substrate while creating strong covalent bonds to the substrate. The methods can include applied the polymers to the surface using spin coating, spray coating, dip coating, pad application, or films with adhesive backing. The methods can include applying UV light to crosslink the polymers to the surface of the substrate.

Coated articles can include any article where antifouling, antithrombotic and antimicrobial properties are beneficial. In some aspects, the article can include a catheter (including, but not limited to, vascular and urinary catheters), a coronary stent, a wound dressing, extracorporeal circuits, membrane oxygenators, endotracheal tubes, a vascular graft, and the like.

Other systems, methods, features, and advantages of the coating compositions, coated articles, and methods of making thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 10A): UV-Vis Spectra of SNAP-BPAM film before and after UV irradiation (254 nm, 90 s). After UV irradiation for 90 seconds, absorbance at 255 nm decreased, indicating the completion of the crosslinking reaction. (FIG. 10B): Total SNAP content after UV irradiation was reported to be approximately 95.44±2.5% of the initial SNAP content. The data is reported as a mean±standard deviation for n=3 samples and the significance with a p-value<0.05 is stated for comparisons.

(FIG. 15A) S. aureus; (FIG. 15B) P. aeruginosa; (i) Control, (ii) SNAP, (iii) BPAM, and (iv) SNAP-BPAM. The bigger ZOI with SNAP-BPAM combination is due to increase in NO flux with BPAM topcoat.

DETAILED DESCRIPTION

Figure 1:
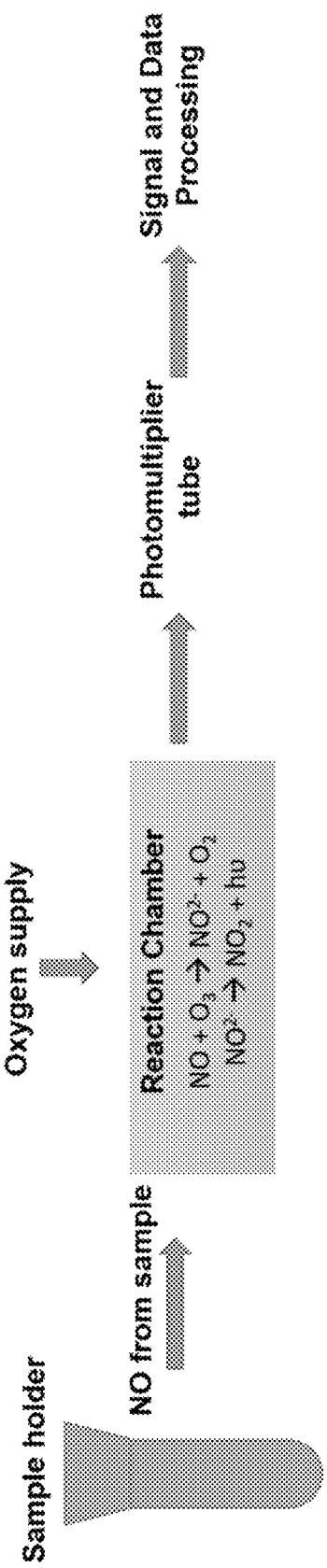
FIG. 1 shows nitric oxide chemiluminescence analyzer flowchart.

In various aspects, coating compositions, coated articles, and methods of making thereof are provided that overcome one or more of the aforementioned problems. In accordance with the purpose(s) of the present disclosure, as embodied and broadly described herein, embodiments of the present disclosure relate to coatings, substrates, and/or articles having antifouling and antimicrobial characteristics, methods of making the coatings, substrate, and/or articles, and methods of decreasing the amount of biochemical components and/or microorganisms formed on a surface of the substrate or article, and the like.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Abbreviations: BPMPC, 2-methacryloyloxyethyl phosphorylcholine-co-butyl methacrylate-co-benzophenone; N-(4-benzoylbenzyl)-N,N-dimethylbutan-1-ammonium iodide (BPAM); NO, nitric oxide; SNAP, S-nitroso-N-acetylpenicillamine; BP, 4-vinylbenzophenone; MPC, 2-Methacryloyloxyethyl phosphorylcholine; BSA, bovine serum albumin; FITC-BSA, fluorescein isothiocyanate labeled bovine serum albumin; NAP, N-acetyl-D-penicillamine; $NaNO_2$, sodium nitrite; conc. $H_2SO_4$, concentrated sulfuric acid; THF, tetrahydrofuran; $NaH_2PO_4$, sodium phosphate monobasic; LB, Luria broth; $Na_2HPO_4$, sodium phosphate dibasic; EDTA, ethylenediamine tetraacetic acid;

NaOH, sodium hydroxide; $KH_2PO_4$, potassium phosphate monobasic; CarboSil® 20 80A thermoplastic silicone-polycarbonate-urethane (hereafter will be referred to as CarboSil); DMAc, dimethylacetamide; NBS, N-Bromosuccinimide; AIBN, 2, 2'-azo-bis(2-methylpropionitrile); PBS, Phosphate buffered saline; ATCC, American Type Culture Collection.

The terms "anti-fouling" or "anti-foul" as used herein, applies to compositions, surfaces, or articles having characteristics preventing or minimizing the adhesion of biological materials (e.g., proteins), microorganisms, or other debris.

The terms "antimicrobial" and "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila, Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydia trachomatis, Chlamydia psittaci, Coxiella burnetii, Escherichia coli, Neisseria meningitidis, Neisseria gonorrhea, Haemophilus influenzae, Haemophilus ducreyi,* other Hemophilus species, *Yersinia pestis, Yersinia enterocolitica,* other *Yersinia* species, *Escherichia coli, E. hirae* and other *Escherichia* species, as well as other Enterobacteria, *Brucella abortus* and other *Brucella* species, *Burkholderia cepacia, Burkholderia pseudomallei, Francisella tularensis, Bacteroides fragilis, Fusobacterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae.*

The term "protozoan" as used herein includes, without limitations flagellates (e.g., *Giardia lamblia*), amoeboids (e.g., *Entamoeba histolytica*), and sporozoans (e.g., *Plasmodium knowlesi*) as well as ciliates (e.g., *B. coli*). Protozoan can include, but it is not limited to, *Entamoeba coli, Entamoeba histolytica, Iodamoeba buetschlii, Chilomastix mesnili, Trichomonas vaginalis, Pentatrichomonas homini, Plasmodium vivax, Leishmania braziliensis, Trypanosoma cruzi, Trypanosoma brucei,* and Myxosporidia.

The term "algae" as used herein includes, without limitations microalgae and filamentous algae such as *Anacystis nidulans, Scenedesmus* sp., *Chlamydomonas* sp., *Chlorella* sp., *Dunaliella* sp., *Euglena* sp., *Prymnesium* sp., *Porphyridium* sp., *Synechococcus* sp., *Botryococcus braunii, Crypthecodinium cohnii, Cylindrotheca* sp., *Microcystis* sp., *Isochrysis* sp., *Monallanthus salina, M. minutum, Nannochloris* sp., *Nannochloropsis* sp., *Neochloris oleoabundans, Nitzschia* sp., *Phaeodactylum tricornutum, Schizochytrium* sp., *Scenedesmus obliquus,* and *Tetraselmis sueica* as well as algae belonging to any of Spirogyra, Cladophora, Vaucheria, Pithophora and Enteromorpha genera.

The term "fungi" as used herein includes, without limitations, a plurality of organisms such as molds, mildews and rusts and include species in the *Penicillium, Aspergillus, Acremonium, Cladosporium, Fusarium, Mucor, Neurospora, Rhizopus, Trichophyton, Botryotinia, Phytophthora, Ophiostoma, Magnaporthe, Stachybotrys* and *Uredinales* genera.

The terms "broad-spectrum biocide", "biocide", and "biocidal" as used herein include, without limitation, pesticides (e.g. fungicides, herbicides, insecticides, algicides, molluscicides, miticides, and rodenticides) and antimicrobials and may also include germicides, antibiotics, antibacterials, antivirals, antifungals, antiprotozoals, and antiparasites.

The term "antimicrobial effective amount" as used herein refers to that amount of the compound being administered/released which will kill microorganisms or inhibit growth and/or reproduction thereof to some extent (e.g. from about 5% to about 100%). In reference to the compositions or articles of the disclosure, an antimicrobial effective amount refers to that amount which has the effect of diminishment of the presence of existing microorganisms, stabilization (e.g., not increasing) of the number of microorganisms present, preventing the presence of additional microorganisms, delaying or slowing of the reproduction of microorganisms, and combinations thereof. Similarly, the term "antibacterial effective amount" refers to that amount of a compound being administered/released that will kill bacterial organisms or inhibit growth and/or reproduction thereof to some extent (e.g., from about 5% to about 100%). In reference to the compositions or articles of the disclosure, an antibacterial effective amount refers to that amount which has the effect of diminishment of the presence of existing bacteria, stabilization (e.g., not increasing) of the number of bacteria present, preventing the presence of additional bacteria, delaying or slowing of the reproduction of bacteria, and combinations thereof.

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

NO, nitric oxide; SNAP, S-nitroso-N-acetylpenicillamine; GSNO, S-nitroso-glutathione; PVA, polyvinyl alcohol; SIM, Surface immobilized Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

Coating Compositions

The present disclosure includes a coating comprising a NO-donor substrate and a polymer. In an aspect, the polymer includes a hydrophilic moiety and a photo cross-linkable moiety, where the coating has one or both of anti-fouling and antimicrobial characteristics. In an aspect, the hydrophilic moiety is covalently attached to the surface of the NO-donor substrate through a photo cross-linkable moiety upon exposure to light energy (e.g., ultraviolet energy), which can form a coating (e.g., about 10 to 500 nm thick) on the surface. Advantageously, the NO-donor substrate has antimicrobial properties, and the photo cross-linkable moiety has antifouling characteristics. The attachment of the photo cross-linkable moiety to the NO-donor substrate is a one step process which is simple and scalable.

In an embodiment, the photo cross-linkable moiety can include an aryl ketone (about 340 to 400 nm), an aryl azide group (about 250 to 450 nm or about 350 to 375 nm), a diazirine group (about 340 to 375 nm), and the polymer can include a combination of these groups. In an embodiment, the photo cross-linkable moiety can include alkyl-arylketones and diarylketones bearing at least one condensed ring system substituent such as naphthyl and anthracenyl. In an embodiment, the aryl ketone group can include benzophenone (about 340 to 380 nm), acetophenone (about 340 to 400 nm), a naphthylmethylketone (about 320 to 380 nm), a dinaphthylketone (about 310 to 380 nm), a dinaphtylketone derivative (about 320 to 420 nm), or derivatives of each of these. In an embodiment, the photo cross-linkable moiety is a benzophenone group. In an embodiment, the aryl azide group can include phenyl azide, alkyl substituted phenyl azide, halogen substituted phenyl azide, or derivatives of each of these. In an embodiment, the diazirine group can include 3,3 dialkyl diazirine (e.g., 3,3 dimethyl diazirine, 3, 3 diethyl diazirine), 3,3 diaryl diazirine (e.g., 3,3 diphenyl diazirine), 3-alkyl 3-aryl diazirine, (e.g., 3-methyl-3-phenyl diazirine), or derivatives of each of these.

Embodiments of the present disclosure include a coating as above, where the photo cross-linkable moiety can be benzophenone. Hydrophilic polymers can be used as coating materials for the preparation of superhydrophilic surfaces. The ability of an aryl ketone moiety such as benzophenone (BP) to act as a cross-linking agent and abstract hydrogen from a suitable hydrogen donor has been well studied and utilized in various chemical systems for many years. 5-7 BP can be used for crosslinking organic thin films and it can be activated using mild UV light (345-365 nm), avoiding oxidative damage of the polymer and surface that can occur upon exposure to higher energy UV. The benzophenone moiety is more chemically robust than other organic cross-linkers and reacts preferentially with C—H bonds in a wide range of different chemical environments. Triggered by UV light, benzophenone undergoes an n-pi* transition, resulting in the formation of a biradical triplet excited state that can abstract a hydrogen atom from a neighboring aliphatic C—H group to form a new C—C bond. This triplet state also has especially high reactivity for H located alpha to electron donating heteroatoms (nitrogen and oxygen). This photoreaction has recently been used to attach thin polymer layers to metal and oxide surfaces, 8-11 along with applications in microfluidics, 12 organic semiconductors, 13 and biosensors. 14 (the references for this paragraph correspond to Example 1)

In an embodiment, the hydrophilic moiety functions to provide at least a hydrophilic characteristic to the coating. Embodiments of the present disclosure include a surface as above, where the hydrophilic moiety can be a C1-C4-alkyl methacrylate such as iso-butyl methacrylate or alkyl acrylate.

In an embodiment the hydrophilic moiety can be a zwitterionic polymer (or ethylene glycol polymer, or hydroxyfunctional acrylates polymer). In various embodiments, the zwitterionic polymer can be 2-methacryloyloxyethyl phosphorylcholine-co-butyl methacrylate-co-benzophenone (BPMPC) (or any sulfobetaine methacrylate, carboxybetaine methacrylate-co-butyl methacrylate-co-benzophenone copolymers). The BPMPC can be from about 20% to about 99% 2-methacryloyloxyethyl phosphorylcholine (MPC), (e.g. 30% MPC, 50% MPC, 70% MPC, or 90% MPC). Advantageously, the BPMPC coating has excellent hydrophilicity, which helps inhibit the adsorption of proteins from solution when the coating is applied to an article. In various embodiments, the BPMPC coating is from about 20 nm to about 1 μm.

In an embodiment the polymer can be represented by one or more of the following polymers:

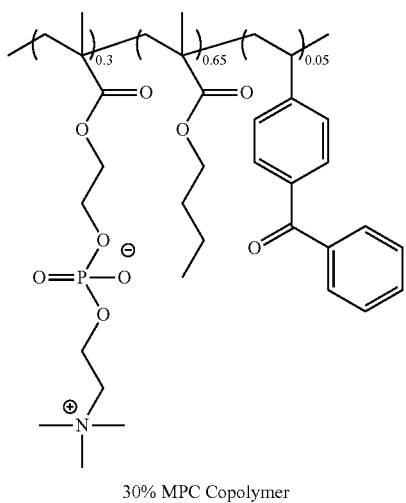

30% MPC Copolymer

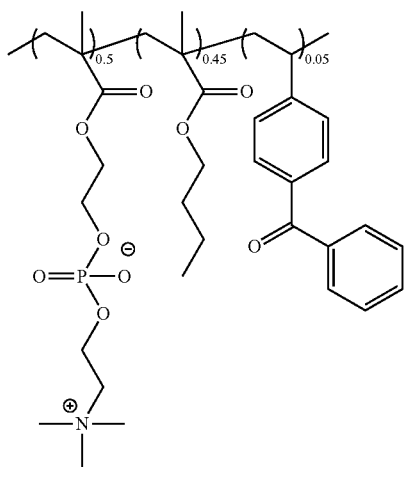

50% MPC Copolymer

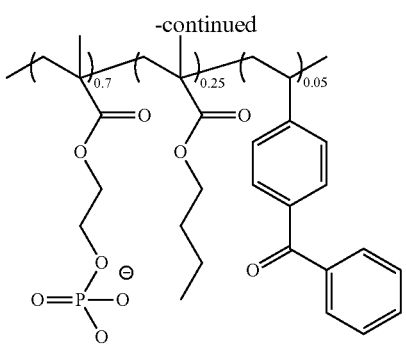

70% MPC Copolymer

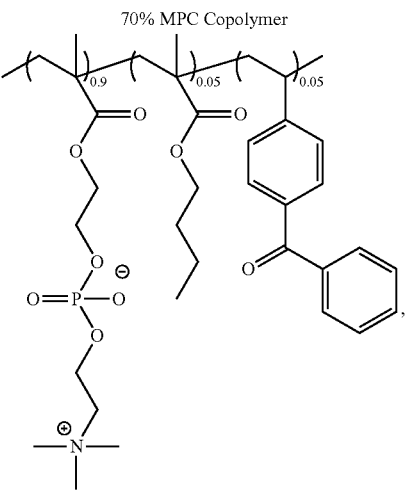

90% MPC Copolymer where the ratio of the components can vary from those described above, where each subscript can vary from 0.05 to 0.9.

Substrates

In an aspect, the NO-donor substrate releases NO. Embodiments of the present disclosure include a coating as above, where the NO-donor substrate includes an organic nitrate, a metal-NO complex, an N-nitrosamine, an S-nitrosothiol, or a combination thereof. In various embodiments, NO-donor substrate can be a polymer film doped with S-nitroso-N-acetylpenicillamine (SNAP). Embodiments of the present disclosure include a coating as above, where the NO-donor substrate has about 6%-11% wt S-nitroso-N-acetylpenicillamine (SNAP). In various embodiments, the polymer film can be silicone-polycarbonate-urethane thermoplastic (CarboSil).

Advantageously, the NO-donor substrate releases NO at a higher, more sustained rate when coated with the BPMPC than when used alone. Another advantage to the coating is the reduced leaching of SNAP over CarboSil alone.

Embodiments of the present disclosure include a coating as above, wherein the NO-donor substrate is covalently linked to the photo cross-linkable moiety upon exposure to light energy. In an embodiment, the photo cross-linkable moiety and the NO-donor substrate of coating are covalently bonded via the interaction of a UV light (e.g., about 340 to 370 nm) that causes a C—C bond to form between the NO-donor substrate and the photo cross-linkable moiety.

Embodiments of the present disclosure include a coating as above, wherein the doped polymer film is coated in additional layers of polymer film. In various embodiments, the doped polymer film can be coated with one or more layers of film. The coating can be from about 20 nm to about 1 μm thick.

The present disclosure also includes substrate having a surface, including a coating comprising an NO-donor substrate and a photo cross-linkable moiety. The NO-donor substrate is covalently attached to the photo cross-linkable moiety to form a film applied to the surface. Advantageously, the coating gives the surface one or both of an anti-fouling and an antimicrobial characteristic.

Although NO-donor substrates provide an active mechanism of antimicrobial action, once the NO-releasing properties of a substrate/coating/material have been exhausted, it may no longer provide antifouling/anti-microbial activity. Thus, the present disclosure provides polymer substrate surfaces, coatings, and articles having both active and passive antifouling, antimicrobial, and antithrombotic properties. The present disclosure provides polymer materials and/or coatings that provide a branched polymer surface chemistry to provide hydrophobic and steric hindrances to adhesion by proteins, bacteria and other microbes, while simultaneously providing active antifouling and antimicrobial activity from surface immobilized NO-donors.

In embodiments, the present disclosure provides a polymer material and/or substrate having a surface-immobilized (SIM) NO-donor functionalized surface. The SIM NO-donor functionalized surface includes a branched alkylamine spacer coupled to the surface of the polymer substrate to provide passive antifouling, antithrombotic and antimicrobial properties. The SIM NO-donor functionalized surface also includes an NO-donor moiety coupled to the branched alkyl spacer such that the NO-donor moiety releases NO and provides active antimicrobial properties. In embodiments, the polymer material having the SIM NO-donor functionalized surface retains antifouling, antithrombotic and anti-microbial properties after all of the NO has been released.

In embodiments polymer substrate/polymer material can include polymers such as, but not limited to polyurethane, silicone, polyvinyl chloride, ketone polymers (including, but not limited to, polyether ether ketone), polyethylene (including, but not limited to, ethylene vinyl acetate), bioresorbable polymers (including, but not limited to, polylactic acid, polyglycolic acid, and polycaprolactone), fluoropolymers (including, but not limited to, polytetrafluoroethylene, perfluoroether, and fluorinated ethylene propylene), and combinations thereof. In embodiments, the polymer substrate includes polymer materials typically used in the making of medical devices. In embodiments, the polymer substrate is or forms part of a medical device.

In embodiments, the branched alkylamine spacers have multiple branches. The branching steps, described below, can add 1-4 branches to the spacers. Thus, multiple branches are possible, and embodiments of the present disclosure are intended to encompass various branching densities.

In embodiments, the NO-donor is biocompatible. In embodiments the NO-donor includes biocompatible NO-donors such as, but not limited to, N-nitrosoamine, S-nitrosothiol, diazeniumdiolate, or a combination thereof. In embodiments a combination of NO-donors can be used. For instance, in embodiments, nitrosothiols and diazeniumdiolates can be used in conjunction by having secondary amines in the backbone, with attachment of a nitrosothiol to the end functional group. In embodiments, the NO-donor is S-nitroso-N-acetylpenicillamine (SNAP), S-nitroso-glutathione, S-nitroso-N-acetylcysteine, among others. In some embodiments the polymer substrate also includes a silicone oil impregnated into the polymer substrate. In embodiments, the silicon oil is impregnated into the polymer substrate after formation of the SIM NO-donor functionalized surface.

Embodiments of the present disclosure also include medical devices including the polymer substrate of the present disclosure. Such medical devices include implantable devices or other medical equipment. In some embodiments, the implantable medical device can include, but is not limited to a catheter (including, but not limited to, vascular and urinary catheters) a coronary stent, a wound dressing, extracorporeal circuits, membrane oxygenators, endotracheal tubes, a vascular graft, and the like.

The present disclosure also includes articles having a surface with a coating composition, where the coating composition includes a branched alkylamine spacer coupled to the surface of the polymer substrate and an SIM NO-donor moiety coupled to the alkyl spacer to form an SIM branched NO-donor coating. With such coatings, the NO-donor moiety releases NO, providing the surface with antifouling, antithrombotic, and antimicrobial properties as well as the properties provided by the branched polymer spacer described above. In embodiments, the article is a medical implant, medical device, or medical equipment. In embodiments, the article is further impregnated with silicone oil, which increases the hydrophobicity of the surface, further increasing the antifouling, anti-thrombotic, and anti-microbial properties. In embodiments, the NO-donor can include, but is not limited to, an N-nitrosoamine, an S-nitrosothiol, a diazeniumdiolate, or a combination thereof. In embodiments, the NO-donor is S-nitroso-Nacetylpenicillamine (SNAP).

The present disclosure also provides methods of making the coatings/surfaces of the present disclosure. In embodiments the polymer material/substrate/surface can be but is not limited to, polyurethane, silicone, polyvinyl chloride, and combinations thereof. Embodiments of methods of making a SIM NO-donor functionalized coating on a polymer substrate surface include the following general steps. First, the polymer surface is amine-functionalized. In embodiments, amine-functionalization is preceded by functionalizing the polymer surface with hydroxyl groups to provide a hydroxyl-functionalized polymer surface to assist in amine functionalization.

In embodiments the polymer material includes silicone or the polymer has a silicone coating, or the polymer substrate is a silicone film/coating. In embodiments a silicone polymer surface can be hydroxyl functionalized by contacting or submerging the silicone surface with a mixture of HCl and hydrogen dioxide in water. In embodiments, the hydroxyl-functionalized polymer surface is then functionalized with amine groups to provide an amine-functionalized polymer surface. In embodiments, amine-functionalization includes contacting the hydroxylfunctionalized surface with APTMES to provide the amine-functionalized surface. Alternatives for imparting hydroxyl groups on the surface include, but are not limited to, treatment with air or oxygen plasma. Application of the silane can be done in solution as mentioned above or through vapor deposition (incubating the sample where the silane is vaporized rather than liquid form).

After providing an amine-functionalized polymer surface, in embodiments, the primary amines on the amine-functionalized surface are reacted with an alkyl acrylate to form branched alkyl spacers to provide a branched surface. In embodiments, this can include incubating the amine-functionalized surface in methanol:methyl acrylate to form branched alkyl spacers immobilized to the polymer surface. After branching, the branched alkyl spacers can be functionalized with amines or alkyl amines to provide an amine functionalized branched polymer surface. In embodiments, this can include incubating the branched surface in methanol:ethylenediamine to form amine functionalized branched alkyl spacers immobilized to the polymer surface. In embodiments, the branching and amine functionalization of the branched spacers is repeated to increase the branching of the spacers. It can be repeated as needed to achieve a desired branching density. In embodiments, the selection of alkyl acrylate and the selection of amine/alkyl amine can control the degree of branching. For example, the use of pentane-1,3,5 triamine rather than ethylenediamine can be used to provide an additional free primary amine after the methacrylate step. This would then change the branching sequence from 1-2-4, to 1-4-8. Thus, each branching step can add multiple branches and can be repeated (e.g., methacrylate or ethylenediamine) to add more branches, as desired. In embodiments, each branching step can add 1-4 branches (1 branch being a bifunctional molecule).

The NO-donor is then coupled to the immobilized, branched, amine-functionalized alkyl spacers. In embodiments, after providing immobilized, branched, amine-functionalized, alkyl spacers, the amine functionalized branched alkyl spacers are reacted with an NO-donor precursor to immobilize the NO-donor precursor to the polymer surface followed by nitrosating the NO-donor precursor. In embodiments, the amine functionalized branched polymer surface can be contacted with NAP-thiolactone (a NO-donor precursor), where ring opening of thiolactone allows binding of the free amines to immobilize NAP to the branched polymer surface. Nitrosating the NO-donor precursor converts the precursor into an active NO-donor and thus provides the surface-immobilized NO-donor functionalized coating on the polymer surface. In embodiments, the NO-donor precursor is NAP, and nitrosation of the immobilized NAP includes incubating the surface in neat tert-Butyl nitrate. The nitrosation step produces a surface-immobilized SNAP functionalized branched polymer coating on the polymer surface.

Coated Articles and Methods of Making Thereof

The present disclosure includes articles having a surface that has one or both of antifouling and antimicrobial characteristics. The antifouling and antimicrobial characteristics are the result of applying a coating on the surface of the article. As used herein, the one or both of antifouling and antimicrobial characteristics of the coating prevent or substantially reduce (e.g., about 80-99%, about 85 to 99%, about 90 to 99%, about 95 to 99.9%) biochemical (e.g., protein) and bacterial accumulation on a surface relative to the surface without these antifouling and antimicrobial characteristics. Advantageously, the coating can be applied to surfaces that can be hydrophilic or hydrophobic.

In an embodiment, the substrate or article (or the coating disposed on a surface of the article) may have an antimicrobial characteristic (e.g., kills at least 70%, at least 80%, at least 90%, at least 95%, or at least 99% of the microorganisms (e.g., bacteria) on the surface and/or reduces the amount of microorganisms that form or grow on the surface by at least 70%, at least 80%, at least 90%, at least 95%, or at least 99%, as compared to a similar surface without the coating disposed on the surface). In an embodiment, the substrate or article (or the coating disposed on a surface of the article) may have an anti-fouling characteristic (e.g. reduces the amount of biochemical (e.g., proteins), microorganisms, or debris that form or grow on the surface by at least 70%, at least 80%, at least 90%, at least 95%, or at least 99%, as compared to a similar surface without the coating disposed on the surface).

In various embodiments, the articles can have surfaces including those that may be exposed to microorganisms and/or that microorganisms might typically grow on such as, without limitation, medical instruments, medical implants, prosthetic devices, contact lenses, plastic devices, circuitry, fabrics, cooking counters, food processing facilities, kitchen utensils, food packaging, packaging materials (e.g., food, meat, poultry, and the like food packaging materials), plastic structures (e.g., made of a polymer or a polymer blend), glass or glass like structures having a functionalized layer (e.g., includes a C—H group) on the surface of the structure, metals, metal alloys, or metal oxides structure having a functionalized layer (e.g., includes a C—H group) on the surface of the structure, a structure (e.g., tile, stone, ceramic, marble, granite, or the like) having a functionalized layer (e.g., includes a C—H group) on the surface of the structure, and a combination thereof, textiles, filters, marine vessels, swimming pools, metals, drug vials, yarns, fibers, gloves, furniture, toys, diapers, leather, tiles, and flooring materials.

Embodiments of the present disclosure include articles or substrates as above, where the coating is applied to the surface using e.g. spin coating, spray coating, dip coating, pad application, films with adhesive backing, and the like.

The present disclosure also includes methods of making the substrate by exposing a NO-donor substrate to a polymer including a hydrophilic moiety and a photo cross-linkable moiety, and exposing the polymer to light energy, thereby causing the photo cross-linkable moiety to covalently attach to the NO-donor substrate and form the coating on the NO-donor substrate The present disclosure also includes methods of making a coating, including doping a polymer film with S-nitroso-N-acetylpenicillamine to form a NO-donor substrate, combining the NO-donor substrate with a polymer to form the coating, and exposing the coating to light energy, thereby causing the photo cross-linkable moiety to covalently attach to the NO-donor substrate.

Embodiments of the present disclosure include methods as above, wherein the doped polymer film can be coated in additional layers of polymer film. In various embodiments, the doped polymer film can be coated with one or more layers of film. The coating can be from about 20 nm to about 1 μm thick.

Nitric oxide (NO) is an endogenous, gaseous, free radical that is produced naturally by macrophages and by endothelial cells lining the vascular walls, and is involved in various biological processes, such as preventing platelet activation and adhesion, while also being a potent, broad spectrum bactericidal agent. To take advantage of these properties, NO-donors (e.g. s-nitrosothiols or diazeniumdiolates) have been developed to allow for the storage and localized delivery of NO, and are particularly advantageous for polymeric materials typically used for medical devices, such as polyurethanes, silicones, or polyvinyl chloride. The addition of these donors at various levels also provides a simple method for controlling the level of NO that is delivered from the materials.[15] Materials releasing NO have been shown to significantly reduce thrombus formation in both extracorporeal-circuit and vascular catheter models, and have been shown to provide significant reductions in bacteria during long term catheterization.[2,16]

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

To explore the covalent grafting of zwitterionic polymers to various substrates ranging from hydrophilic to hydrophobic, the benzophenone (BP) chromophore, a photoactive tethering reagent, was incorporated into the polymeric backbone.[19-24] The BP group can produce a diradical under low-intensity UV irradiation (350-365 nm) that abstracts an aliphatic hydrogen from a neighboring C—H bond to form a new C—C bond, without intensive UV oxidative damage to the polymer or substrates.[20] Through this process, network polymer films can be grafted with excellent durability to a broad selection of C—H containing materials and surfaces, and has been used for many applications such as microfluidics,[25-26] organic semiconductors,[27] redox polymers,[28-29] anti-icing polymers,[30] and biosensors.[31-32]

In an example of the present disclosure, zwitterionic terpolymers (2-methacryloyloxyethyl phosphorylcholine-co-butyl methacrylate-co-benzophenone, BPMPC) were synthesized that can be covalently grafted to antimicrobial, NO-releasing CarboSil (silicone-polycarbonate-urethane thermoplastic) upon UV-irradiation. The polymer-coated surfaces are characterized in detail and the zwitterionic stability is assessed under physiological conditions. The protein repellency properties of these coatings are evaluated. At the same time, no SNAP degradation was observed during coating or UV irradiation, and the release profile remained above the physiological level for 2 weeks with the zwitterionic top-coat. Moreover, enhanced antimicrobial activity was demonstrated with bacteria testing.

Experiment Section

Materials 4-vinylbenzophenone (BP) was synthesized according to a previously reported method.[30] 2-Methacryloyloxyethyl phosphorylcholine (MPC), albumin from bovine serum (BSA), fluorescein isothiocyanate labeled bovine serum albumin (FTIC-BSA), N-acetyl-D-penicillamine (NAP), sodium nitrite ($NaNO_2$), concentrated sulfuric acid (conc. $H_2SO_4$), tetrahydrofuran (THF), sodium phosphate monobasic ($NaH_2PO_4$), sodium phosphate dibasic ($Na_2HPO_4$), potassium chloride, sodium chloride, and ethylenediamine tetraacetic acid (EDTA) were purchased from Sigma Aldrich (St. Louis, MO). 2,2'-azobis(2-methylpropionitrile) (AIBN) and n-butyl methacrylate (BMA) were bought from Alfa-Aesar (Haverhill, MA). Isobutyltrichlorosilane was purchased from Tokyo Chemical Industry (Portland, OR). Concentrated hydrochloric acid (conc. HCl), sodium hydroxide (NaOH), and methanol were bought from Fisher-Scientific (Hampton, NH). Potassium phosphate monobasic ($KH_2PO_4$) and lysozyme from egg white were purchased from BDH Chemicals—VWR International (West Chester, PA). Carbo-Sil™ 20 80A UR STPU (referred to as CarboSil hereon) was acquired from DSM Biomedical Inc. (Berkeley, CA). Milli-Q filter was used to obtain deionized (DI) water for all the aqueous solution preparations. Nitrogen and oxygen gas cylinders were purchased from Airgas (Kennesaw, GA). *Staphylococcus aureus* (ATCC 6538, *S. aureus*) was used for the bacterial experiments. LB Agar (LA), Miller and Luria broth (LB), Lennox were purchased from Fischer BioReagents (Fair Lawn, NJ). All the chemicals were used without further purification.

In brief, CarboSil polymers with 10 wt % SNAP (test samples) and no SNAP content (control samples) were prepared using solvent evaporation and/or spin coating method. These samples were then coated with a zwitterionic copolymer (referred to as BPMPC) which was covalently bonded to the CarboSil base polymers by UV-crosslinking. Surface analysis was performed on the films pre- and post-UV radiation to understand the crosslinking behavior of the polyzwitterionic system. Test and control samples with the BPMPC coating were analyzed for their NO release behavior. The samples were then tested for protein adhesion for 14 days in physiological conditions (37° C. in PBS) to evaluate antifouling properties of the topcoat. Finally, antimicrobial assay of the samples was done using a modified version of ASTM E2180 protocol.

Synthesis of NO Donor, SNAP

S-nitroso-N-acetylpenicillamine was synthesized using a revised approach for a method previously reported.[38] 1M $H_2SO_4$ and 1M HCl were mixed with an equimolar amount of NAP, methanol and $NaNO_2$ aqueous solution. This reaction mixture was stirred for 20 minutes and then cooled for 7 hours with a constant flow of air on the mixture. After evaporation of the unreacted portion of the reaction mixture, precipitated green crystals of SNAP were filtered, collected and dried in a covered vacuum desiccator. Dried crystals of SNAP were used for all experiments.

Synthesis of CarboSil Films Doped with SNAP

CarboSil films containing 10 wt % SNAP were prepared using solvent evaporation method. 700 mg of CarboSil was dissolved in 10 mL of THF to make the polymer solutions. 77 mg of SNAP was added to this solution for a final concentration of 10 wt % of SNAP. This polymer-SNAP blend was stirred in dark conditions until the SNAP crystals dissolved completely. The blend was then transferred into Teflon molds and allowed to let the solvent evaporate overnight in fume hood. The overnight dried films were then cut into circular shapes of 0.8 cm diameter each. Each sample was immersed into a CarboSil solution without SNAP (40 mg $mL^{-1}$ of polymer concentration in THF) to coat it (this was repeated thrice for each sample). The samples were dried overnight and then dried under vacuum for an additional 24 hours. This added drying time was included to eliminate any remaining THF which can affect any following studies. Weight of each film was recorded before the topcoat application for all SNAP leaching behavior tests. The formulated samples were stored in the freezer (−18° C.) in the dark between experiments to prevent escape of SNAP or consequent loss of NO. These SNAP-incorporated films were used for NO release, SNAP leaching and bacterial cell viability analyses. All samples used for the tests were less than a week old to ensure integrity of studies.

Synthesis of Zwitterionic Copolymer (BPMPC)

The polymer was synthesized by free radical polymerization. MPC (0.546 g, 1.85 mmol), n-BMA (0.105 mL, 0.66 mmol) and BP (0.027 g, 0.132 mmol) were dissolved in 5.3 mL ethanol (total monomer concentration 1.0 mmol mL$^{-1}$) with initiator AIBN (0.01 mmol mL$^{-1}$) and the solution was poured into polymerization tube. After degassing with argon for 30 minutes, the polymerization reaction was carried out under nitrogen flow at 60° C. for 16 h. The reaction was stopped by exposing the solution to air, cooled to room temperature, and poured into ethyl ether to precipitate the polymer. The white solid was collected by vacuum filtration and dried under vacuum for 12 h. Yield: 0.552 g, 83%. $^1$H NMR (D$_2$O) was taken to confirm the polymer composition.

Crosslinking of BPMPC with Substrates

Silicon substrates were cut into 2.4 cm×2.4 cm pieces and sonicated with deionized water, isopropanol, and acetone for 5 min each then dried under nitrogen, followed by plasma (Harrick Plasma PDC-32G) clean and treated with iBTS in toluene overnight before modification with the polymer. CarboSil substrates were coated with polymer without pretreatment.

Two coating methods were utilized when applying BPMPC on substrates: spin coating and spray coating. For spin coating, polymer modified film was developed on functionalized silicon substrate by using 0.5 mL BPMPC/ethanol solution (10 mg mL$^{-1}$) at 1000 rpm for 30 seconds. Spray coating was applied for CarboSil films with and without SNAP. BPMPC/ethanol solution (2 mg mL$^{-1}$) was sprayed using a spray gun from a distance of 10 cm onto vertically placed substrates to achieve uniform coating upon drying. Spin coating was used in the protein adsorption experiments, and spray coating in SNAP/NO release and bacterial experiments, based on method that afforded the smoothest, pin-hole free coating on different forms of substrate. Then the BPMPC substrates were irradiated with UV light (UVP, 254 nm, 6.5 mW cm$^{-2}$) for 1 min to covalently bond the BPMPC to the surface. The substrates were rinsed with abundant ethanol to remove unattached BPMPC then dried under nitrogen.

Characterization of the Polymer Coatings

The surface wettability was characterized by measuring the static water contact angle, which obtained from a DSA 100 drop shape analysis system (KRÜSS) with a computer-controlled liquid dispensing system. 1 µL DI water droplets were deposited onto substrate surfaces, and the water contact angles were measured within 10 seconds through the analysis of photographic images. The cross-linking kinetics of BPMPC coating was investigated by a UV-vis spectroscopy (Varian) with 254 nm UV light. The thickness of the spin-coated polymer layer on the silicon substrates and CarboSil substrates were measured by M-2000V Spectroscopic Ellipsometer (J.A. Woollam co., INC.) with a white light source at three incident angles (65°, 70°, and 75°). The thickness of the modified layer was measured and calculated using a Cauchy layer model. Infrared spectroscopy studies of polymer coated films were done using a Thermo-Nicolet model 6700 spectrometer equipped with a variable angle grazing angle attenuated total reflection (GATR-ATR) accessory (Harrick Scientific).

SNAP Leaching Study and NO-Release Profile

The percentage of SNAP discharged from the samples were quantified by noting the absorbance of the PBS solutions (used to soak the samples) at 340 nm (characteristic absorbance maxima of S—NO group of SNAP). Each sample was weighed before coating with non-SNAP polymer solutions to determine the initial amount of SNAP in each film. The films were then immersed in vials containing PBS (pH 7.4 with 100 µM EDTA to prevent catalysis of NO release by metal ions) and stored at 37° C. A UV-vis spectrophotometer (Thermoscientific Genesys 10S UV-vis) was utilized to quantify the absorbance of the buffer solutions in the required time intervals. The readings were converted to wt % of SNAP in the buffer utilizing the initial amount of SNAP present in each sample. 1 mL aliquots of the PBS solution in which the samples were soaked was used for each sample absorbance measurement to avoid any inconsistent readings and three replicates were utilized for each quantification. The calibration graph with known amounts of SNAP in PBS (with EDTA) was used to interpolate the absorbance quantifications recorded from the study and convert them to concentrations of SNAP in the quantified sample.

SNAP incorporated in the polymers release NO in physiological conditions and this release was measured and recorded in real time for the study using Sievers chemiluminescence NO Analyzers® (NOA 280i, GE Analytical, Boulder, Colo., USA). The sample holder maintained dark conditions for the samples to prevent catalysis of the NO production by any light source. It was filled with 5 mL of PBS (pH 7.4 with 100 µM of EDTA) to soak the samples. EDTA acted as a chelating agent to prevent catalysis of NO production by metal ions in the PBS. This buffer solution was maintained at 37° C. by a temperature-regulated water jacket placed around the sample holder. Once a baseline of NO flux without the sample (prepared according to Example 2: Nitric Oxide release kinetics) is established, the sample is then placed in the sample holder. Nitric oxide released by the sample in the sample holder was pushed and purged towards the analyzer by a continuous supply of nitrogen gas maintained at a constant flow rate of 200 mL min$^{-1}$ through the sweep and bubble flows. The NO released by the sample is pushed towards the chemiluminescence detection chamber where the reactions shown on FIG. 1 take place.

The voltage signal produced is converted to concentration of NO and displayed on the analyzer's screen. Using the raw data in ppb form and NOA constant (mol ppb$^{-1}$ s$^{-1}$), the data in ppb is normalized for surface area of the sample and converted to NO flux units (×10$^{-10}$ mol cm$^{-2}$ min$^{-1}$). Data was collected in the time intervals mentioned and samples were stored in a PBS (with EDTA) solution at 37° C. in dark conditions between measurements. The PBS was replaced daily to avoid any accumulation of SNAP leached or NO released during the storage time. The instrument operating parameters were a cell pressure of 7.4 Torr, a supply pressure of 6.1 psig and a temperature of −12° C. Three replicates were used for each measurement.

Protein Adhesion Assay

Protein adsorption test is a significant important method for evaluating the blood adhesion. Therefore, the thickness change of substrates before and after incubation in protein solutions was monitored, as an indication of protein adsorption. Coated substrates were incubated in fibrinogen (1 mg mL$^{-1}$) and lysozyme (1 mg mL$^{-1}$) in PBS (pH 7.4, 0.01 M) solutions up to 14 days, followed by thickness measurement every day.

In the second approach, fluorescein isothiocyanate-bovine serum albumin (FITC-BSA, 2 mg mL$^{-1}$) in PBS solution was used to evaluate the protein adsorption behavior on the surface of CarboSil substrate modified by BPMPC.[42-43] Substrates were immersed in FITC-BSA solution for one and half hour at 37° C., then rinsed with distilled water and dried with nitrogen. The substrates with protein then analyzed by Nikon Eclipse NI-U fluorescence microscope (Nikon Instruments, Inc.), using a 5× objective lens, with filter set (Ex/Em 470/525 nm). To confirm the long-term resistance to protein adsorption, the substrates were incubated in BSA (1 mg ml$^{-1}$) PBS solution for up to 7 days at 37° C. before putting in FITC-BSA solution.

Bacterial Assay

Bacterial adhesion for each of the samples was calculated in terms of the bacterial cell viability using serial dilution after an incubation period of 24 hours. The method used to perform this assay was based on a modified version of the American Society for Testing and Materials E2180 protocol. *S. aureus* was used for antimicrobial evaluation of the samples. Bacteria were cultured in LB Broth (Lennox) at 37° C. and grown to ~10$^6$ colony-forming units (CFU) per mL as measured by optical density. The resulting overnight culture was collected by centrifugation (2500 g, 7 min) and resuspended in PBS. This resuspended bacterial suspension was used for incubation of polymer samples for 24 hours.

After incubation with the bacterial solution, samples were washed gently with PBS to remove any unbound bacteria. The samples were then placed in 1 mL of PBS and homogenized for 1 minute each to transfer any adhered bacteria to this new PBS solution. After homogenization, homogenate samples were serially diluted and plated onto LB Agar nutrient plates (37° C.). Bacterial viability was determined by counting the colonies on each plate manually. Calculation of bacterial adhesion was done by counting number of colonies per cm$^2$ of each sample.

Statistical Analysis

All data are quantified as mean±standard deviation with an n≥3 for all trials. The results between the control and test films were analyzed by a comparison of means using student's t-test. Values of p were obtained for the data analyzed and p<0.05 was considered significant.

Results and Discussion

The zwitterionic polymer (BPMPC) was synthesized by radical polymerization in ethanol (Scheme 1A). The copolymer composition was confirmed by $^1$H NMR spectroscopy, and consisted of 74:18:8 (MPC:nBMA:BP), which roughly matched the monomer feed ratio. This ratio provided the optimal anti-fouling result (discussed below) along with the most uniform coating on both hydrophobic and hydrophilic substrates. The polymer synthesis is simple and straightforward, no further purification is required besides precipitation, which makes large-scale production feasible. BPMPC is a hydrophilic polymer due to the high concentration of MPC, and has a high solubility in aqueous and alcohol solutions. The butyl methacrylate component in the terpolymer aids in uniformity and substrate wetting (both hydrophobic and hydrophilic), along with providing additional photochemical cross-linking sites. As described above, the benzophenone component of BPMPC acts as a cross-linker between the hydrophilic polymer and any organic substrate through C—H activation.

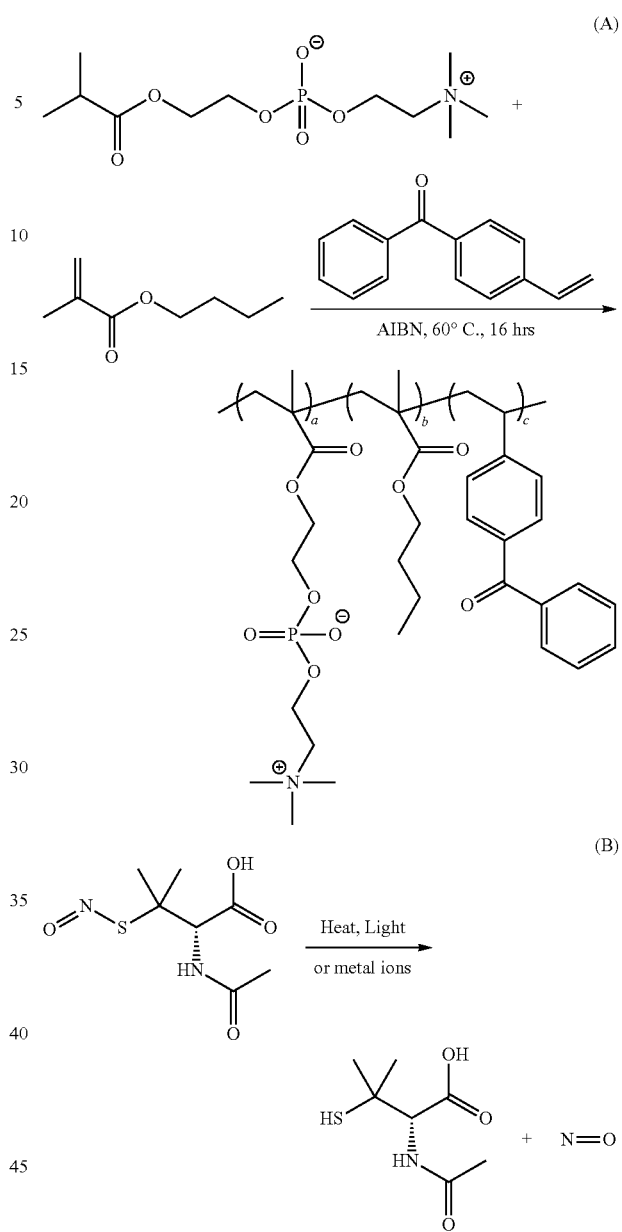

Scheme 1A shows synthesis of the BPMPC copolymer. Scheme 1B shows the chemical structure of SNAP and NO decomposition along with innocuous N-acetylpenicillamine byproduct.

Figure 2:
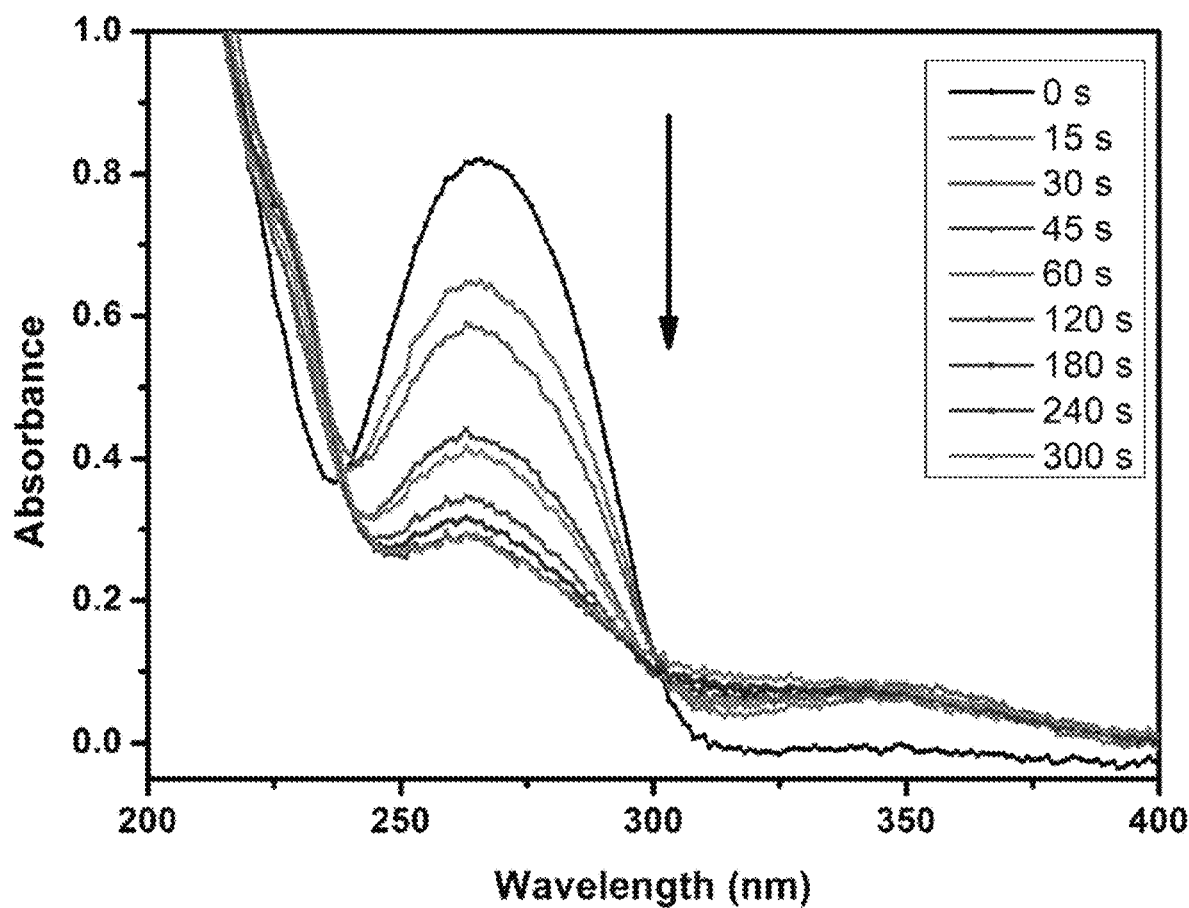
FIG. 2 shows UV-vis absorption spectrum of BPMPC drop-cast onto a quartz substrate as a function of photochemical irradiation time at 254 nm (6.5 mW cm$^{-2}$ intensity).

The cross-linking kinetics of BPMPC was investigated by UV-vis spectroscopy on isobutyltrichlorosilane (iBTS) functionalized quartz substrates. The polymer solution (10 µL, 10 mg mL$^{-1}$) was drop cast on alkylated quartz and the solvent allowed to evaporate. The UV crosslinking reaction was monitored by UV-vis, where the decreasing absorbance of the BP group at 255 nm occurs with increased irradiation time. FIG. 2 shows the UV-vis spectra, where the absorbance maxima at 255 nm decreased dramatically from 0 to 120 s, and after 240 s, no further absorbance change was observed, even after prolonged irradiation. This result demonstrates that BPMPC crosslinking occurs with rapid kinetics, and only a few seconds are needed to covalently bond BPMPC to a variety of different substrates.

Figure 3:
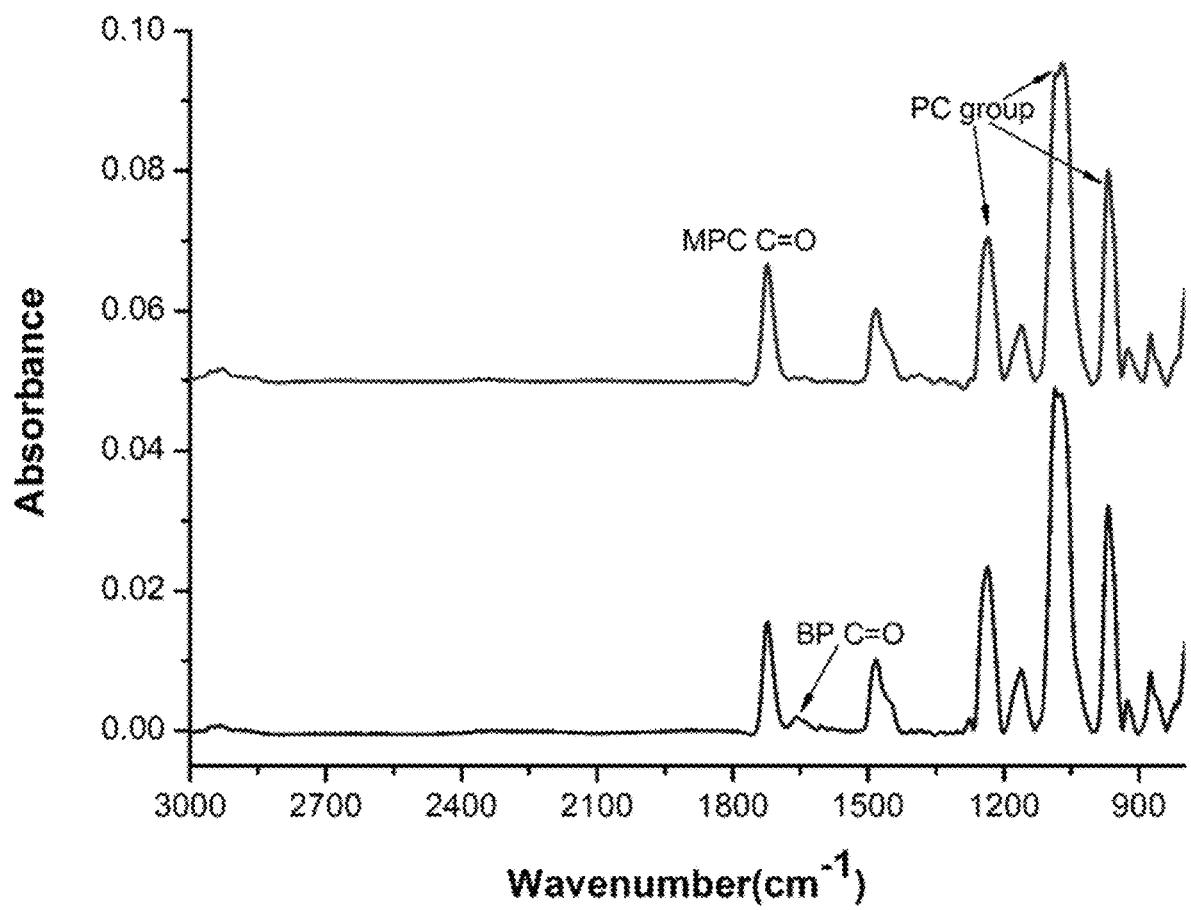
FIG. 3 shows ATR-FTIR spectra of BPMPC coatings before (lower curve) and after (upper curve) UV exposure.

To further confirm the deposition and cross-linking of the BPMPC polymer, FTIR was conducted on coated substrates. In the IR spectra (FIG. 3), absorption peaks of the carbonyl (1720 cm$^{-1}$) and PC groups (1240, 1080, and 970 cm$^{-1}$) were observed and assigned to the MPC units. The peak at (1650 cm$^{-1}$) represents the C=O stretch of BP ketone. A significant reduction of this peak after irradiation further supports the formation of a network polymer of covalent linkage between BP and substrate.

Figure 4:
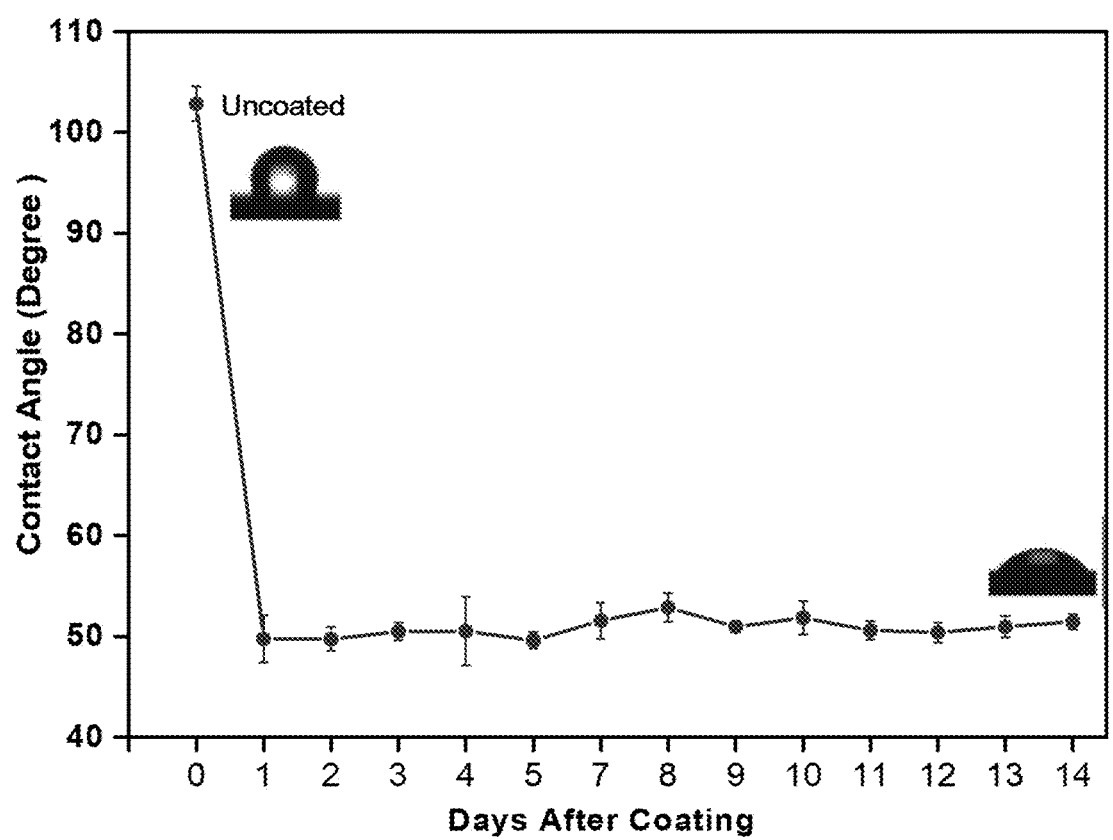
FIG. 4 shows contact angle measurement as a function of time for CarboSil coated with BPMPC and incubated at 37° C. in PBS under mild agitation.

To test the stability and durability of the coating, the water contact angle of the BPMPC coated silicon samples were monitored for up to 14 days. The coated substrates were immersed in PBS solution and stirred in an incubator at 37° C., subsequently rinsed with H$_2$O and dried with nitrogen before measuring the water contact angle (FIG. 4). The initial static contact angle for the bare CarboSil substrate is about 110°. A significant decrease in contact angle was observed after coating with BPMPC, from 110° to 50°, and this value of contact angle was maintained over a period of 14 days immersed in an agitated PBS solution, which suggests the BPMPC coating was covalent bonded to the substrates and does not delaminate under physiological conditions.

The control samples used to test NO release behavior were coated only with CarboSil (the same polymer used to incorporate SNAP) while the test samples were coated with CarboSil and BPMPC. The samples were tested in lightly agitated conditions to simulate physiological conditions. The samples were tested for a period of two weeks to demonstrate sustainable release of NO from the combination of hydrophobic and hydrophilic polymers.

Figure 5A:
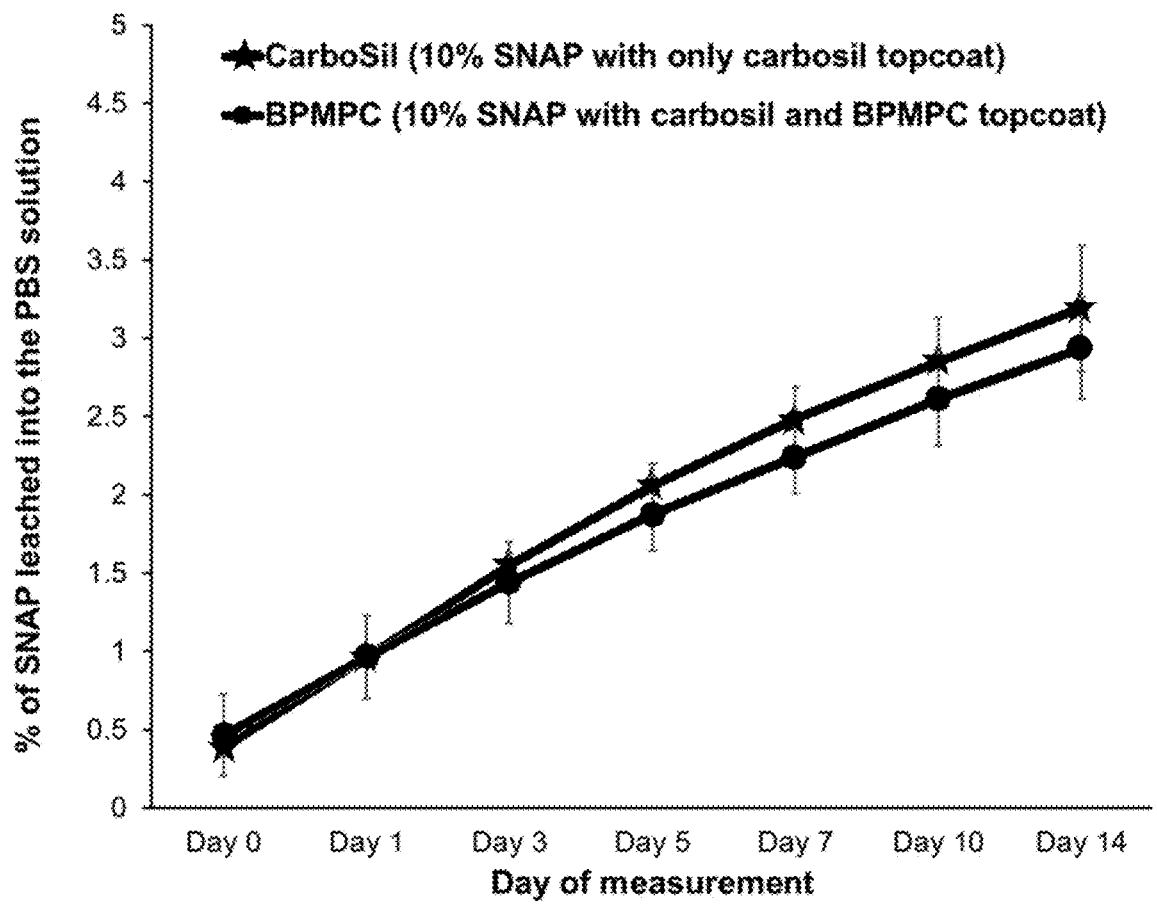
FIGS. 5A-5B show SNAP leaching measured using UV-vis over 2 weeks and Nitric oxide release measured over 2 weeks (n=3) using chemiluminescence.

A SNAP leaching study was conducted first to measure the retention of SNAP in the control and test polymer films during the course of the study. Measurements were recorded every other day for 2 weeks of soaking in PBS (FIG. 5A). A high amount of SNAP retention in the polymers ensures sustained release of NO from the polymer matrix and minimizes the risks (if any) associated with SNAP leaching.[44] As seen in FIG. 5A, for the initial measurement (Day 0 on graph of FIG. 5A) of leaching after one hour of storage in 37° C. in PBS, a loss of 0.39±0.06% and 0.47±0.26% was recorded for the control and BPMPC-coated substrate, respectively. This initial higher leaching for the BPMPC-coated substrate is likely due to the hydrophilicity of the surface. However, SNAP leaching is almost identical between the control and test samples as supported by the data from 1 and 3 days of storage in 37° C. for BPMPC-coated test films (0.96±0.26% and 1.44±0.26% for day 1 and day 3, respectively) and control films (0.96±0.05% and 1.55±0.07% for day 1 and day 3, respectively).

This trend of lower leaching of the SNAP molecules from the test films was observed over a 14 day period. It is also to be noted that at no point during the 14-day period were the samples kept at a temperature below 37° C. or in dry conditions. This was done to closely simulate physiological conditions for a continuous duration. The leaching for both the control and test samples remained very low (<3.5%) over the experiment duration but it is worth noting here that despite the expectation that the hydrophilic coating could cause a higher leaching of SNAP molecules from the NO donor containing polymer by attracting water molecules to the polymer surface, this was not the case. This is likely due to the ultrathin nature of the coating, which influences the aqueous interface, but not the bulk of the polymer film.

Figure 5B:
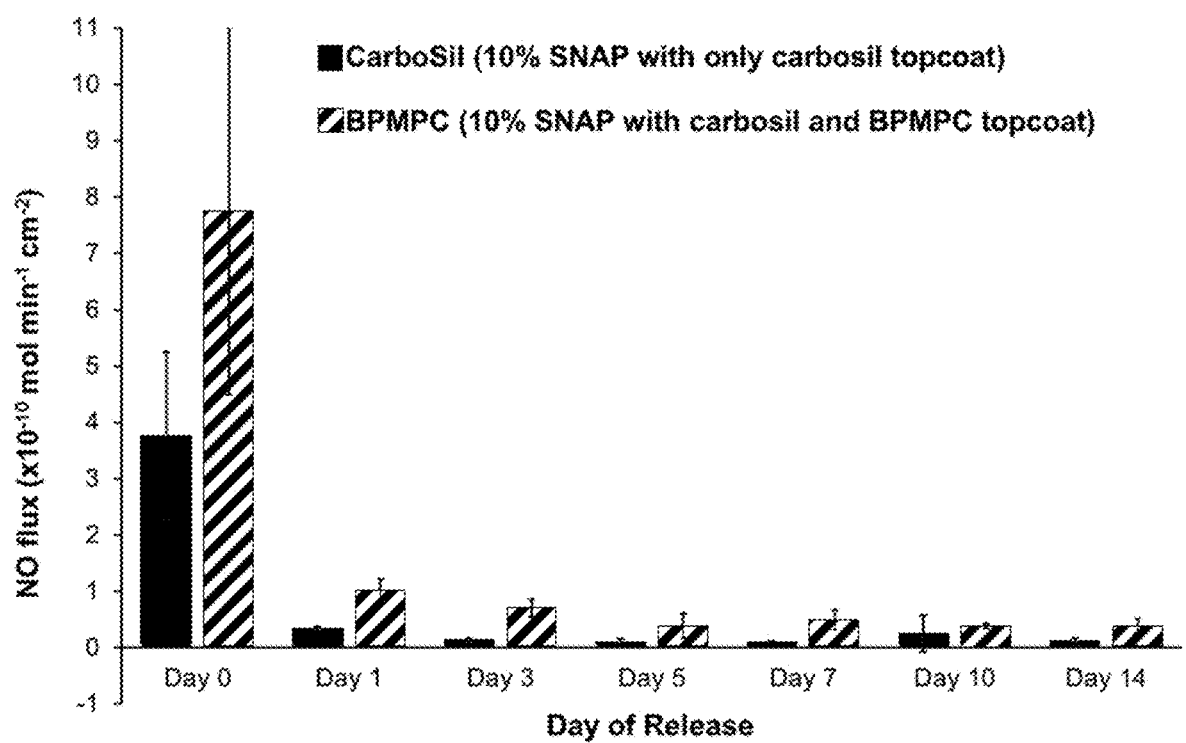

NO release measurements of the control and test samples were also carried out for a period of 14 days (FIG. 5B). Measurements with a Sievers chemiluminescence NO analyzer is the standard characterization methodology accepted for polymers that release NO.[45-47] It measures NO release in real time via the measurement of voltage produced by the photons on the reaction of NO with ozone. Samples were stored at a constant temperature of 37° C. and in PBS to simulate physiological conditions.

The results indicated a general trend of higher NO release from the test samples (SNAP-containing material coated with CarboSil and BPMPC) compared to the control samples (SNAP-containing material coated with only CarboSil). Day 0 measurements indicate that the test samples had a flux of 7.75±3.26 (×10$^{-10}$) mol cm$^{-2}$ min$^{-1}$ while control samples had a flux of 3.76±1.50 (×10$^{-10}$) mol cm$^{-2}$ min$^{-1}$ (Table 1). This burst of NO release from test samples results from the hydrophilicity of the topcoat which attracts water molecules to the sample surface. Water molecules on the surface can accommodate release of NO as SNAP is more soluble (and prone to S—N=O bond cleavage) in aqueous conditions. After a day of storage, the control samples show a sharp decrease in NO flux (0.34±0.03×10$^{-10}$ mol cm$^{-2}$ min$^{-1}$). This is seen because of the initial loss in SNAP molecules on day 0 and inability to maintain a hydrated state for day 1. In contrast, BPMPC-coated substrates show three times the NO flux at 1.02±0.02×10$^{-10}$ mol cm$^{-2}$ min$^{-1}$. This difference in NO flux can result from the hydrophilic topcoat of test samples that maintains a hydrated surface layer, which facilitates the release of more NO. This trend of higher NO flux from test samples when compared to control samples can be seen through the 14-day study in Table 1 and the graph in FIG. 5B.

TABLE 1

Comparison of nitric oxide release kinetics between control and coated samples

|  | 10% SNAP with only CarboSil topcoat (NO flux (×10$^{-10}$ mol min$^{-1}$ cm$^{-2}$) | 10% SNAP with CarboSil and BPMPC topcoat (NO flux (×10$^{-10}$ mol min$^{-1}$ cm$^{-2}$) |
|---|---|---|
| Day 0 | 3.759 ± 1.491 | 7.746 ± 3.263 |
| Day 1 | 0.335 ± 0.032 | 1.016 ± 0.198 |
| Day 3 | 0.141 ± 0.023 | 0.706 ± 0.157 |
| Day 5 | 0.110 ± 0.045 | 0.395 ± 0.208 |
| Day 7 | 0.105 ± 0.008 | 0.498 ± 0.173 |
| Day 10 | 0.247 ± 0.324 | 0.383 ± 0.040 |
| Day 14 | 0.127 ± 0.035 | 0.380 ± 0.125 |

At the end of the 14-day study, test samples (0.38±0.13 (×10$^{-10}$) mol cm$^{-2}$ min$^{-1}$) still release three times the NO flux compared to the control samples (0.13±0.03 (×10$^{-10}$) mol cm$^{-2}$ min$^{-1}$). This propensity of higher release of NO from CarboSil top-coated with BPMPC along with the reduction in leaching of SNAP is very beneficial and combines the material properties of CarboSil (low SNAP leaching) with a higher, sustained release of NO due to the hydrophilic BPMPC topcoat.

Figure 6A:
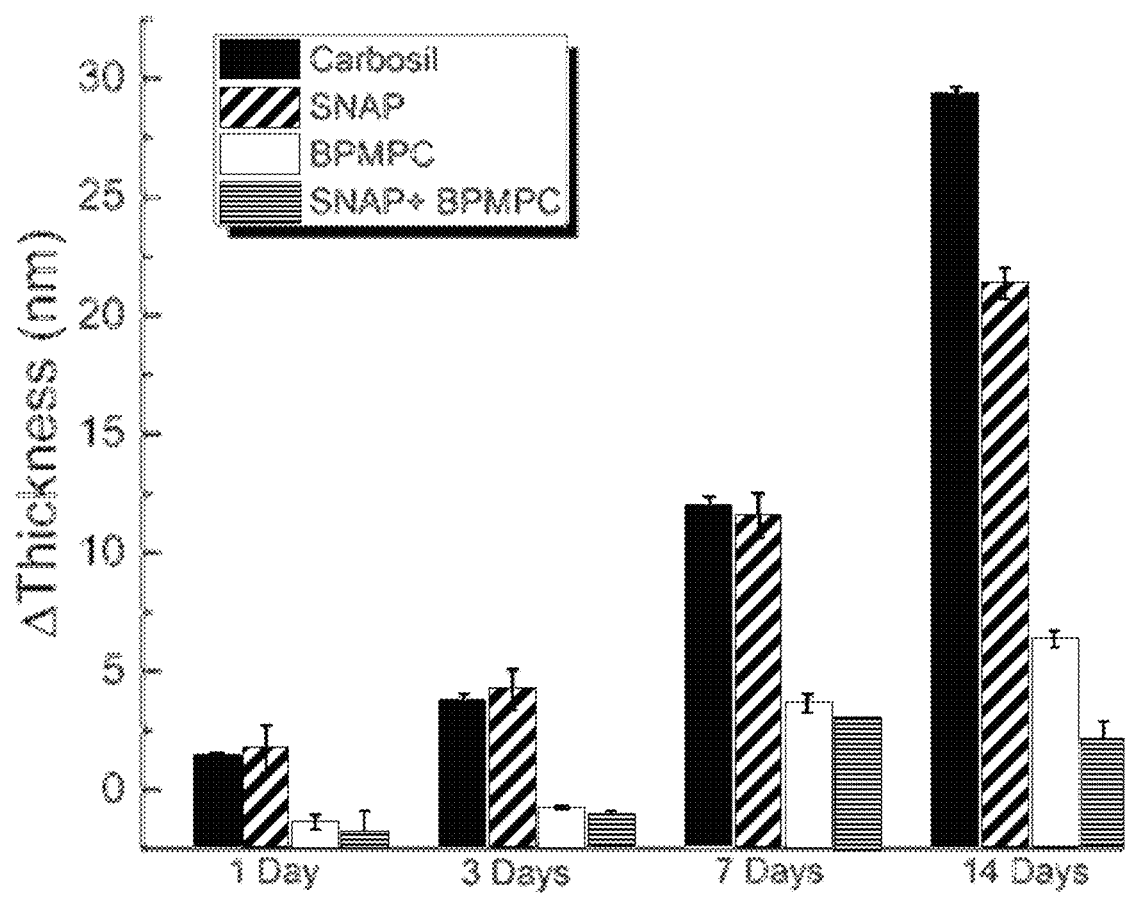
FIGS. 6A-6B show thickness increase after incubation in (FIG. 6A) Fibrinogen solution and in (FIG. 6B) Lysozyme solution.
Figure 6B:
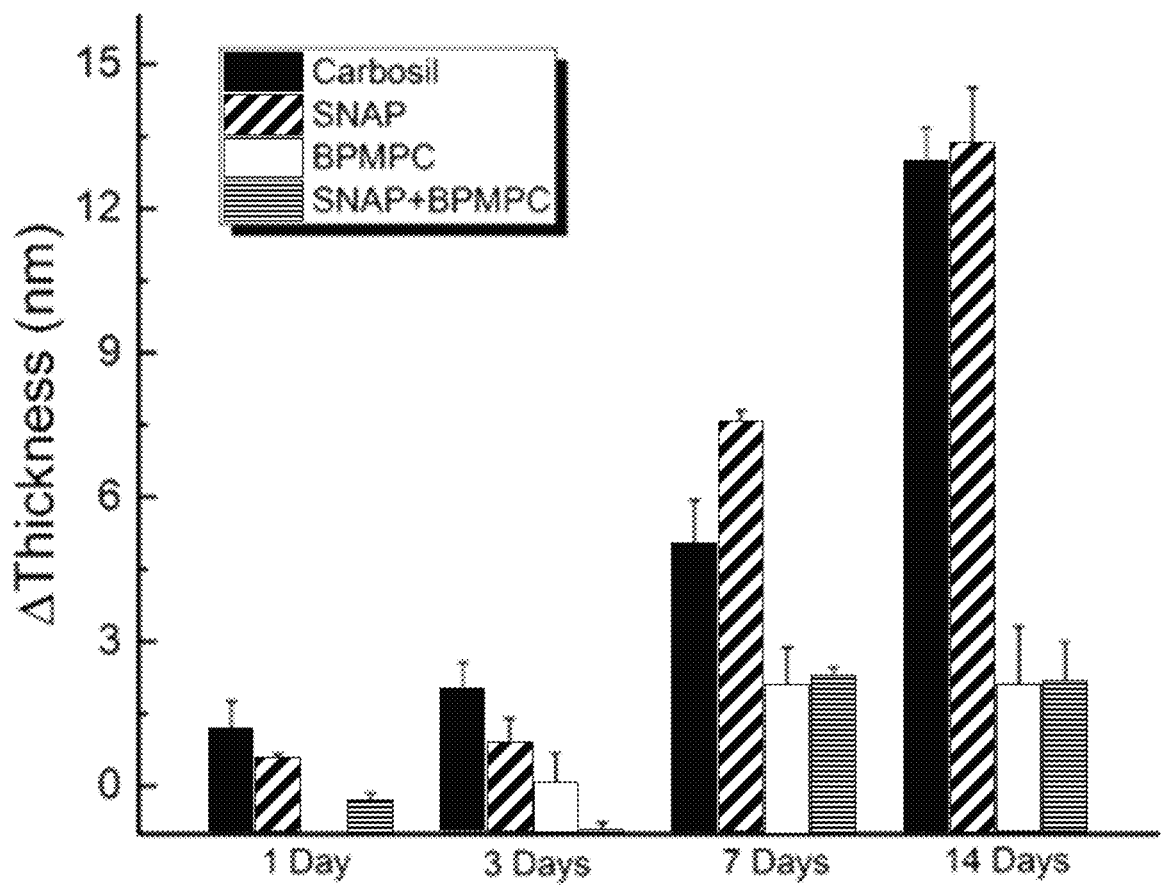

As mentioned earlier, the BPMPC coating has excellent hydrophilicity, which helps inhibit the adsorption of proteins from solution. Fibrinogen and lysozyme were used as model proteins to evaluate the antifouling properties of the BPMPC coatings. Fibrinogen is a large (340 kD, pI=6.0) protein, and a key biomacromolecule in the coagulation cascade that rapidly adsorbs to foreign surfaces and binds to and activates platelets. Lysozyme is a small protein (14 kD, pI=12) that is positively charged under physiological pH. FIG. 6A shows the adsorption thickness increase of Fibrinogen on CarboSil, CarboSil with 10% SNAP, BPMPC coated CarboSil, and BPMPC coated CarboSil with 10% SNAP substrates respectively. On the bare CarboSil films used as a control, the thickness increased about 2 nm after incubation for 24 hours, and increased to over 30 nm after 2 weeks. The similar phenomenon was observed for CarboSil with 10% SNAP films, which indicated a high amount of protein adsorption on surface, and protein accumulation over time. On the other hand, for the CarboSil films coated with BPMPC, the adsorption amount is significantly lower, only a 3 nm increase was observed after incubation for 2 weeks. The large difference in adsorption thickness confirmed that BPMPC coating has excellent protein resistance properties, even after UV activation. As expected, the BPMPC coated CarboSil with 10% SNAP films also shows low adsorption for Fibrinogen. Moreover, similar behavior was observed when films were subjected to lysozyme solution (FIG. 6B). The thickness increase in control group was over 14 nm, while the coated group was less than 3 nm. The protein adsorption results indicate that the hydrophilic BPMPC surface layer provides excellent protein-resistant properties.

Figures 7A, 7B, 7C, 7D, 7E, 7F:
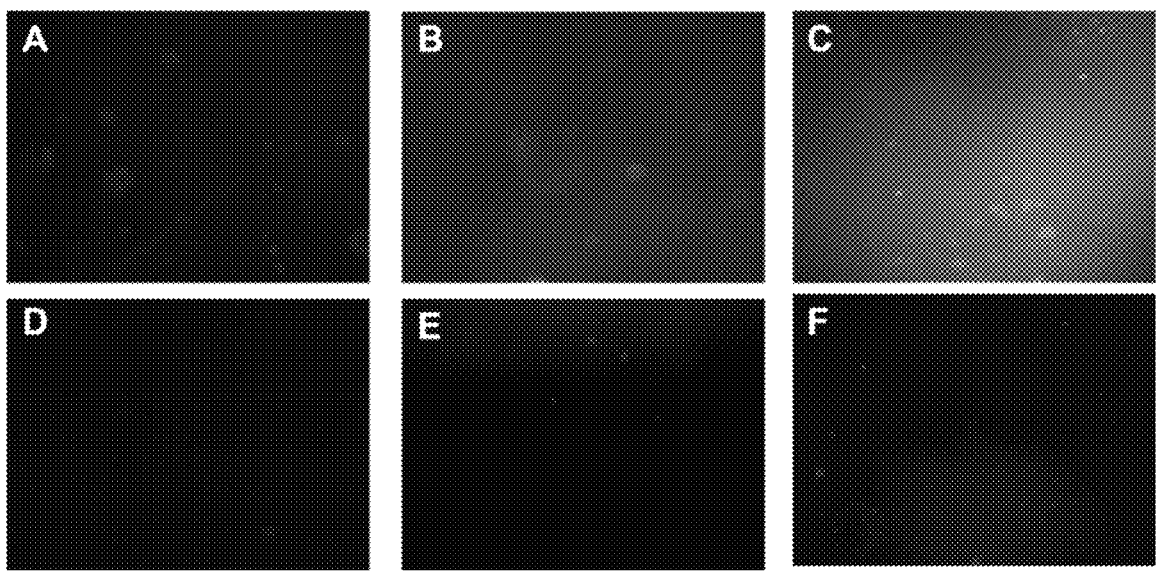
FIGS. 7A-7B show fluorescence micrographs (magnification 10x) of uncoated films after (FIG. 7A) 90-minute incubation, (FIG. 7B) 1 day in BSA PBS solution before incubation, and (FIG. 7C) 7 days in BSA PBS solution before incubation in 2 mg/ml FITC-BSA solution.
(FIGS. 7D-7F) are the coated film measured under the same experimental conditions.

To further confirm the antifouling effectiveness of the durable BPMPC coating, fluorescence microscopy was utilized to evaluate the protein adsorption on the uncoated and coated CarboSil films using FITC labeled BSA protein. The fouling levels were compared between uncoated and BPMPC coated CarboSil films using the same excitation light intensity and exposure time. FIG. 7A indicates protein adsorption on the control samples, and enhanced fluorescent signal (FIGS. 7B-7C) was observed in the samples pretreated with BSA PBS solution. These results demonstrate that after incubation in protein solution, a large amount of BSA was attached to the CarboSil samples, which facilitate the aggregation of FITC-BSA. On the contrary, protein adhesion to the surface of BPMPC modified samples was not observed (FIGS. 7D-7F), even after incubation in BSA solution for 7 days. From all of these results collectively, the control films demonstrate large amounts of protein adsorption, while the BPMPC coated films display excellent antifouling properties.

Bacterial adhesion, which often results in biofilm formation, is a prevalent issue in moist and humid environments, including implanted devices. The basic nutrients important for bacterial growth may be resourced from the device material, bodily proteins that attach post-implantation, or other bodily macromolecular contaminants that adhere to the surface of the device. Antimicrobial efficacy of the designed test samples was compared to the control samples to confirm their superior bactericidal and bacterial repulsion properties.

The samples were soaked in bacterial solutions containing ~$10^6$ CFU/mL of *S. aureus*. *S. aureus* is a commonly found nosocomial infection bacteria. It has been increasingly linked with healthcare-associated infections in the last two decades.[48] They are most commonly associated with cardiac devices, intravascular catheters and urinary catheters, among other prosthetic devices. This high prevalence of *S. aureus* along with its known affinity to proteins[49-50] that foul medical devices has made it a very important pathogen used to evaluate the antimicrobial efficacy of medical device materials. For these reasons, bacterial adhesion study of the antifouling-biocide releasing polymer developed was done with *S. aureus*.

Figure 8:
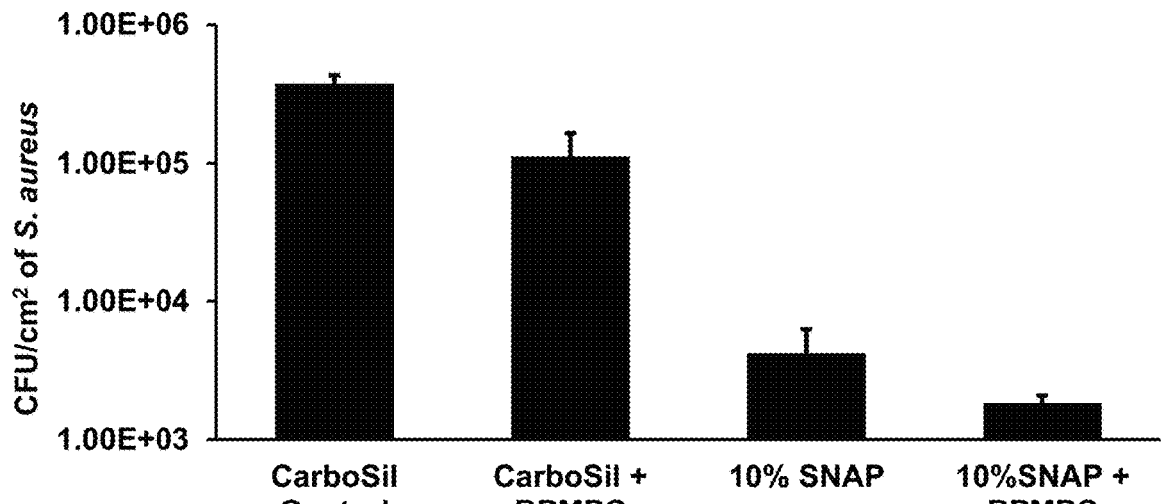
FIG. 8 shows antimicrobial efficacy of NO-releasing BPMPC coated samples relative to controls (n=3).

As mentioned in the introduction, the NO molecules liberated by the decomposition of SNAP actively kill bacteria while the zwitterion topcoat repels protein adsorption, leading to enhanced antimicrobial efficacy. After 24-hours of incubation, the antimicrobial effect of the test samples was clearly observed. NO releasing polymers with a top-coat of BPMPC showed a bactericidal efficiency of 99.91±0.06% (~3 log reduction, FIG. 8) compared to the control samples where a growth of ~$10^6$ CFU/cm$^2$ was observed. This reduction is greater compared to films with only a BPMPC topcoat (70.15±14.13%) and also films with only NO-releasing moieties (98.88±0.54%). It can also be concluded from the results that BPMPC alone only reduces bacteria adhesion. However, because NO is not a contact active antimicrobial but a diffusing biocide, the SNAP-loaded samples also reduce bacterial adhesion significantly.

These results are consistent with the theoretical expectations underlying the surface chemistry of BPMPC and bactericidal properties of NO. In summary, the synergistic effect of the modifiable NO-release kinetics from CarboSil's surface and prevention of protein and/or bacterial adhesion due to BPMPC's surface chemistry will significantly reduce undesired clinical consequences for implanted medical devices.

Conclusions

In conclusion, examples of the present disclosure have demonstrated a combination of NO release and BPMPC can produce a material with antimicrobial ability and excellent antifouling properties. The formation of the covalent polymer network is rapid (less than 1 min) under mild UV conditions, and can be applied to various substrates, from hydrophilic to hydrophobic. More importantly, even though the BPMPC coating is around 50 nm, it resists moderate abrasion for over a week with retention of its antifouling property. Moreover, the NO release profile indicated a higher NO release from the BPMPC coated sample when compared to the control, with lower leaching of SNAP. The coatings were also challenged with protein adsorption tests for an extended time (up to 2 weeks), where antifouling properties remain. It is noteworthy that, the high killing efficiency of SNAP to *S. aureus* is enhanced by BPMPC coating. This one step photochemical attachment process of an antifouling coating to NO-releasing antimicrobial polyurethanes is a simple and scalable process that has application in both medical devices and other industrial applications where antifouling and antimicrobial properties are desired.

References for Example 1

1. Woo Kyung Cho, B. K., Insung S. Choi, High Wfficient Non-biofouling Coating of Zwitterionic Polymer: Poly ((3-(methacryloylamino)propyl)-dimethyl(3-sulfopropyl) ammonium hydroxide). *Langmuir* 2007, 23, 5678.
2. Nguyen, A. T.; Baggerman, J.; Paulusse, J. M.; van Rijn, C. J.; Zuilhof, H., Stable Protein-repellent Zwitterionic Polymer Brushes Grafted from Silicon Nitride. *Langmuir* 2011, 27 (6), 2587-94.
3. Kenawy el, R.; Worley, S. D.; Broughton, R., The chemistry and applications of antimicrobial polymers: a state-of-the-art review. *Biomacromolecules* 2007, 8 (5), 1359-84.
4. Dastjerdi, R.; Montazer, M., A Review on the Application of Inorganic Nano-structured Materials in the Modification of Textiles: Focus on Anti-microbial Properties. *Colloids Surf B Biointerfaces* 2010, 79 (1), 5-18.
5. Hetrick, E. M.; Schoenfisch, M. H., Reducing Implant-related Infections: Active Release Strategies. *Chem Soc Rev* 2006, 35 (9), 780-9.
6. Yatvin, J.; Gao, J.; Locklin, J., Durable defense: robust and varied attachment of non-leaching poly"-onium" bactericidal coatings to reactive and inert surfaces. *Chem Commun (Camb)* 2014, 50 (67), 9433-42.
7. Magill, S. S.; Edwards, J. R.; Bamberg, W.; Beldavs, Z. G.; Dumyati, G.; Kainer, M. A.; Lynfield, R.; Maloney, M.; McAllister-Hollod, L.; Nadle, J.; Ray, S. M.; Thompson, D. L.; Wilson, L. E.; Fridkin, S. K.; Emerging Infections Program Healthcare-Associated, I.; Antimicrobial Use Prevalence Survey, T., Multistate Point-prevalence Survey of Health Care-associated Infections. *N Engl J Med* 2014, 370 (13), 1198-208.
8. Lowe, S.; O'Brien-Simpson, N. M.; Connal, L. A., Antibiofouling Polymer Interfaces: Poly(ethylene glycol) and Other Promising Candidates. *Polym. Chem.* 2015, 6 (2), 198-212.
9. Jiang, S.; Cao, Z., Ultralow-fouling, Functionalizable, and Hydrolyzable Zwitterionic Materials and their Derivatives for Biological Applications. *Adv Mater* 2010, 22 (9), 920-32.
10. Wayne R. Gombotx, W. G., Thomas A. Horbett, Allan S. Hoffman, Protein Adsorption to Poly(ethylene oxide) Surfaces. *J. Biomed. Mater. Res.* 1991, 25, 1547-1562.
11. Shao, Q.; Jiang, S., Molecular Understanding and Design of Zwitterionic Materials. *Adv Mater* 2015, 27 (1), 15-26.
12. Zhang, Z.; Chao, T.; Chen, S. F.; Jiang, S. Y., Superlow Fouling Sulfobetaine and Carboxybetaine Polymers on Glass Slides. *Langmuir* 2006, 22 (24), 10072-10077.
13. Hucknall, A.; Rangarajan, S.; Chilkoti, A., In Pursuit of Zero: Polymer Brushes that Resist the Adsorption of Proteins. *Advanced Materials* 2009, 21 (23), 2441-2446.
14. Ladd, J.; Zhang, Z.; Chen, S.; Hower, J. C.; Jiang, S., Zwitterionic Polymers Exhibiting High Resistance to Nonspecific Protein Adsorption from Human Serum and Plasma. *Biomacromolecules* 2008, 9 (5), 1357-1361.
15. Holmlin, R. E.; Chen, X. X.; Chapman, R. G.; Takayama, S.; Whitesides, G. M., Zwitterionic SAMs that Resist Nonspecific Adsorption of Protein from Aqueous Buffer. *Langmuir* 2001, 17 (9), 2841-2850.
16. He, Y.; Hower, J.; Chen, S. F.; Bernards, M. T.; Chang, Y.; Jiang, S. Y., Molecular Simulation Studies of Protein Interactions with Zwitterionic Phosphorylcholine Self-assembled Monolayers in the Presence of Water. *Langmuir* 2008, 24 (18), 10358-10364.
17. Singha, P.; Locklin, J.; Handa, H., A review of the recent advances in antimicrobial coatings for urinary catheters. *Acta Biomaterialia* 2017, 50, 20-40.
18. Ren, P. F.; Yang, H. C.; Liang, H. Q.; Xu, X. L.; Wan, L. S.; Xu, Z. K., Highly Stable, Protein-Resistant Surfaces via the Layer-by-Layer Assembly of Poly(sulfobetaine methacrylate) and Tannic Acid. *Langmuir* 2015, 31 (21), 5851-8.
19. Turro, N. J., *Modern Molecular Photochemistry*. Benjamin/Cummings Pub Co.: Menlo Park, Calif., 1978.
20. Lin, A. A.; Sastri, V. R.; Tesoro, G.; Reiser, A.; Eachus, R., On the Crosslinking Mechanism of Benzophenone-containing Polyimides. *Macromolecules* 1988, 21 (4), 1165-1169.
21. Park, M.-K.; Deng, S.; Advincula, R. C., pH-Sensitive Bipolar Ion-Permselective Ultrathin Films. *Journal of the American Chemical Society* 2004, 126 (42), 13723-13731.
22. Higuchi, H.; Yamashita, T.; Horie, K.; Mita, I., Photo-cross-linking Reaction of Benzophenone-containing Polyimide and Its Model Compounds. *Chemistry of Materials* 1991, 3 (1), 188-194.
23. Braeuchle, C.; Burland, D. M.; Bjorklund, G. C., Hydrogen Abstraction by Benzophenone Studied by Holographic Photochemistry. *The Journal of Physical Chemistry* 1981, 85 (2), 123-127.
24. Lin, X.; Fukazawa, K.; Ishihara, K., Photoreactive Polymers Bearing a Zwitterionic Phosphorylcholine Group for Surface Modification of Biomaterials. *ACS Appl Mater Interfaces* 2015, 7 (31), 17489-98.
25. Samuel, J. D. J. S.; Brenner, T.; Prucker, O.; Grumann, M.; Ducree, J.; Zengerle, R.; Rühe, J., Tailormade Microfluidic Devices Through Photochemical Surface Modification. *Macromolecular Chemistry and Physics* 2010, 211 (2), 195-203.
26. Hu, S.; Ren, X.; Bachman, M.; Sims, C. E.; Li, G. P.; Allbritton, N. L., Surface-Directed, Graft Polymerization within Microfluidic Channels. *Analytical Chemistry* 2004, 76 (7), 1865-1870.
27. Virkar, A.; Ling, M.-M.; Locklin, J.; Bao, Z., Oligothiophene Based Organic Semiconductors with Cross-linkable Benzophenone Moieties. *Synthetic Metals* 2008, 158 (21-24), 958-963.
28. Bunte, C.; Prucker, O.; Konig, T.; Ruhe, J., Enzyme Containing Redox Polymer Networks for Biosensors or Biofuel Cells: A Photochemical Approach. *Langmuir* 2010, 26 (8), 6019-6027.
29. Bunte, C.; Ruhe, J., Photochemical Generation of Ferrocene-Based Redox-Polymer Networks. *Macromol Rapid Comm* 2009, 30 (21), 1817-1822.
30. Gao, J.; Martin, A.; Yatvin, J.; White, E.; Locklin, J., Permanently Grafted Icephobic Nanocomposites with High Abrasion Resistance. *J. Mater. Chem. A* 2016, 4 (30), 11719-11728.
31. Abu-Rabeah, K.; Atias, D.; Herrmann, S.; Frenkel, J.; Tavor, D.; Cosnier, S.; Marks, R. S., Characterization of Electrogenerated Polypyrrole-Benzophenone Films Coated on Poly(pyrrole-methyl metacrylate) Optic-Conductive Fibers. *Langmuir* 2009, 25 (17), 10384-10389.
32. Brandstetter, T.; Bohmer, S.; Prucker, O.; Bisse, E.; zur Hausen, A.; Alt-Morbe, J.; Ruhe, J., A Polymer-based DNA Biochip Platform for Human Papilloma Virus Genotyping. *J Virol Methods* 2010, 163 (1), 40-48.
33. Brisbois, E. J.; Bayliss, J.; Wu, J.; Major, T. C.; Xi, C.; Wang, S. C.; Bartlett, R. H.; Handa, H.; Meyerhoff, M. E., Optimized polymeric film-based nitric oxide delivery inhibits bacterial growth in a mouse burn wound model. *Acta biomaterialia* 2014, 10 (10), 4136-4142.
34. Pegalajar-Jurado, A.; Wold, K. A.; Joslin, J. M.; Neufeld, B. H.; Arabea, K. A.; Suazo, L. A.; McDaniel, S. L.; Bowen, R. A.; Reynolds, M. M., Nitric oxide-releasing polysaccharide derivative exhibits 8-log reduction against *Escherichia coli, Acinetobacter baumannii* and *Staphylococcus aureus*. *Journal of Controlled Release* 2015, 217, 228-234.
35. Backlund, C. J.; Worley, B. V.; Schoenfisch, M. H., Anti-biofilm action of nitric oxide-releasing alkyl-modified poly (amidoamine) dendrimers against *Streptococcus mutans*. *Acta biomaterialia* 2016, 29, 198-205.
36. Fang, F. C., Antimicrobial actions of nitric oxide. *Nitric oxide: biology and chemistry/official journal of the Nitric Oxide Society* 2012, 27, Supplement, S10.
37. Wang, P. G.; Xian, M.; Tang, X.; Wu, X.; Wen, Z.; Cai, T.; Janczuk, A. J., Nitric Oxide Donors: Chemical Activities and Biological Applications. *Chemical Reviews* 2002, 102 (4), 1091-1134.
38. Brisbois, E. J.; Handa, H.; Major, T. C.; Bartlett, R. H.; Meyerhoff, M. E., Long-term nitric oxide release and elevated temperature stability with S-nitroso-N-acetylpenicillamine (SNAP)-doped Elast-eon E2As polymer. *Biomaterials* 2013, 34 (28), 6957-66.
39. Broniowska, K. A.; Hogg, N., The Chemical Biology of S-Nitrosothiols. *Antioxidants & Redox Signaling* 2012, 17 (7), 969-980.
40. Singha, P.; Pant, J.; Goudie, M. J.; Workman, C. D.; Handa, H., Enhanced antibacterial efficacy of nitric oxide releasing thermoplastic polyurethanes with antifouling hydrophilic topcoats. *Biomaterials Science* 2017.
41. Brisbois, E. J.; Davis, R. P.; Jones, A. M.; Major, T. C.; Bartlett, R. H.; Meyerhoff, M. E.; Handa, H., Reduction in Thrombosis and Bacterial Adhesion with 7 Day Implantation of -Nitroso-acetylpenicillamine (SNAP)-Doped Elast-eon E2As Catheters in Sheep. *J Mater Chem B Mater Biol Med* 2015, 3 (8), 1639-1645.
42. Sundaram, H. S.; Han, X.; Nowinski, A. K.; Ella-Menye, J. R.; Wimbish, C.; Marek, P.; Senecal, K.; Jiang, S., One-step dip coating of zwitterionic sulfobetaine polymers on hydrophobic and hydrophilic surfaces. *ACS Appl Mater Interfaces* 2014, 6 (9), 6664-71.
43. Diaz Blanco, C.; Ortner, A.; Dimitrov, R.; Navarro, A.; Mendoza, E.; Tzanov, T., Building an antifouling zwitterionic coating on urinary catheters using an enzymatically triggered bottom-up approach. *ACS Appl Mater Interfaces* 2014, 6 (14), 11385-93.
44. Scatena, R.; Bottoni, P.; Pontoglio, A.; Giardina, B., Pharmacological modulation of nitric oxide release: new pharmacological perspectives, potential benefits and risks. *Curr Med Chem* 2010, 17 (1), 61-73.
45. Wo, Y.; Li, Z.; Brisbois, E. J.; Colletta, A.; Wu, J.; Major, T. C.; Xi, C.; Bartlett, R. H.; Matzger, A. J.; Meyerhoff, M. E., Origin of Long-Term Storage Stability and Nitric Oxide Release Behavior of CarboSil Polymer Doped with S-Nitroso-N-acetyl-d-penicillamine. *ACS Applied Materials & Interfaces* 2015, 7 (40), 22218-22227.
46. Joslin, J. M.; Lantvit, S. M.; Reynolds, M. M., Nitric Oxide Releasing Tygon Materials: Studies in Donor Leaching and Localized Nitric Oxide Release at a Polymer-Buffer Interface. *ACS Applied Materials & Interfaces* 2013, 5 (19), 9285-9294.
47. Privett, B. J.; Broadnax, A. D.; Bauman, S. J.; Riccio, D. A.; Schoenfisch, M. H., Examination of bacterial resistance to exogenous nitric oxide. *Nitric oxide: biology and chemistry/official journal of the Nitric Oxide Society* 2012, 26 (3), 169-73.
48. Tong, S. Y.; Davis, J. S.; Eichenberger, E.; Holland, T. L.; Fowler, V. G., Staphylococcus aureus infections: epidemiology, pathophysiology, clinical manifestations, and management. *Clinical microbiology reviews* 2015, 28 (3), 603-661.
49. Ní Eidhin, D.; Perkins, S.; Francois, P.; Vaudaux, P.; Höök, M.; Foster, T. J., Clumping factor B (ClfB), a new surface-located fibrinogen-binding adhesin of *Staphylococcus aureus*. *Molecular Microbiology* 1998, 30 (2), 245-257.
50. Boland, T.; Latour, R. A.; Stutzenberger, F. J., Molecular basis of bacterial adhesion. In *Handbook of Bacterial Adhesion*, Springer: 2000, pp 29-41.

Example 2

The present example shows the combined effect of the NO-releasing donor (SNAP) and non-leaching quaternary ammonium (BPAM) to prevent the adherence of bacterial cells on the polymeric surface in addition to killing bacteria beyond the direct point of contact. Briefly, polymeric films were prepared by incorporating SNAP in CarboSil® 20 80A (a medical grade silicone-polycarbonate-urethane copolymer). The BPAM was surface immobilized as a top-coat onto SNAP-CarboSil films by UV based photocrosslinking. The SNAP-BPAM based strategy to kill bacteria on the polymer surface was characterized physically and chemically and validated for its antibacterial efficiency.

Materials and Methods

Materials

CarboSil® 20 80A thermoplastic silicone-polycarbonate-urethane (hereafter will be referred to as CarboSil) was obtained from DSM Biomedical (Berkeley, CA). N-Acetyl-D-penicillamine (NAP), methanol, sodium chloride, potassium chloride, potassium phosphate monobasic, sodium phosphate dibasic, dimethylacetamide (DMAc), tetrahydrofuran (THF), ethylenediaminetetraacetic acid (EDTA), and sulfuric acid were obtained from Sigma-Aldrich (St. Louis, MO). N-Bromosuccinimide (NBS), 2, 2'-azo-bis(2-methyl-propionitrile) (AIBN), and N, N-dimethyl dodecyl amine were purchased from Alfa-Aesar. LB broth, Lennox, and LB Agar, miller media were purchased from Fischer Bioreagents (Fair Lawn, NJ). 4-Methylbenzophenone (Oxchem), cyclohexane (Honeywell), tert-amyl alcohol (JT Baker), isopropyl alcohol (IPA) (JT Baker), sodium chloride (EMD Chemical), and peptone (HiMedia) were used without further purification. Phosphate buffered saline (PBS), pH 7.4, containing 138 mM NaCl, 2.7 mM KCl, 10 mM sodium phosphate, was used for all in vitro experiments including bacteria testing. The two-color fluorescent live/dead BacLight bacterial viability kit L7012 (Molecular Probes, Life Technologies) which contains SYTO® 9 green fluorescent nucleic acid stain and the propidium iodide red fluorescent nucleic acid stain was utilized to evaluate the bacterial viability. Gram-negative *Pseudomonas aeruginosa* (ATCC 27853) and Gram-positive *Staphylococcus aureus* (ATCC 6538) were originally obtained from American Type Tissue Collection (ATCC).

Instrumental Methods

UV-vis spectroscopy was performed on a Cary Bio Spectrophotometer (Varian). Two irradiation wavelengths, 254 and 365 nm, were utilized in this study. The UV light sources were a Compact UV lamp (UVP) and FB-UBXL-1000 UV Crosslinker (Fisher Scientific) with bulbs of 254 nm wavelength for small (1×1 cm) and larger (2.5×2.5 cm) substrates, respectively. The substrates were held at 0.5 cm from the light source during irradiation to obtain a power of 6.5 mW/cm$^2$. Another UV light source was an OmniCure, Series 1000 with 365 nm bandpass filter, equipped with a liquid-filled fiber optic waveguide. The polymeric composite films were held 2 cm from the source for a power of 25 mW/cm$^2$. The thickness of the surface grafted BPAM film was measured using an M-2000 spectroscopic ellipsometer (J.A. Woollam Co., Inc). Water contact angles were measured by a DSA 100 drop shape analysis system (KRÜSS) with a computer-controlled liquid dispensing system. Water droplets with a volume of 1 μL were used to measure the static contact angle. A fluorescent microscope (EVOS FL, Thermo-Scientific) equipped with a 100× objective was used for live/dead bacterial viability photomicrographs. A GFP FITC filter cube (excitation: 490 nm, emission: 503 nm) was used for SYTO® 9 and a Texas Red filter cube (excitation: 577 nm, emission: 620 nm) was used for the propidium iodide. The NO release study was performed using nitric oxide analyzer (NOA) 280i.

Synthesis of Bactericidal Agents and Fabrication of Polymeric Films

S-Nitroso-N-acetylpenicillamine (SNAP) synthesis—A method reported by Chipinda et al. was modified for synthesizing SNAP from NAP [61]. Briefly, sodium nitrite and NAP were added in an equimolar ratio to a 1:1 mixture of methanol and water containing 2 M $H_2SO_4$ and 2 M HCl. The mixture was stirred in the dark (to prevent NO release by light stimulation) for 40 min using a magnetic stirrer. Thereafter, the reaction vessel was placed in an ice bath to precipitate the SNAP crystals. The resulting crystals were filtered out of the solution and allowed to air dry in dark followed by vacuuming to remove traces of any solvent. SNAP crystals were stored in a freezer prior to use.

Benzophenone Based Antimicrobial Molecule (BPAM) Synthesis

The benzophenone based antimicrobial molecule (BPAM) was prepared using the previously reported procedure of Gao et al., [20]. Briefly, 4-methylbenzophenone (6.0 g, 30.6 mM), NBS (6.0 g, 33.6 mM), AIBN (1.0 g, 6.1 mM), and cyclohexane (100 mL) were added to a round-bottom flask under nitrogen atmosphere. The suspension was stirred under reflux overnight. After stirring, the mixture was cooled and filtered to remove any solid residues and the filtrate was concentrated under reduced pressure. The solid mixture was dissolved in diethyl ether and washed with water, brine and dried over magnesium sulfate. The mixture was filtered and concentrated under reduced pressure. The recovered solid was recrystallized from absolute ethanol to give fine white crystals. Yield: 7.1 g, 89%. $^1$H NMR: δ, 7.80 (t, 2H, J=3.0 Hz); 7.78 (t, 2H, J=1.4 Hz); 7.60 (t, 1H, J=7.0 Hz); 7.50 (d, 2H, 8.2 Hz); 7.49 (t, 2H, 7.6 Hz); 4.53 (s, 2H). $^{13}$C NMR ($CDCl_3$): δ, 195.93, 142.09, 137.39, 132.54, 130.52, 129.99, 128.92 128.33, 128.16, 32.25.

N-(4-benzoylbenzyl)-N,N-dimethylbutan-1-ammonium iodide (BPAM)

(4-bromomethyl) benzophenone (1.7 g, 6.2 mM), N,N-dimethyldodecylamine (1.7 mL, 6.2 mM), and tert-amyl alcohol (5 mL) were added to a sealable pressure flask. The mixture was stirred and heated in the sealed vessel at 95° C. for 24 h. The flask was cooled to room temperature and the solvent was removed under reduced pressure. The resulting brown waxy solid was recrystallized in hexane/ethyl acetate (7:4) to give a waxy white solid. Yield: 1.7 g, 67%. $^1$H NMR ($CDCl_3$): δ, 7.84 (dd, 4H, J=8.2, 23.9 Hz); 7.75 (d, 2H, J=7.0 Hz); 7.59 (t, 1H, J=7.6 Hz); 7.47 (t, 2H, 7.7 Hz); 3.57 (m, 2H); 3.35 (s, 6H); 1.80 (bs, 2H); 1.31 (bs, 4H); 1.21 (bs, 16H); 0.84 (t, 3H, J=6.6 Hz). $^{13}$C NMR ($CDCl_3$): δ, 210.33, 139.75, 136.70, 133.53, 133.24, 131.53, 130.54, 130.24, 120.66, 66.63, 64.12, 49.85, 32.06, 29.69, 29.58, 29.46, 29.37, 26.42, 22.82, 14.29.

Fabrication of Antimicrobial SNAP-CarboSil Polymer Films

To begin making the polymeric SNAP films, 70 mg/mL of CarboSil was dissolved in tetrahydrofuran (THF) as a solvent and stirred for 1 h at room temperature using a magnetic stirrer. After complete dissolution, 10% (w/w) of SNAP was quickly added and dissolved for 2 min in the Carbosil-THF solution. The SNAP films (10 wt %) were cast in Teflon molds (diameter=2.5 cm) and dried overnight in dark to prevent undesired loss of NO from the films using 3 ml of resulting SNAP-CarboSil-THF solution. The films were coated twice with 50 mg/ml CarboSil solution (in THF). This outer coating ensures that SNAP does not leach out from the films and also generates a smooth surface. The control CarboSil films were prepared and coated in a similar manner, without the addition of SNAP.

Surface Immobilization of BPAM on SNAP-CarboSil Films

Figure 9:
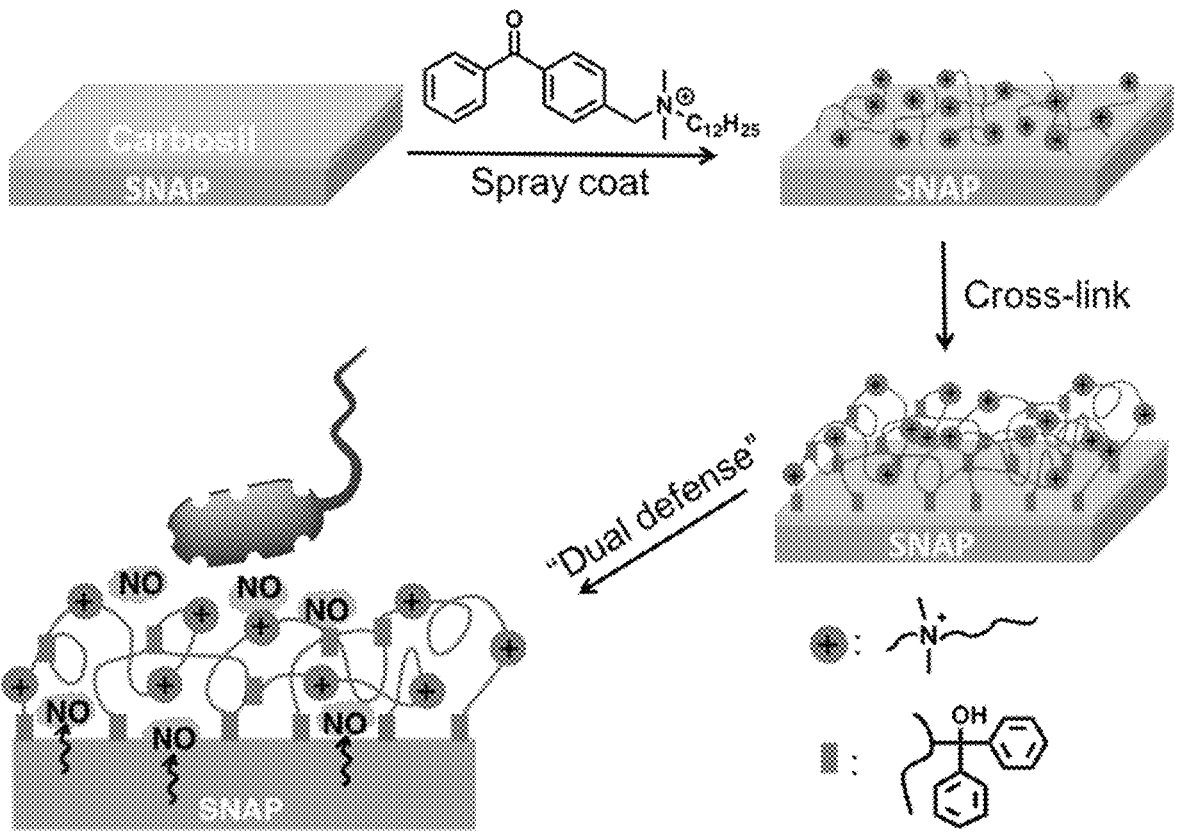
FIG. 9 shows the fabrication of the SNAP-BPAM CarboSil film and its biocidal action. Antibacterial polymeric composites were fabricated by incorporating a NO donor, S-nitroso-N-acetyl-penicillamine (SNAP) in CarboSil polymer and top coated with surface immobilized benzophenone based quaternary ammonium (BPAM) antimicrobial small molecule via photocrosslinking.

The BPAM film was immobilized onto SNAP-CarboSil film surfaces using spray coating. BPAM/isopropanol solution (5 mg/mL) was sprayed using an airbrush spray gun from a distance of 20 cm onto a vertically placed substrate to achieve uniform coating. Upon solvent evaporation, a thin film of BPAM remained on the surface. Then BPAM coated films were subsequently irradiated with UV light (254 nm, 6.5 mW/cm$^2$) for 2 min to covalently immobilize BPAM to the surface. The films were sonicated with isopropanol for 1 min to rinse off any residual, physisorbed BPAM and dried under a stream of nitrogen. FIG. 9 shows the fabrication procedure to make SNAP-BPAM CarboSil films (hereafter will be called SNAP-BPAM films).

Nitric Oxide Release Kinetics

Nitric oxide release from the SNAP and SNAP-BPAM films was measured using a Sievers Chemiluminescence Nitric Oxide Analyzer (NOA) 280i (Boulder, Colo.). The Sievers chemiluminescence NOA is considered as the gold standard for detecting in vitro nitric oxide release from the substrate. It is widely used for measurement of nitric oxide released from materials due to the ability to limit interfering species, such as nitrates and nitrites, as they are not transferred from the sample vessel to the reaction cell. Prior to NO release measurements, the films (n=3) were incubated for 1 h (PBS containing 100 mM EDTA, room temperature) to avoid the burst release associated with NO-releasing materials [42, 58]. Films were then placed in the sample vessel immersed in PBS (pH 7.4) containing 100 mM EDTA. Nitric oxide was continuously purged from the buffer and swept from the headspace using nitrogen sweep gas and a bubbler into the chemiluminescence detection chamber. Films were submerged in PBS with EDTA and stored in glass vials and kept at 37° C. between NO-release measurements. Fresh PBS solution was used for each NO-release measurement, and films were kept in fresh PBS solution for storage after each measurement.

UV-Vis Spectrophotometry

All UV-Vis spectra were recorded in the wavelength range of 200-700 nm using a UV-Vis spectrophotometer Cary Bio Spectrophotometer (Varian) at room temperature. CarboSil films and SNAP CarboSil films were developed on quartz glass substrates by spin coating with 200 μL of CarboSil/THF solution (50 mg/mL) at 1000 rpm for 30 s. BPAM was top coated on CarboSil/quartz substrates by spray coating with BPAM/IPA solution (10 mg/mL). The UV-vis spectrum of CarboSil was measured as the background. The presence of the S—NO group of SNAP provides characteristic absorbance maxima at 340 and 590 nm [42, 62]. CarboSil films were dissolved in DMAc and absorbance values were measured at 340 nm. The amount of SNAP was then determined using a calibration curve from known molar concentrations of SNAP in DMAC and compared to untreated control CarboSil films.

Quantification of Adhered and Viable Colony Forming Units on Polymeric Surface In the example, the ability of the CarboSil polymer with SNAP-BPAM combination to kill the adhered bacteria on the polymer surface was tested using the Gram-negative *Pseudomonas aeruginosa* and Gram-positive *Staphylococcus aureus* bacteria which are amongst the most common causes of hospital-acquired infections (HAIs). A modified protocol of standard bacterial adhesion tests was used to quantify the viable colony forming units of bacteria per surface area of the films (CFU/cm$^2$) [63-65]. A single colony of bacteria was isolated from a previously cultured LB-agar plate and incubated in LB medium for 14 h at 37° C. at a rotating speed of 150 rpm. The optical density of the culture was measured at a wavelength of 600 nm (O.D$_{600}$) using UV-vis spectrophotometer (Thermo scientific Genesys 10S UV-Vis) to ensure that bacteria is in log phase of their growth. The bacteria culture was then centrifuged at 3500 rpm for 7 min, the supernatant was discarded. And sterile phosphate buffer saline (PBS), pH 7.4 was added to the bacterial pellet. This procedure was repeated twice to remove all traces of LB medium and to suspend bacteria in PBS solution. In parallel, serial dilutions of the bacteria were prepared and plated in LB agar Petri dishes in order to verify the consistency of concentration of viable cells between experiments. The OD$_{600}$ of the cell suspension in PBS was measured and adjusted to the CFU/ml in the range of $10^7$-$10^9$ based on the standard calibration curve. CarboSil control, SNAP films, BPAM coated CarboSil films and SNAP-BPAM films (n=3; surface area=0.94 cm$^2$) were exposed to bacterial cells (CFU: $10^9$-$10^7$) at 37° C. for 24 h in a shaker incubator (150 rpm) after soaking them in PBS for 1 h to account for the burst effect. The 24 h incubation allows the bacteria to adhere to the surface of the films and the adhered bacteria were acted upon by BPAM and NO. After 24 h, films were removed from the solution and any loosely bound bacteria were washed by gently rinsing them with continuously flowing PBS (5 ml) using a pipette. The films were sonicated for 45 sec using an Omni-Tip homogenizer followed by vortexing for 30 sec to collect the bound bacteria in 2 ml PBS solution. The PBS solution with bacteria was serially diluted ($10^{-1}$-$10^{-5}$), plated in the solid LB agar medium and incubated for 20 h at 37° C. After 20 h, the CFUs of the adhered viable bacteria on the surface of the polymer were counted keeping in account the dilution factor.

Analysis of Residual NO Flux Post Bacteria Exposure

To ensure that fabricated film releases sufficient levels of nitric oxide after exposure to *Pseudomonas aeruginosa* or *Staphylococcus aureus* strain for 24 h (Example 2: Quantification of adhered and viable colony forming units on polymeric surface), the residual NO release was confirmed following the same procedure as explained in Example 2: Nitric Oxide release kinetics using the Sievers Nitric Oxide Analyzer (NOA). Triplicates of each film types (n=3) were analyzed for measuring the residual NO flux.

Zone of Inhibition (ZOI) Analysis

A standard agar diffusion protocol was followed to conduct zone of inhibition (ZOI) study to demonstrate the diffusive nature of NO molecule released from SNAP and SNAP-BPAM films in the surrounding agar. This study was designed to prove that the NO release from the polymeric composite can kill bacteria which are not in direct contact with the polymeric films which BPAM alone fails to achieve. As a proof of concept, Gram-positive *S. aureus* and Gram-negative *P. aeruginosa* bacteria strains were used for the study. A single colony of each bacterium was suspended individually in LB and incubated at 37° C. for 14 h at a rotating speed of 150 rpm. Using UV-Vis spectrophotometer (Genesis 10S-Thermo Scientific), the optical density (OD) of each of the bacterial cultures was measured at 600 nm (OD$_{600}$). The observed OD$_{600}$ was adjusted to 1×$10^7$ colony forming units per mL (CFUs/mL) based on a calibration curve based on the known concentration of *S. aureus* and *P. aeruginosa*. A sterile cotton swab was placed into each of the strain cultures and then gently pressed and rotated against pre-made LB-agar Petri dishes (14 cm) to spread the bacteria aseptically and uniformly. Circular disks (diameter: 22 mm) of control, SNAP, BPAM, and SNAP-BPAM films were placed on top of bacterial culture and pressed gently. The Petri dishes were incubated overnight at 37° C. in inverted position. The ZOI diameters were compared to evaluate the antimicrobial efficacy of NO releasing SNAP and SNAP-BPAM films.

Live/Dead Staining Assay

While the bacterial adhesion test allows counting the viable CFUs on the surface of the polymer, it doesn't provide any quantitative or qualitative information on how many cells were initially attached and died due to SNAP-BPAM biocidal activity. Using live/dead staining, we observed both live and dead bacteria cells that were bound to the surface of the polymer. This qualitative study was then combined with Cell Profiler software to quantify the live and dead bacteria on the polymeric surface. SYTO® 9 dye, yields green fluorescence and labels all bacteria in a population with intact membranes. In contrast, propidium iodide, which yields red fluorescence, penetrates only the bacteria with damaged membranes and replaces SYTO® 9 stains, causing a reduction in green fluorescence and the appearance of red fluorescence. Consequently, bacteria with damaged cell membranes can be distinguished from live bacteria. For each of the bacterial strains, 10 mL bacterial culture was grown to late log phase in broth (shaken at 100 rpm for 10 h at 37° C.). The culture was centrifuged at 4000 rpm for 10 min. The supernatant was removed and the pellet was suspended in sterile distilled water. Before staining, 10 µL bacterial suspension with a concentration around $10^8$ CFU/mL was placed on the CarboSil, BPAM coated CarboSil, SNAP-blended CarboSil, and SNAP-BPAM CarboSil films and dried at 37° C. for 5 min to achieve quick and intimate contact. Equal volumes of SYTO® 9 and propidium iodide (1.5 µL) were combined, added to 1 mL of distilled water, and mixed thoroughly. Diluted dye mixture (10 µL) was trapped between the slide with adhered bacteria and 18 mm square coverslip. The sample was incubated in dark for 15 min at room temperature and imaged qualitatively with an EVOS fluorescence microscope. Both the live and dead bacteria from the fluorescent images were then quantified with Cell Profiler software by randomly selecting different spots (n=3) on the films.

Statistical significance—For all the quantitative measurements n=3 data points were taken into consideration unless otherwise mentioned. Standard two-tailed t-test with unequal variance is used to do all statistical comparisons.

The data is reported as a mean±standard deviation and the significance with a p-value<0.05 is stated for comparisons.

Results

Photocrosslinking of BPAM on SNAP-CarboSil and Quantification of Total SNAP

Figure 10A:
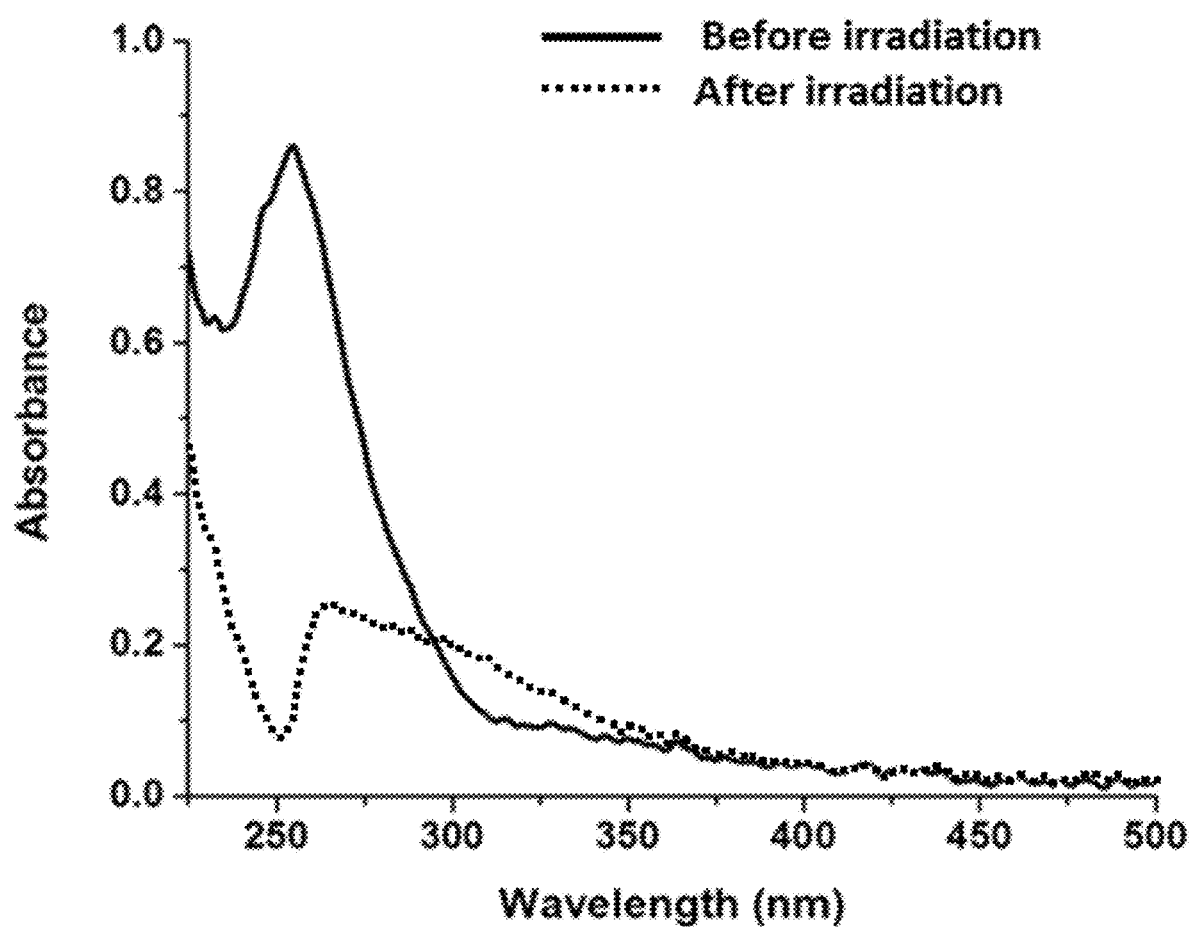
FIGS. 10A-10B show UV-mediated photocrosslinking study of BPAM on SNAP film.
Figure 10B:
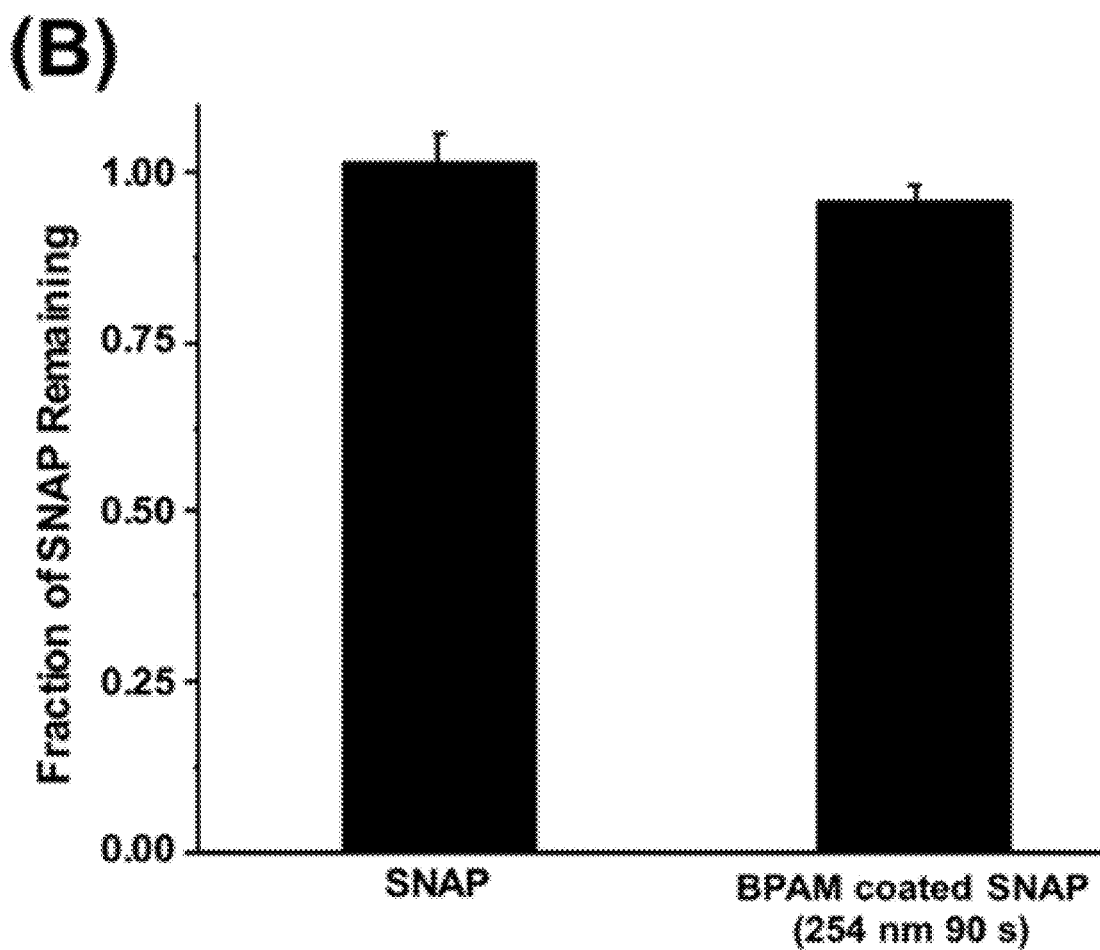

The benzophenone moiety of BPAM photochemically reacts with C—H groups of the CarboSil polymer to form new C—C bonds at the interface. Upon absorption of UV light, the promotion of one electron from a nonbinding n orbital to the antibonding $\pi^*$ orbital of the carbonyl group yields a biradicaloid triplet state where the electron-deficient oxygen n orbital interacts with surrounding weak C—H δ bonds, resulting in H abstraction to complete the half-filled n orbital. The two resulting carbon radicals then combine to form a new C—C bond. This process was monitored by the decrease in absorbance of the n-$\pi^*$ transition of BP using UV-vis spectrometry (FIG. 10A). Before exposure to UV light, the $\lambda_{max}$ absorbance at 255 nm was observed, which is the characteristic n-$\pi^*$ transition of BPAM [20]. A spectrum shoulder ranging from 310-350 nm is assigned to the UV absorbance ($\lambda_{max}$) of SNAP [61]. The low intensity of the SNAP absorbance is due to the low concentration of SNAP within the CarboSil polymer matrix. After UV irradiation for 90 seconds, absorbance at 255 nm decreased, indicating the completion of the crosslinking reaction. The broad shoulder at 250~300 nm could be due to slight photo-oxidation of the polycarbonate base [66]. The remaining SNAP content after UV treatment is shown in FIG. 10B and was confirmed to maintain 95.44±2.5% of the initial SNAP content. This can be mainly due to the presence of a top coat of Carbosil in the SNAP films before the application of BPAM. In the past, the application of top coats of CarboSil which are in the order of 100 microns has been shown to significantly reduce leaching when compared to non-top coated films [42]. These results confirmed that surface immobilized BPAM doesn't adversely cause significant loss of SNAP from the polymeric composite.

Nitric Oxide Release from SNAP and SNAP-BPAM CarboSil Films

Incorporation of SNAP to CarboSil has shown to provide continuous and localized NO delivery to specific sites of interest [67, 68]. The incorporation of SNAP in medical grade polymers have been shown to be hemocompatible and possesses stability during long-term storage at room temperature and physiological conditions [60, 69, 70].

Figure 11:
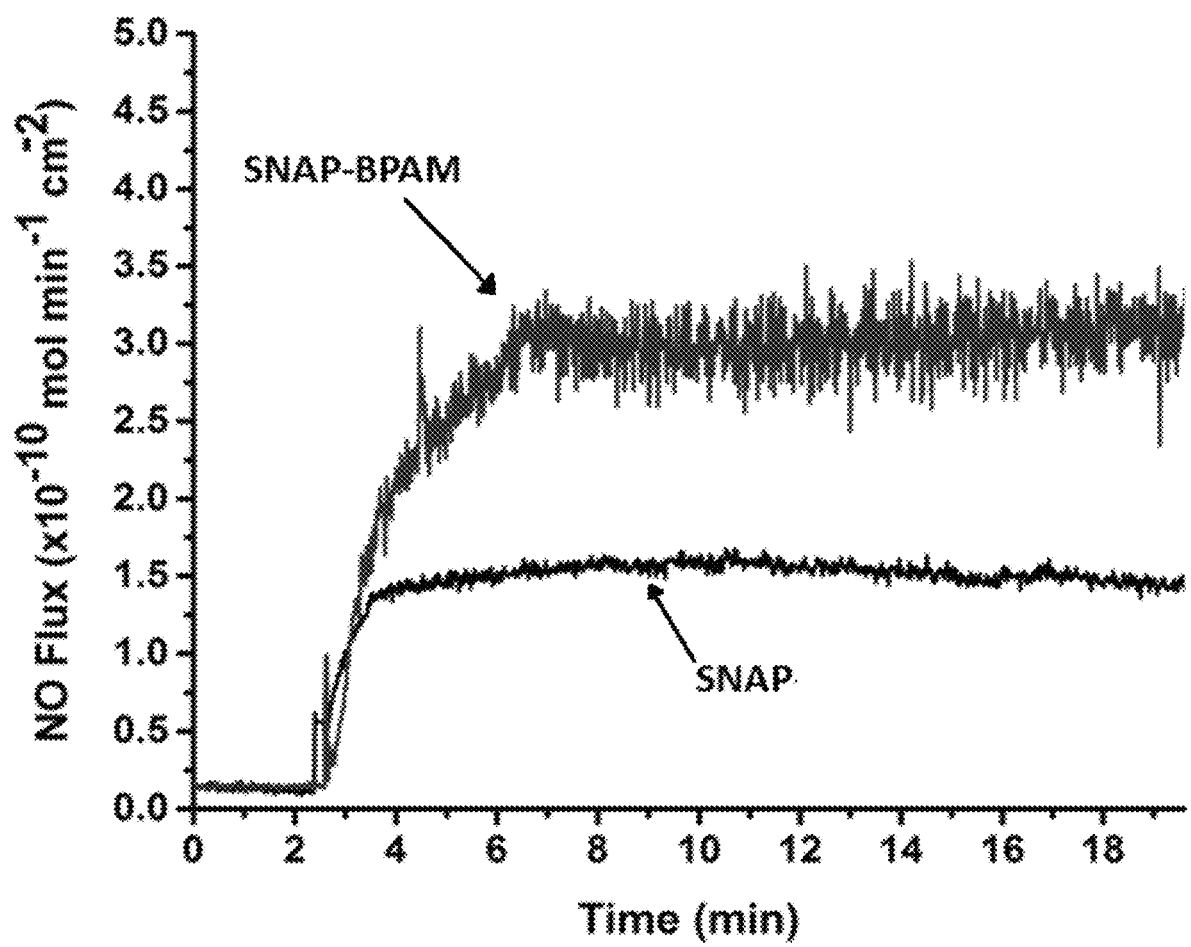
FIG. 11 shows real-time NO flux rate of SNAP doped CarboSil (black) and BPAM coated SNAP CarboSil films (red) analyzed at the physiological temperature using Sievers Nitric Oxide Analyzer (NOA).
Figure 12:
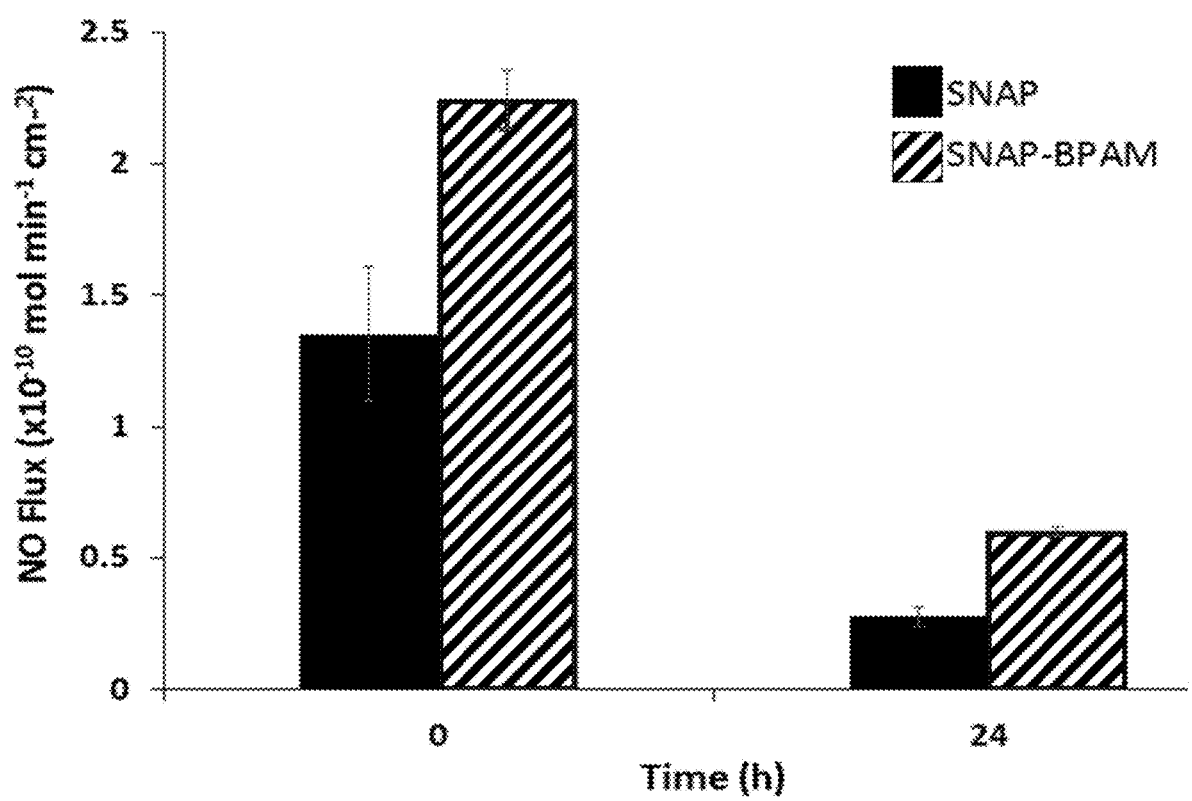
FIG. 12 shows nitric oxide (NO) flux analysis of SNAP and SNAP-BPAM films (at 0 h and 24 h time-period). The SNAP-BPAM films released higher NO flux at initially and at 24 h time point. The NO flux of SNAP-BPAM was maintained in the physiological range even after 24 h. The data is reported as a mean±standard deviation for n=3 samples and the significance with a p-value<0.05 is stated for comparisons.

In this study, release rates of NO were measured at physiological conditions (pH 7.4, 37° C.) to demonstrate that the presence of the BPAM coating does not adversely affect the NO release profile. The release of NO from these compounds stems from the breaking of the S—NO bond that can be catalyzed using heat, light, moisture, or metal ions [42, 57, 62]. Representative real-time NO release profiles from SNAP and SNAP-BPAM films was recorded via NOA as shown in FIG. 11. SNAP films exhibited an initial release rate of $1.35±0.11×10^{-10}$ mol min$^{-1}$ cm$^{-2}$ and release rate of $0.28±0.02×10^{-10}$ mol min$^{-1}$ cm$^{-2}$ after 24 h. SNAP films with BPAM top coat showed an increase in NO flux both at the initial ($2.58±0.25×10^{-10}$ mol min$^{-1}$ cm$^{-2}$) and at the 24-hour time point ($0.59±0.04×10^{-10}$ mol min$^{-1}$ cm$^{-2}$) (FIG. 12). This may be attributed to the increase in hydrophilicity of the films with the presence of BPAM topcoat as described above. The increased flux is still well within the physiological range ($0.5-4.0×10^{-10}$ mol min$^{-1}$ cm$^{-2}$) making it relevant and effective for biomedical device applications [39]. The NO flux exhibited by the films is sufficient to kill bacteria beyond 24 h. This has been shown in vivo in a 7-day sheep catheter model using similar hydrophobic polymers with 10 wt. % SNAP [71]. These materials exhibit similar NO release characteristics over a 28-d period and demonstrate that NO release rates at the lower end of physiological limits are still effective in providing antibacterial activity. Another report has also shown that hydrophobic polymers with SNAP have extended NO-release at physiological levels (up to 20 days) [67]. Furthermore, the incorporation of SNAP in medical grade polymers are not only hemocompatible and biocompatible but also stable during long-term storage (6 months) at room temperature and physiological conditions [60, 69, 70].

Coating Thickness and Contact Angle Analysis

The thickness and static contact angle measurements are among the most relevant physical characterization for a polymeric coating. The results of this characterization for CarboSil films functionalized with individual and combination of antibacterial agents are illustrated in Table 3.1. The thickness of the crosslinked BPAM coatings on CarboSil and SNAP CarboSil films after UV irradiation were 45.7±0.3 nm and 47.9±0.5 nm, respectively, indicating successful grafting of a BPAM coating. Water contact angles of control CarboSil, SNAP CarboSil, BPAM CarboSil, and SNAP-BPAM CarboSil surfaces are also listed in Table 1. We have previously shown that blending SNAP into the CarboSil polymeric matrix does not affect the hydrophobicity of the polymer [68]. The study showed that due to lower water uptake of CarboSil, limited leaching of SNAP has been seen from SNAP doped CarboSil. Leaching is further reduced with the use of a top coat (<10% of total SNAP loading in first 24 h) as compared to the non-coated films. A change in the topcoat of Carbosil is much thicker than photo-crosslinked BPAM coat (100 μm vs 50 nm for BPAM) and hence little or no changes to the leaching kinetics of SNAP is expected.

TABLE 2

Physical properties of antibacterial SNAP-BPAM film

| Sample | CarboSil | SNAP CarboSil | BPAM CarboSil | SNAP-BPAM CarboSil |
|---|---|---|---|---|
| Thickness (nm) | N/A | N/A | 45.7 ± 0.3 | 47.9 ± 0.5 |
| Contact Angle (°) | 119.3 ± 0.4 | 115 ± 0.2 | 67.9 ± 0.6 | 63.5 ± 0.5 |

The data is reported as a mean ± standard deviation for n = 3 samples and the significance with a p-value < 0.05 is stated for comparisons.

Blending SNAP into the CarboSil polymeric matrix does not affect the hydrophobicity of the polymer. The CarboSil control surface was found to be hydrophobic with contact angle (CA) of 119.3±0.4°. The surface grafted layer of BPAM significantly decreases the hydrophobicity of the CarboSil based polymer film, reducing the CA to 63.5°±0.5°, resulting from the positively charged ammonium functional groups. The increase in the surface hydrophilicity is expected to increase the antibacterial efficacy of the SNAP-BPAM polymer films as studies have shown a marked increase in NO release from the hydrophilic surface when compared to the hydrophobic surfaces [42]. This is in line with the results obtained from the NO release kinetics study. Furthermore, increased hydrophilicity helps in the repulsion of non-specific protein adsorption, and ultimately bacterial adhesion [72, 73] as confirmed by the bacterial adhesion test and Live/Dead staining.

Quantification of Adhered Viable Bacteria (CFU/Cm$^2$)

Figure 13:
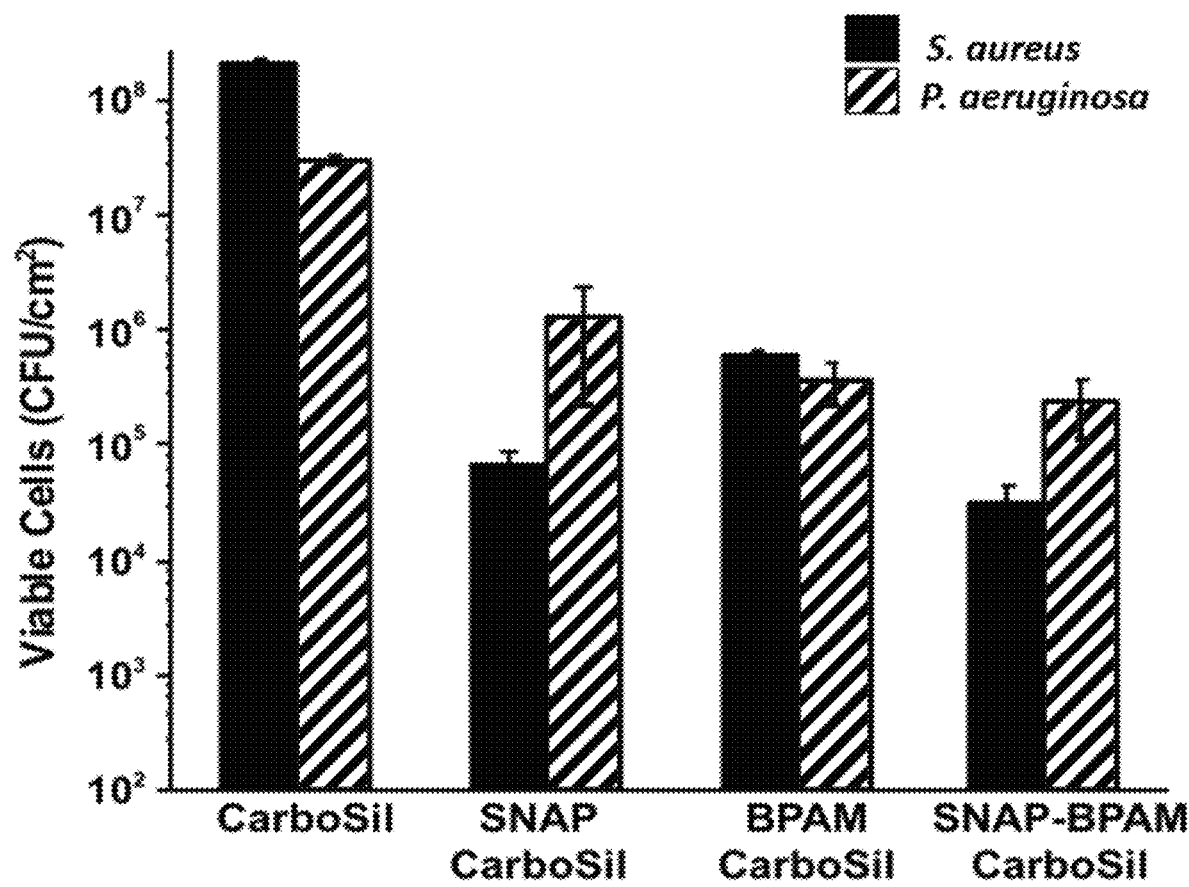
FIG. 13 shows comparative graphs to show the differences in inhibition of viable colony forming units of Gram-positive S. aureus and Gram-negative P. aeruginosa on the unit surface area (CFU/cm$^2$) of SNAP films, BPAM films and SNAP-BPAM films as compared to control CarboSil. The results suggest that both SNAP and BPAM has different degree of toxicity towards gram positive and negative bacteria. While BPAM by itself has better antibacterial potential towards gram negative P. aeruginosa as compared to SNAP, SNAP is better than BPAM w.r.t its bactericidal action against gram positive S. aureus. The combined action of SNAP-BPAM works equally well against both the bacteria. The data is reported as a mean±standard deviation for n=3 samples and the significance with a p-value<0.05 is stated for comparisons.

Biofilm formation is a major cause of morbidity and mortality associated with hospital acquired infection (HAIs). *Staphylococcus aureus*, a Gram-positive bacterium, and *Pseudomonas aeruginosa*, a Gram-negative bacterium are among the most common causes of nosocomial bloodstream infections that can form embedded biofilm matrices on indwelling biomedical devices [74-76]. As shown in FIG. 13, the amount of viable *P. aeruginosa* and *S. aureus* adhered on SNAP-BPAM film surfaces are significantly lower than that of control films. While BPAM and SNAP are excellent antimicrobial agents, the combination offers several advantages not possessed by an individual antimicrobial agent. BPAM by itself has a superior antibacterial potential towards Gram-negative *P. aeruginosa* as compared to SNAP, and SNAP is superior with respect to its bactericidal action against Gram-positive *S. aureus*. The combination is very effective against both Gram-positive and negative bacteria. Overall the SNAP-BPAM films reduced the adhered viable bacteria (both Grams positive and negative) to the maximum extent as compared to the control films. SNAP-BPAM films showed a 4-log reduction for Gram-positive *S. aureus* and 3-log reduction for Gram-negative as compared to the CarboSil control. FIG. 13 and Table 3 represents the graphs and the raw data for the reduction in adhered CFU of both the bacteria per surface area of the polymeric composites. The difference in the results between the two bacteria can be attributed to the difference in the cell wall and membrane composition of Gram-positive and Gram-negative bacteria [77].

BPAM films have relatively higher hydrophilicity (due to BPAM coat) than SNAP films alone which increased the NO flux release from the SNAP-BPAM films.

The residual NO analysis after exposing films to bacteria suspension (FIG. 14) showed an abundance of NO up to $0.92 \pm 0.05 \times 10^{-10}$ mol min$^{-1}$ cm$^{-2}$ flux, suggesting that these films can continue to exhibit antibacterial properties beyond 24 h. The combined action of these bactericidal agents via multiple mechanisms of bacteria killing warrants a significant reduction in viable bacterial load for both Gram-positive and negative strains.

Bacterial Killing Via NO Diffusion

While BPAM is an excellent antimicrobial agent, due to its non-diffusive nature, it cannot kill the bacteria protected within the biofilm matrix. Moreover, the charge density of surface-bound BPAM might be neutralized with anionic cellular components in the cytoplasm that is expelled out of the dead bacteria or screened by the layer of negatively charged dead bacterial cells covering the material's surface [26, 27]. Therefore, the diffusive nature of NO can be beneficial in biofilm eradication beyond the close vicinity of the material. The standard agar diffusion test allowed us to show the bactericidal effect of the NO releasing films in the presence and absence of the BPAM.

Figures 15A, 15B:
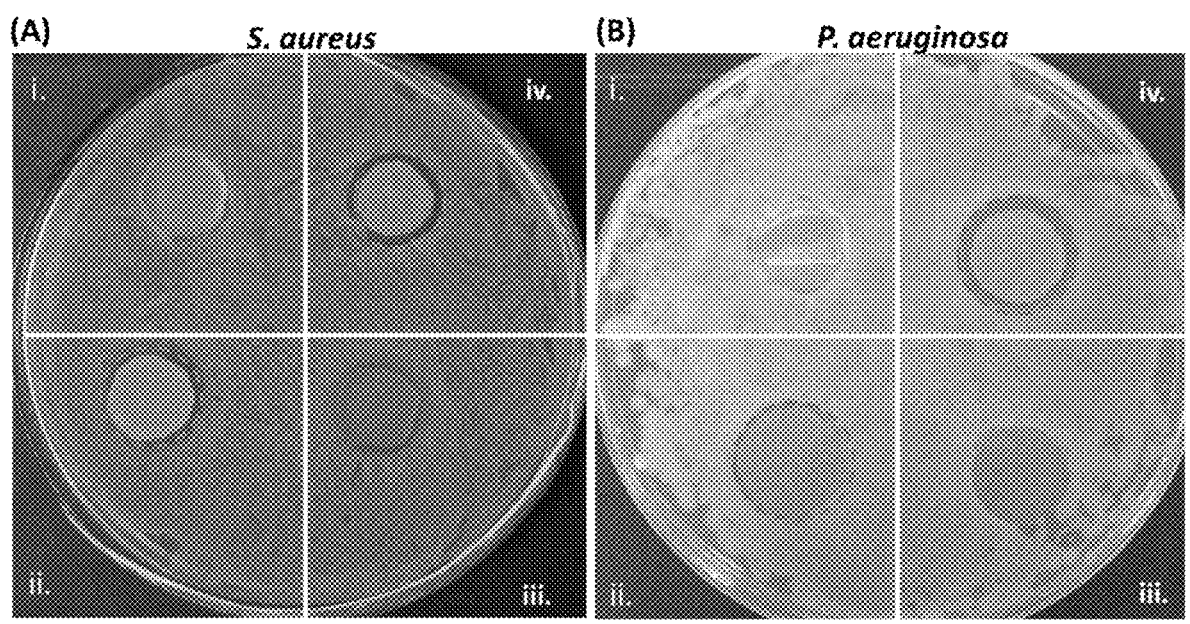
FIGS. 15A-15B show the zone of inhibition (ZOI) can be seen inside the dotted red circle.

The CarboSil films with incorporated antimicrobial agents (SNAP-BPAM) and their combination resulted in a zone of inhibition (ZOI) of different diameters when exposed to LB agar plates with bacterial culture. As expected, the result demonstrated that BPAM has no ZOI, while the SNAP films and SNAP-BPAM films showed a clear ZOI due to the release of NO gas from SNAP when placed in an incubator at 37° C. for 20 h (FIGS. 15A-B). The explanation for this is the diffusive nature of NO that can

TABLE 3

A comparative viable bacterial adhesion data for polymeric composites and NO flux analysis before and after bacterial exposure

| Films | NO flux* (0 h) | NO flux* (24 h) | S. aureus CFU/cm$^2$ | P. aeruginosa CFU/cm$^2$ | Residual NO flux* Post S.A | Residual NO flux* Post P.A |
|---|---|---|---|---|---|---|
| Carbosil | | | $2.1 \times 10^8 \pm 7.3 \times 10^6$ | $3.0 \times 10^8 \pm 9.7 \times 10^5$ | — | |
| BPAM | | | $6.0 \times 10^5 \pm 5.9 \times 10^4$ | $3.8 \times 10^5 \pm 6.2 \times 10^4$ | — | |
| SNAP | $1.35 \pm 0.11$ | $0.28 \pm 0.02$ | $6.6 \times 10^4 \pm 2.0 \times 10^4$ | $1.3 \times 10^6 \pm 5.9 \times 10^5$ | $0.19 \pm 0.07$ | $0.30 \pm 0.12$ |
| SNAP-BPAM | $2.21 \pm 0.25$ | $0.35 \pm 0.04$ | $3.0 \times 10^4 \pm 7.0 \times 10^3$ | $2.3 \times 10^5 \pm 8.3 \times 10^4$ | $0.70 \pm 0.32$ | $0.92 \pm 0.06$ |

*NO flux ($\times 10^{-10}$ mol min$^{-1}$ cm$^{-2}$).
The data is reported as a mean ± standard deviation for n = 3 samples and the significance with a p-value < 0.05 is stated for comparisons.
Post S.A means NO flux after 24 hours of *S. aureus* exposure and post P.A means NO flux after 24 hours of *P. aeruginosa* exposure.

Non-leaching BPAM can only act on bacteria in intimate contact while NO can act beyond direct point of contact because of diffusion. The activity of BPAM is also diminished with time by the layer of bacterial cells (live or dead) on polymeric composites as they tend to neutralize the charge on quaternary ammonium. This problem can be addressed by the application of NO. The small molecular size of NO allows it to diffuse through the bacterial biofilm and kill the bacterial cells which are otherwise resistant to bactericidal agents. In other words, the gradually released NO extended the life of BPAM by lowering the concentration of surrounding bacteria near the surface. The SNAP-penetrate in the LB agar and hence prevent the bacterial growth in the area around the film. The breaking of the S—NO bond in SNAP causes the release of NO. On the other hand, BPAM is non-diffusive in nature and hence can only act on bacteria which are in direct contact. From an application point of view, this will be beneficial for biofilm eradication as NO due to its small size would easily penetrate through the matrix of a bacterial biofilm. Even though BPAM didn't show any ZOI, it did prevent the growth of bacteria in direct contact underneath the film. The ZOI for *P. aeruginosa* was observed to be 24 mm for SNAP films and 26 mm for SNAP-BPAM films. Similarly, the ZOI for *S.* aureus was observed to be 24 mm with SNAP films and 25 mm for SNAP-BPAM films. Overall SNAP-BPAM composites showed the largest ZOI for both *S. aureus* as well as *P. aeruginosa* strains among all the composites. The bigger ZOI with SNAP-BPAM combination is due to increase in NO flux with BPAM topcoat ($1.35\pm0.11\times10^{-10}$ in SNAP films vs $2.58\pm0.25\times10^{-10}$ mol min$^{-1}$ cm$^{-2}$ in SNAP-BPAM films) as observed by chemiluminescence NOA. FIGS. 15A-B show the comparative ZOI diameter among the films for both the bacterial strains. The difference in antibacterial efficacy shown towards the two bacterial strains can be attributed to the membrane properties of Gram-positive and Gram-negative bacteria [77].

Analysis and Quantitation of Live/Dead Stain Test on CarboSil Films

As mentioned above, the bacterial adhesion test showed the reduction in adhered viable cells and zone of inhibition agar diffusion test demonstrated the killing of bacteria through diffusion respectively. However, the relative number of live and dead bacteria on the films were not evaluated by either of these tests. Therefore, the antibacterial activity of the SNAP-BPAM hybrid CarboSil films was also evaluated using a live/dead fluorescent stain assay which stains the live cells as green and the dead cells as red. Fluorescent images of *S. aureus* cells were exposed on control CarboSil, BPAM, SNAP, and SNAP-BPAM films. The bacterial cell count for the live/dead assay was quantitatively estimated at three randomly selected spots by using Cell Profiler software as recommended by published reports [78, 79]. On the control films, 97.35±0.72% bacterial cells showed green fluorescence, evenly distributed across the surface, and retained intact spherical shape, suggesting that the tested bacterial cells were viable. On BPAM coated CarboSil films, 94.41±0.61% of the total bacterial cells were stained red, indicating the cell membrane disruption caused by contact with surface-bound quaternary ammonium. On SNAP films, 97.58±0.44% of the total bacteria showed red fluorescence indicating dead cells. In the case of SNAP-BPAM CarboSil films, a 99.62±0.59% killing efficacy was achieved, demonstrating that the hybrid method effectively enhances the antibacterial activity of the functionalized biocompatible polymer material. This enhancement in bactericidal activity of SNAP-BPAM as compared to SNAP and BPAM films is in line with the viable bacteria adhesion test as well as the zone of inhibition testing. Notably, the pattern of aggregation of bacterial cells on the surface of the film was observed to be different and dependent on the antibacterial agent. The bacterial cells on control CarboSil and BPAM films have a regular pattern of bacterial cell distribution. On the other hand, the cells were aggregated together on SNAP Carbosil films, possibly due to the hydrophobicity of the CarboSil surface which caused repulsion to the negatively charged bacterial cells. On the SNAP-BPAM films, the dead cells dispersed across the surface which might be due to the relatively lower hydrophobicity (C.A=63.5°±0.5°) of the SNAP-BPAM films' surface as compared to SNAP films (C.A=115°±0.2°) resulting from the positively charged ammonium functional groups. Overall, lived/dead staining experiment combined with Cell Profiler software further validated that combined NO and surface-bound quaternary ammonium can provide dual antibacterial activities and thus significantly enhance the biocidal activity as compared to the individual agent. The authors suggest further in vitro testing and high resolution image analysis on bacterial aggregation pattern to validate this plausible theoretical explanation.

Discussion

In the present example, a NO donor molecule (SNAP) and a surface immobilized benzophenone based antimicrobial molecule (BPAM) were used in combination and their combined effect to reduce microbial adhesion and viability on a medical grade polymeric surface was evaluated. Since the $\lambda_{max}$ of BPAM and SNAP are distinctly separated, this benefits the hybrid material in two ways: (1) BPAM can absorb photons efficiently for the photoreaction even in the presence of SNAP; (2) Photo-degradation of SNAP is limited in the cross-linking process since the irradiation wavelength is 254 nm for the maximum energy absorbance efficiency of BPAM.

The antibacterial potential of SNAP-BPAM films was tested via (i) Bacterial Adhesion test (ii) Agar diffusion test (iii) Live/Dead staining. Combined these three tests allowed to quantitatively assess the bacterial adhesion (both viable and non-viable) and their subsequent killing by NO and BPAM action. The antimicrobial properties of NO are due to denaturation of enzymes, deamination of DNA and lipid oxidation in bacteria matrix [52]. On the other hand, BPAM kills the bacteria that are in direct contact by damaging the bacterial cell membrane integrity due to electrostatic interactions [21, 22].

SNAP based NO releasing polymers have many desirable properties from a translational perspective such as the long-term storage stability (6 months), ease of sterilization, and extended NO release (>2 weeks) without negatively affecting the physical characteristics, biocompatibility, and hemocompatibility of the polymer [42, 59, 60]. Similarly, the surface grafted BPAM has been reported to exhibit excellent antimicrobial activity against Gram-positive and Gram-negative bacteria on instant contact due to high surface charge density of the deposited BPAM thin film [20]. However, this is the first example that combines SNAP and BPAM together to demonstrate their antibacterial potential.

The present example demonstrated that the SNAP-BPAM combination has better antibacterial properties than SNAP or BPAM alone. BPAM is highly regarded as a bactericidal agent, but, it can only act on bacteria that are in direct contact. NO molecule through its diffusive nature allows acting on bacteria that are beyond the direct contact. This property is useful to act on biofilm matrix that otherwise prevents the penetration of antibacterial agent and keeps the bacteria immune. BPAM however, imparts a relatively hydrophilic surface to SNAP-CarboSil as apparent from a decrease in the contact angle. Studies have shown higher NO release from the hydrophilic surface when compared to the hydrophobic surfaces which in turn resulted in higher bacterial killing [42]. This is in line with the NO flux analysis as the SNAP-BPAM films showed higher NO flux as compared to the SNAP films. Furthermore, a hydrophilic surface helps in the repulsion of non-specific protein adsorption, and ultimately bacterial adhesion [72, 73] as confirmed by the bacterial adhesion test and Live/Dead staining. From a translational perspective, a biomedical implant fabricated with a non-leaching, hydrophilic surface would be able to form a solvated, aqueous layer upon contact with body fluids and thus reduce bacterial adhesion [80]. In addition, NO also has the advantage in blood-contacting device applications of the localized effect of temporarily inhibiting the activation of platelets that approach the polymer surface [56].

Figure 14:
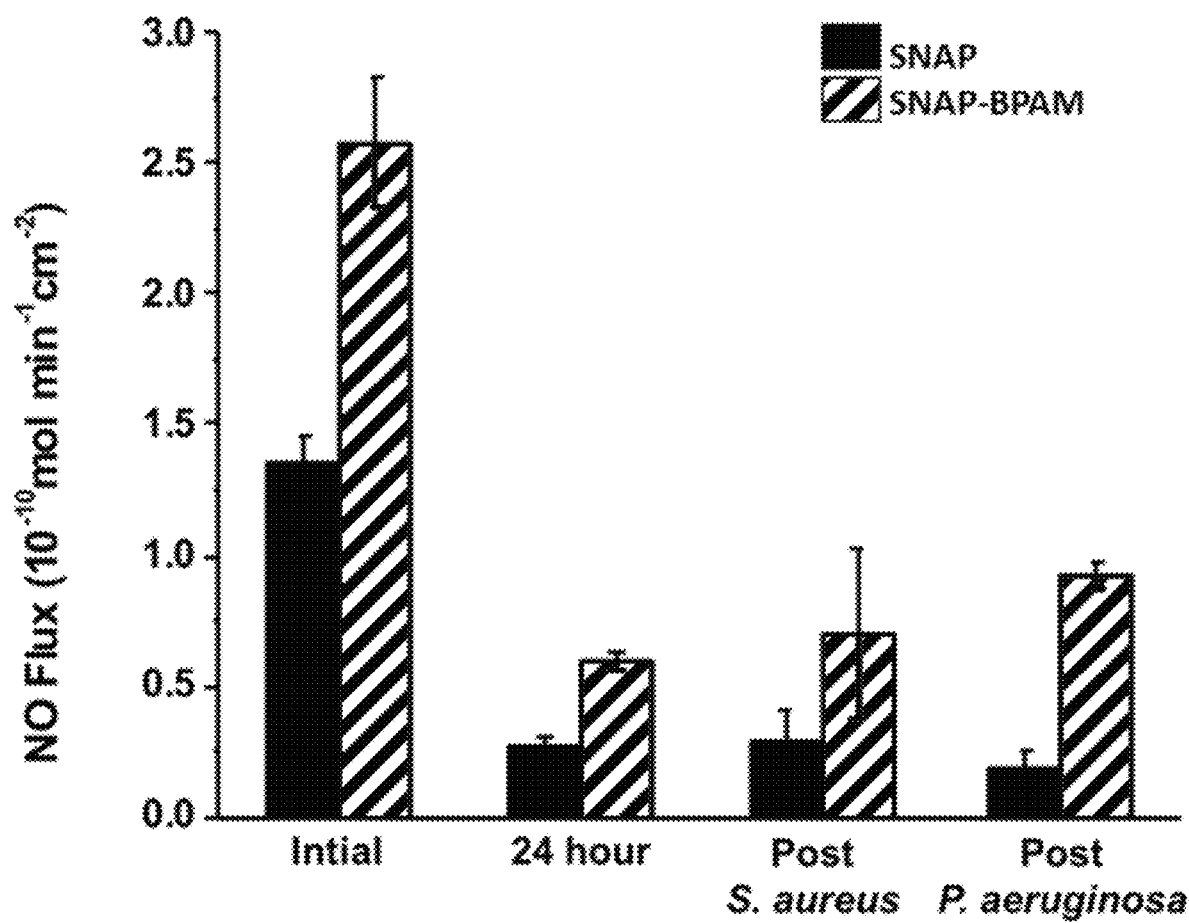
FIG. 14 shows the effect of immobilized BPAM top coats on NO release kinetics of the SNAP-BPAM films as measured by chemiluminescence before (0 h and 24 h) and after bacterial exposure (24 h) study. The residual NO flux was observed to be in the physiological range even after 24 h of bacteria exposure indicating the antibacterial effect can be extended beyond the 24 h. The data is reported as a mean±standard deviation for n=3 samples and the significance with a p-value<0.05 is stated for comparisons.

In vitro characterization of the SNAP-BPAM containing CarboSil polymer in the present example showed that such polymeric composites can yield better antibacterial effect as compared to SNAP or BPAM individually (FIGS. 14, 15A-15B). Their distinct but very effective mode of bactericidal action assures that the bacteria that in contact with the polymeric composites are attacked via multiple bactericidal mechanisms. The NO release with the SNAP-BPAM combination was shown to be higher than with SNAP alone making their cooperation more effective in terms of diffusion of NO into the biofilm (FIGS. 11 and 12). These SNAP-BPAM-CarboSil composites continued to release NO flux in the physiological range past the bacteria exposure for 24 h (FIG. 14). The sustained release of diffusible NO also extended the duration of localized action of BPAM by lowering the concentration of surrounding viable bacteria near the polymer surface allowing BPAM to kill any bacteria in local contact.

Overall, the combined action of these bactericidal agents via distinct mechanisms warrants a significant reduction in viable bacterial load for both Gram-positive and negative strains. Furthermore, the rapid action of NO (half-life<5 sec) and non-specific lethal action of surface-bound BPAM via physical membrane disruption limit the development of resistant bacterial strains [47, 51, 53-55].

Conclusion

In the current example, a polymeric composite was fabricated by blending SNAP in the CarboSil polymer and BPAM was surface grafted via UV photocrosslinking and its ability to inhibit bacteria on the surface was tested both qualitatively and quantitatively. The SNAP-BPAM combination was more effective in maximizing the bacterial load on the surface of the polymeric composite as compared to SNAP or BPAM films individually. The bacterial adhesion test demonstrated that combination is equally effective in minimizing the adhered viable CFUs of both Gram-positive and Gram-negative bacteria whereas SNAP was more effective against *S. aureus* and BPAM alone was more effective against *P. aeruginosa* when tested alone. As demonstrated by the agar diffusion test diffusive nature of NO allowed to kill the bacteria beyond the direct point of contact which BPAM can't achieve alone. This is important for potential application in biofilm eradication. The live/dead staining allowed to observe that SNAP-BPAM combination has a higher number of attached dead bacteria (than live) as compared to the controls. BPAM coat also increased the hydrophilicity and higher NO flux as compared to the SNAP films. In addition, NO based material can be used in blood-contacting device applications because it temporarily inhibits the activation of platelets on the polymer's surface which BPAM cannot [56]. Overall, all these characteristics are ideal for controlling biomedical device related infections, especially in preventing bacteria from developing antibiotic resistance due to the different killing mechanisms exhibited by SNAP and BPAM. Such highly effective antimicrobial attributes offer a new paradigm in the fabrication of antimicrobial surfaces for various medical device applications.

References for Example 2

1. W. E. STAMM, Infections related to medical devices, Annals of Internal Medicine 89(5_Part_2) (1978) 764-769.
2. E. J. Brisbois, M. Kim, X. Wang, A. Mohammed, T. C. Major, J. Wu, J. Brownstein, C. Xi, H. Handa, R. H. Bartlett, Improved Hemocompatibility of Multilumen Catheters via Nitric Oxide (NO) Release from S-Nitroso-N-acetylpenicillamine (SNAP) Composite Filled Lumen, ACS Appl. Mater. Interfaces 8(43) (2016) 29270-29279.
3. J. W. Warren, Catheter-associated urinary tract infections, Infectious disease clinics of North America 11(3) (1997) 609-622.
4. P. S. Stewart, J. W. Costerton, Antibiotic resistance of bacteria in biofilms, The lancet 358(9276) (2001) 135-138.
5. Y.-H. Lee, F.-Y. Cheng, H.-W. Chiu, J.-C. Tsai, C.-Y. Fang, C.-W. Chen, Y.-J. Wang, Cytotoxicity, oxidative stress, apoptosis and the autophagic effects of silver nanoparticles in mouse embryonic fibroblasts, Biomaterials 35(16) (2014) 4706-4715.
6. E.-J. Park, J. Yi, Y. Kim, K. Choi, K. Park, Silver nanoparticles induce cytotoxicity by a Trojan-horse type mechanism, Toxicol. In Vitro 24(3) (2010) 872-878.
7. P. AshaRani, G. Low Kah Mun, M. P. Hande, S. Valiyaveettil, Cytotoxicity and genotoxicity of silver nanoparticles in human cells, ACS nano 3(2) (2008) 279-290.
8. I. Raad, R. Darouiche, R. Hachem, M. Sacilowski, G. P. Bodey, Antibiotics and prevention of microbial colonization of catheters, Antimicrobial agents and chemotherapy 39(11) (1995) 2397-2400.
9. K. K. Jefferson, D. A. Goldmann, G. B. Pier, Use of confocal microscopy to analyze the rate of vancomycin penetration through *Staphylococcus aureus* biofilms, Antimicrobial agents and chemotherapy 49(6) (2005) 2467-2473.
10. J. Yatvin, J. Gao, J. Locklin, Durable Defense: Robust and Varied Attachment of Non-leaching Poly"-Onium" Bactericidal Coatings to Reactive and Inert Surfaces, Chemical Communications 50(67) (2014) 9433-9442.
11. N. M. Milović, J. Wang, K. Lewis, A. M. Klibanov, Immobilized N-Alkylated Polyethylenimine Avidly Kills Bacteria by Rupturing Cell Membranes with No Resistance Developed, Biotechnology and Bioengineering 90(6) (2005) 715-722.
12. I. Yudovin-Farber, N. Beyth, A. Nyska, E. I. Weiss, J. Golenser, A. J. Domb, Surface Characterization and Biocompatibility of Restorative Resin Containing Nanoparticles, Biomacromolecules 9(11) (2008) 3044-3050.
13. S. A. Koplin, S. Lin, T. Domanski, Evaluation of the Antimicrobial Activity of Cationic Polyethylenimines on Dry surfaces, Biotechnology Progress 24(5) (2008) 1160-1165.
14. L. Ferreira, A. Zumbuehl, Non-leaching Surfaces Capable of Killing Microorganisms on Contact, Journal of Materials Chemistry 19(42) (2009) 7796-7806.
15. D. Park, J. Wang, A. M. Klibanov, One-Step, Painting-Like Coating Procedures To Make Surfaces Highly and Permanently Bactericidal, Biotechnology Progress 22(2) (2006) 584-589.
16. Y. Xie, C. A. S. Hill, Z. Xiao, H. Militz, C. Mai, Silane coupling agents used for natural fiber/polymer composites: A review, Composites Part A: Applied Science and Manufacturing 41(7) (2010) 806-819.
17. S. J. Yuan, S. O. Pehkonen, Y. P. Ting, K. G. Neoh, E. T. Kang, Inorganic-Organic Hybrid Coatings on Stainless Steel by Layer-by-Layer Deposition and Surface-Initiated Atom-Transfer-Radical Polymerization for Combating Biocorrosion, ACS Applied Materials & Interfaces 1(3) (2009) 640-652.
18. J. J. Locklin, US patent, 2013.
19. V. P. Dhende, S. Samanta, D. M. Jones, I. R. Hardin, J. Locklin, One-Step Photochemical Synthesis of Permanent, Nonleaching, Ultrathin Antimicrobial Coatings for Textiles and Plastics, ACS Applied Materials & Interfaces 3(8) (2011) 2830-2837.
20. J. Gao, N. E. Huddleston, E. M. White, J. Pant, H. Handa, J. Locklin, Surface Grafted Antimicrobial Polymer Networks with High Abrasion Resistance, ACS Biomaterials Science & Engineering (2016).
21. R. Kügler, O. Bouloussa, F. Rondelez, Evidence of A Charge-Density Threshold for Optimum Efficiency of Biocidal Cationic Surfaces, Microbiology 151(5) (2005) 1341-1348.
22. A. L. Sonenshein, J. A. Hoch, R. Losick, *Bacillus subtilis* and Other Gram-positive Bacteria: Biochemistry, Physiology, and Molecular Genetics, American Society for Microbiology 1993.
23. K. Lewis, A. M. Klibanov, Surpassing Nature: Rational Design of Sterile-Surface Materials, Trends in Biotechnology 23(7) (2005) 343-348.
24. J. C. Tiller, Antimicrobial Surfaces, in: H. G. Borner, J. F. Lutz (Eds.), Bioactive Surfaces 2011, pp. 193-217.
25. A. M. Bieser, J. C. Tiller, Mechanistic Considerations on Contact-Active Antimicrobial Surfaces with Controlled Functional Group Densities, Macromolecular bioscience 11(4) (2011) 526-534.
26. A. M. Bieser, J. C. Tiller, Mechanistic Considerations on Contact-Active Antimicrobial Surfaces with Controlled Functional Group Densities, Macromolecular Bioscience 11(4) (2011) 526-534.
27. S. B. Lee, R. R. Koepsel, S. W. Morley, K. Matyjaszewski, Y. Sun, A. J. Russell, Permanent, Nonleaching Antibacterial Surfaces. 1. Synthesis by Atom Transfer Radical Polymerization, Biomacromolecules 5(3) (2004) 877-882.
28. B. J. Nablo, H. L. Prichard, R. D. Butler, B. Klitzman, M. H. Schoenfisch, Inhibition of implant-associated infections via nitric oxide release, Biomaterials 26(34) (2005) 6984-6990.
29. A. W. Carpenter, M. H. Schoenfisch, Nitric oxide release: Part II. Therapeutic applications, Chem. Soc. Rev. 41(10) (2012) 3742-3752.
30. A. W. Carpenter, B. V. Worley, D. L. Slomberg, M. H. Schoenfisch, Dual action antimicrobials: nitric oxide release from quaternary ammonium-functionalized silica nanoparticles, Biomacromolecules 13(10) (2012) 3334-3342.
31. B. V. Worley, D. L. Slomberg, M. H. Schoenfisch, Nitric oxide-releasing quaternary ammonium-modified poly (amidoamine) dendrimers as dual action antibacterial agents, Bioconj. Chem. 25(5) (2014) 918-927.
32. B. V. Worley, K. M. Schilly, M. H. Schoenfisch, Antibiofilm efficacy of dual-action nitric oxide-releasing alkyl chain modified poly (amidoamine) dendrimers, Mol. Pharm. 12(5) (2015) 1573-1583.
33. Y. Hou, A. Janczuk, P. Wang, Current trends in the development of nitric oxide donors, Current Pharmaceutical Design 5(6) (1999) 417-442.
34. Y. Vodovotz, C. Bogdan, J. Paik, Q. Xie, C. Nathan, Mechanisms of suppression of macrophage nitric oxide release by transforming growth factor beta, The Journal of experimental medicine 178(2) (1993) 605-613.
35. J. B. Hibbs, R. R. Taintor, Z. Vavrin, E. M. Rachlin, Nitric oxide: a cytotoxic activated macrophage effector molecule, Biochem. Biophys. Res. Commun. 157(1) (1988) 87-94.
36. J. MacMicking, Q.-w. Xie, C. Nathan, Nitric oxide and macrophage function, Annu. Rev. Immunol. 15(1) (1997) 323-350.
37. G. M. Halpenny, Heilman, B., Mascharak, P. K., Nitric Oxide (NO)-Induced Death of Gram-negative Bacteria from a Light Controlled NO-Releasing Platform, Chemistry & Biodiversity 9(9) (2012) 1829-1839.
38. J. J. Rouby, The nose, nitric oxide, and paranasal sinuses: the outpost of pulmonary antiinfectious defenses?, American Journal of Respiratory and Critical Care Medicine 168(3) (2003) 265-266.
39. M. W. Vaughn, L. Kuo, J. C. Liao, Estimation of nitric oxide production and reaction rates in tissue by use of a mathematical model, Am. J. Physiol.: Heart Circ. Physiol 274(6) (1998) H2163-H2176.
40. H. Handa, E. J. Brisbois, T. C. Major, L. Refahiyat, K. A. Amoako, G. M. Annich, R. H. Bartlett, M. E. Meyerhoff, In vitro and in vivo study of sustained nitric oxide release coating using diazeniumdiolate-doped poly (vinyl chloride) matrix with poly (lactide-co-glycolide) additive, Journal of Materials Chemistry B 1(29) (2013) 3578-3587.
41. H. Handa, T. C. Major, E. J. Brisbois, K. A. Amoako, M. E. Meyerhoff, R. H. Bartlett, Hemocompatibility comparison of biomedical grade polymers using rabbit thrombogenicity model for preparing nonthrombogenic nitric oxide releasing surfaces, J. Mater. Chem. B 2(8) (2014) 1059-1067.
42. E. J. Brisbois, H. Handa, T. C. Major, R. H. Bartlett, M. E. Meyerhoff, Long-term nitric oxide release and elevated temperature stability with S-nitroso-N-acetylpenicillamine (SNAP)-doped Elast-eon E2As polymer, Biomaterials 34(28) (2013) 6957-6966.
43. M. A. DeGroote, F. C. Fang, Antimicrobial properties of nitric oxide, Nitric oxide and infection, Springer 2002, pp. 231-261.
44. J. Pant, M. Goudie, E. Brisbois, H. Handa, Nitric oxide releasing polyurethanes, Advances in Polyurethane Biomaterials, Elsevier 2016, pp. 471-550.
45. J. Sundaram, J. Pant, M. J. Goudie, S. Mani, H. Handa, Antimicrobial and Physicochemical Characterization of Biodegradable, Nitric Oxide-Releasing Nanocellulose-Chitosan Packaging Membranes, J. Agric. Food Chem. (2016).
46. E. J. Brisbois, J. Bayliss, J. Wu, T. C. Major, C. Xi, S. C. Wang, R. H. Bartlett, H. Handa, M. E. Meyerhoff, Optimized polymeric film-based nitric oxide delivery inhibits bacterial growth in a mouse burn wound model, Acta Biomaterialia 10(10) (2014) 4136-4142.
47. B. J. Heilman, G. M. Halpenny, P. K. Mascharak, Synthesis, characterization, and light-controlled antibiotic application of a composite material derived from polyurethane and silica xerogel with embedded photoactive manganese nitrosyl, Journal of Biomedical Materials Research Part B: Applied Biomaterials 99(2) (2011) 328-337.
48. B. J. Nablo, T.-Y. Chen, M. H. Schoenfisch, Sol-gel derived nitric-oxide releasing materials that reduce bacterial adhesion, J. Am. Chem. Soc. 123(39) (2001) 9712-9713.
49. B. J. Nablo, M. H. Schoenfisch, Antibacterial properties of nitric oxide-releasing sol-gels, Journal of Biomedical Materials Research Part A 67(4) (2003) 1276-1283.
50. E. M. Hetrick, M. H. Schoenfisch, Reducing implant-related infections: active release strategies, Chem. Soc. Rev. 35(9) (2006) 780-789.
51. E. M. Hetrick, M. H. Schoenfisch, Antibacterial nitric oxide-releasing xerogels: Cell viability and parallel plate flow cell adhesion studies, Biomaterials 28(11) (2007) 1948-1956.

52. F. C. Fang, Perspectives series: host/pathogen interactions. Mechanisms of nitric oxide-related antimicrobial activity, Journal of Clinical Investigation 99(12) (1997) 2818-2825.
53. B. J. Privett, A. D. Broadnax, S. J. Bauman, D. A. Riccio, M. H. Schoenfisch, Examination of bacterial resistance to exogenous nitric oxide, Nitric Oxide 26(3) (2012) 169-173.
54. M. Feelisch, The use of nitric oxide donors in pharmacological studies, Naunyn-Schmiedeberg's Arch. Pharmacol. 358(1) (1998) 113-122.
55. C. Bogdan, Nitric oxide and the immune response, Nat. Immunol. 2(10) (2001) 907-916.
56. T. Hakim, K. Sugimori, E. Camporesi, G. Anderson, Half-life of nitric oxide in aqueous solutions with and without haemoglobin, Physiological measurement 17(4) (1996) 267.
57. D. L. H. Williams, The chemistry of S-nitrosothiols, Accounts of Chemical Research 32(10) (1999) 869-876.
58. E. J. Brisbois, T. C. Major, M. J. Goudie, R. H. Bartlett, M. E. Meyerhoff, H. Handa, Improved hemocompatibility of silicone rubber extracorporeal tubing via solvent swelling-impregnation of S-nitroso-N-acetylpenicillamine (SNAP) and evaluation in rabbit thrombogenicity model, Acta biomaterialia 37 (2016) 111-119.
59. E. J. Brisbois, R. P. Davis, A. M. Jones, T. C. Major, R. H. Bartlett, M. E. Meyerhoff, H. Handa, Reduction in thrombosis and bacterial adhesion with 7 day implantation of S-nitroso-N-acetylpenicillamine (SNAP)-doped Elast-eon E2As catheters in sheep, Journal of Materials Chemistry B (2015).
60. M. J. Goudie, E. J. Brisbois, J. Pant, A. Thompson, J. A. Potkay, H. Handa, Characterization of an S-nitroso-N-acetylpenicillamine-based nitric oxide releasing polymer from a translational perspective, Int. J. Polym. Mater. Polym. Biomater. 65(15) (2016) 769-778.
61. I. Chipinda, R. H. Simoyi, Formation and stability of a nitric oxide donor: S-nitroso-N-acetylpenicillamine, The Journal of Physical Chemistry B 110(10) (2006) 5052-5061.
62. M. C. Frost, M. E. Meyerhoff, Controlled photoinitiated release of nitric oxide from polymer films containing S-nitroso-N-acetyl-DL-penicillamine derivatized fumed silica filler, J. Am. Chem. Soc. 126(5) (2004) 1348-1349.
63. B. J. Nablo, M. H. Schoenfisch, Poly (vinyl chloride)-coated sol-gels for studying the effects of nitric oxide release on bacterial adhesion, Biomacromolecules 5(5) (2004) 2034-2041.
64. B. J. Nablo, A. R. Rothrock, M. H. Schoenfisch, Nitric oxide-releasing sol-gels as antibacterial coatings for orthopedic implants, Biomaterials 26(8) (2005) 917-924.
65. N. Torres, S. Oh, M. Appleford, D. D. Dean, J. H. Jorgensen, J. L. Ong, C. M. Agrawal, G. Mani, Stability of antibacterial self-assembled monolayers on hydroxyapatite, Acta Biomater. 6(8) (2010) 3242-3255.
66. M. Diepens, P. Gijsman, Photo-oxidative degradation of bisphenol A polycarbonate and its possible initiation processes, Polymer Degradation and Stability 93(7) (2008) 1383-1388.
67. Y. Wo, Z. Li, E. J. Brisbois, A. Colletta, J. Wu, T. C. Major, C. Xi, R. H. Bartlett, A. J. Matzger, M. E. Meyerhoff, Origin of long-term storage stability and nitric oxide release behavior of carbosil polymer doped with S-nitroso-N-acetyl-D-penicillamine, ACS Appl. Mater. Interfaces 7(40) (2015) 22218-22227.
68. M. Goudie, B. M. Brainard, C. W. Schmiedt, H. Handa, Characterization and in vivo performance of nitric oxide-releasing extracorporeal circuits in a feline model of thrombogenicity, Journal of Biomedical Materials Research Part A (2016).
69. E. J. Brisbois, T. C. Major, M. J. Goudie, M. E. Meyerhoff, R. H. Bartlett, H. Handa, Attenuation of thrombosis and bacterial infection using dual function nitric oxide releasing central venous catheters in a 9 day rabbit model, Acta Biomater. 44 (2016) 304-312.
70. E. J. Brisbois, M. Kim, X. Wang, A. Mohammed, T. C. Major, J. Wu, J. Brownstein, C. Xi, H. Handa, R. H. Bartlett, Improved Hemocompatibility of Multi-Lumen Catheters via Nitric Oxide (NO) Release from S-Nitroso-N-acetylpenicillamine (SNAP) Composite Filled Lumen, ACS Appl. Mater. & Interfaces (2016).
71. E. J. Brisbois, R. P. Davis, A. M. Jones, T. C. Major, R. H. Bartlett, M. E. Meyerhoff, H. Handa, Reduction in thrombosis and bacterial adhesion with 7 day implantation of S-nitroso-N-acetylpenicillamine (SNAP)-doped Elast-eon E2As catheters in sheep, J. Mater. Chem. B 3(8) (2015) 1639-1645.
72. D. Rana, T. Matsuura, Surface Modifications for Antifouling Membranes, Chem. Rev 110 (2010) 2448-2471.
73. S. Chen, L. Li, C. Zhao, J. Zheng, Surface hydration: Principles and applications toward low-fouling/nonfouling biomaterials, Polymer 51(23) (2010) 5283-5293.
74. N. D. Allan, K. Giare-Patel, M. E. Olson, An in vivo rabbit model for the evaluation of antimicrobial peripherally inserted central catheter to reduce microbial migration and colonization as compared to an uncoated PICC, BioMed Research International 2012 (2012).
75. M. Otto, Staphylococcal infections: mechanisms of biofilm maturation and detachment as critical determinants of pathogenicity, Annu. Rev. Med. 64 (2013) 175-188.
76. M. R. Kiedrowski, A. R. Horswill, New approaches for treating staphylococcal biofilm infections, Annals of the New York Academy of Sciences 1241(1) (2011) 104-121.
77. H. Roy, Tuning the properties of the bacterial membrane with aminoacylated phosphatidylglycerol, IUBMB life 61(10) (2009) 940-953.
78. A. E. Carpenter, T. R. Jones, M. R. Lamprecht, C. Clarke, I. H. Kang, O. Friman, D. A. Guertin, J. H. Chang, R. A. Lindquist, J. Moffat, P. Golland, D. M. Sabatini, CellProfiler: image analysis software for identifying and quantifying cell phenotypes, Genome Biology 7(10) (2006) 1-11.
79. L. Kamentsky, T. R. Jones, A. Fraser, M.-A. Bray, D. J. Logan, K. L. Madden, V. Ljosa, C. Rueden, K. W. Eliceiri, A. E. Carpenter, Improved structure, function and compatibility for CellProfiler: modular high-throughput image analysis software, Bioinformatics 27(8) (2011) 1179-1180.
80. J. S. Louie, I. Pinnau, I. Ciobanu, K. P. Ishida, A. Ng, M. Reinhard, Effects of polyether-polyamide block copolymer coating on performance and fouling of reverse osmosis membranes, Journal of Membrane Science 280(1-2) (2006) 762-770.

Example 3

To explore the covalent grafting of zwitterionic polymers to various substrates ranging from hydrophilic to hydrophobic, we incorporated the benzophenone (BP) chromophore, a photoactive tethering reagent, into the polymeric backbone.[19-24] The BP group can produce a diradical under low-intensity UV irradiation (350-365 nm) that abstracts an aliphatic hydrogen from a neighboring C—H bond to form a new C—C bond, without intensive UV oxidative damage to the polymer or substrates.[20] Through this process, network polymer films can be grafted with excellent durability to a broad selection of C—H containing materials and surfaces, and has been used for many applications such as microfluidics,[25-26] organic semiconductors,[27] redox polymers,[28-29] anti-icing polymers,[30] and biosensors.[31-32]

Nitric oxide (NO) is known as a potent and nonspecific bactericidal agent due to its natural broad-spectrum antimicrobial properties with low risk for promoting bacterial resistance.[33-35] NO utilizes several antimicrobial mechanisms including nitrosation of amines and thiols, lipid peroxidation, tyrosine nitration and DNA cleavage.[36] Major classes of current NO donors include organic nitrates, metal-NO complexes, N-nitrosamines, and S-nitrosothiols,[37] S-nitroso-N-acetylpenicillamine (SNAP), a commonly studied NO donor, exhibits significant antimicrobial and antithrombotic effects.[38-39] In our previous studies, SNAP has been successfully doped into CarboSil polymer films, and these SNAP-doped polyurethane-based materials can release NO for extended periods (20 days) with very low levels of leaching.[38, 40-41]

In this work, we synthesized zwitterionic terpolymers (2-methacryloyloxyethyl phosphorylcholine-co-butyl methacrylate-co-benzophenone, BPMPC) that can be covalently grafted to antimicrobial, NO-releasing CarboSil (silicone-polycarbonate-urethane thermoplastic) upon UV-irradiation. The polymer-coated surfaces are characterized in detail and the zwitterionic stability is assessed under physiological conditions. The protein repellency properties of these coatings are evaluated. At the same time, no SNAP degradation was observed during coating or UV irradiation, and the release profile remained above the physiological level for 2 weeks with the zwitterionic top-coat. Moreover, enhanced antimicrobial activity was demonstrated with bacteria testing.

Experiment Section

Materials 4-vinylbenzophenone (BP) was synthesized according to a previously reported method.[30] 2-Methacryloyloxyethyl phosphorylcholine (MPC), albumin from bovine serum (BSA), fluorescein isothiocyanate labeled bovine serum albumin (FTIC-BSA), N-acetyl-D-penicillamine (NAP), sodium nitrite ($NaNO_2$), concentrated sulfuric acid (conc. $H_2SO_4$), tetrahydrofuran (THF), sodium phosphate monobasic ($NaH_2PO_4$), sodium phosphate dibasic ($Na_2HPO_4$), potassium chloride, sodium chloride, and ethylenediamine tetraacetic acid (EDTA) were purchased from Sigma Aldrich (St. Louis, MO). 2,2'-azobis(2-methylpropionitrile) (AIBN) and n-butyl methacrylate (BMA) were bought from Alfa-Aesar (Haverhill, MA). Isobutyltrichlorosilane was purchased from Tokyo Chemical Industry (Portland, OR). Concentrated hydrochloric acid (conc. HCl), sodium hydroxide (NaOH), and methanol were bought from Fisher-Scientific (Hampton, NH). Potassium phosphate monobasic ($KH_2PO_4$) and lysozyme from egg white were purchased from BDH Chemicals—VWR International (West Chester, PA). Carbo-Sil™ 20 80A UR STPU (referred to as CarboSil hereon) was acquired from DSM Biomedical Inc. (Berkeley, CA). Milli-Q filter was used to obtain de-ionized (DI) water for all the aqueous solution preparations. Nitrogen and oxygen gas cylinders were purchased from Airgas (Kennesaw, GA). *Staphylococcus aureus* (ATCC 6538, *S. aureus*) was used for the bacterial experiments. LB Agar (LA), Miller and Luria broth (LB), Lennox were purchased from Fischer BioReagents (Fair Lawn, NJ). All the chemicals were used without further purification.

In brief, CarboSil polymers with 10 wt % SNAP (test samples) and no SNAP content (control samples) were prepared using solvent evaporation and/or spin coating method. These samples were then coated with a zwitterionic copolymer (referred to as BPMPC) which was covalently bonded to the CarboSil base polymers by UV-crosslinking. Surface analysis was performed on the films pre- and post-UV radiation to understand the crosslinking behavior of the polyzwitterionic system. Test and control samples with the BPMPC coating were analyzed for their NO release behavior. The samples were then tested for protein adhesion for 14 days in physiological conditions (37° C. in PBS) to evaluate antifouling properties of the topcoat. Finally, antimicrobial assay of the samples was done using a modified version of ASTM E2180 protocol.

Synthesis of NO Donor, SNAP

S-nitroso-N-acetylpenicillamine was synthesized using a revised approach for a method previously reported.[38] 1M $H_2SO_4$ and 1M HCl were mixed with an equimolar amount of NAP, methanol and $NaNO_2$ aqueous solution. This reaction mixture was stirred for 20 minutes and then cooled for 7 hours with a constant flow of air on the mixture. After evaporation of the unreacted portion of the reaction mixture, precipitated green crystals of SNAP were filtered, collected and dried in a covered vacuum desiccator. Dried crystals of SNAP were used for all experiments.

Synthesis of CarboSil Films Doped with SNAP

CarboSil films containing 10 wt % SNAP were prepared using solvent evaporation method. 700 mg of CarboSil was dissolved in 10 mL of THF to make the polymer solutions. 77 mg of SNAP was added to this solution for a final concentration of 10 wt % of SNAP. This polymer-SNAP blend was stirred in dark conditions until the SNAP crystals dissolved completely. The blend was then transferred into Teflon molds and allowed to let the solvent evaporate overnight in fume hood. The overnight dried films were then cut into circular shapes of 0.8 cm diameter each. Each sample was immersed into a CarboSil solution without SNAP (40 mg $mL^{-1}$ of polymer concentration in THF) to coat it (this was repeated thrice for each sample). The samples were dried overnight and then dried under vacuum for an additional 24 hours. This added drying time was included to eliminate any remaining THF which can affect any following studies. Weight of each film was recorded before the topcoat application for all SNAP leaching behavior tests. The formulated samples were stored in the freezer (−18° C.) in the dark between experiments to prevent escape of SNAP or consequent loss of NO. These SNAP-incorporated films were used for NO release, SNAP leaching and bacterial cell viability analyses. All samples used for the tests were less than a week old to ensure integrity of studies.

Synthesis of Zwitterionic Copolymer (BPMPC)

The polymer was synthesized by free radical polymerization. MPC (0.546 g, 1.85 mmol), n-BMA (0.105 mL, 0.66 mmol) and BP (0.027 g, 0.132 mmol) were dissolved in 5.3 mL ethanol (total monomer concentration 1.0 mmol $mL^{-1}$) with initiator AIBN (0.01 mmol $mL^{-1}$) and the solution was poured into polymerization tube. After degassing with argon for 30 minutes, the polymerization reaction was carried out under nitrogen flow at 60° C. for 16 h. The reaction was stopped by exposing the solution to air, cooled to room temperature, and poured into ethyl ether to precipitate the polymer. The white solid was collected by vacuum filtration and dried under vacuum for 12 h. Yield: 0.552 g, 83%. $^1$H NMR ($D_2O$) was taken to confirm the polymer composition.

Crosslinking of BPMPC with Substrates

Silicon substrates were cut into 2.4 cm×2.4 cm pieces and sonicated with deionized water, isopropanol, and acetone for 5 min each then dried under nitrogen, followed by plasma (Harrick Plasma PDC-32G) clean and treated with iBTS in toluene overnight before modification with the polymer. CarboSil substrates were coated with polymer without pretreatment.

Two coating method were utilized when applying BPMPC on substrates: spin coating and spray coating. For spin coating, polymer modified film was developed on functionalized silicon substrate by using 0.5 mL BPMPC/ethanol solution (10 mg mL$^{-1}$) at 1000 rpm for 30 seconds. Spray coating was applied for CarboSil films with and without SNAP. BPMPC/ethanol solution (2 mg mL$^{-1}$) was sprayed using a spray gun from a distance of 10 cm onto vertically placed substrates to achieve uniform coating upon drying. We used spin coating in the protein adsorption experiments, and spray coating in SNAP/NO release and bacterial experiments, based on method that afforded the smoothest, pin-hole free coating on different forms of substrate. Then the BPMPC substrates were irradiated with UV light (UVP, 254 nm, 6.5 mW cm$^{-2}$) for 1 min to covalently bond the BPMPC to the surface. The substrates were rinsed with abundant ethanol to remove unattached BPMPC then dried under nitrogen.

Characterization of the Polymer Coatings

The surface wettability was characterized by measuring the static water contact angle, which obtained from a DSA 100 drop shape analysis system (KRÜSS) with a computer-controlled liquid dispensing system. 1 µL DI water droplets were deposited onto substrate surfaces, and the water contact angles were measured within 10 seconds through the analysis of photographic images. The cross-linking kinetics of BPMPC coating was investigated by a UV-vis spectroscopy (Varian) with 254 nm UV light. The thickness of the spin-coated polymer layer on the silicon substrates and CarboSil substrates were measured by M-2000V Spectroscopic Ellipsometer (J.A. Woollam co., INC.) with a white light source at three incident angles (65°, 70°, and 75°). The thickness of the modified layer was measured and calculated using a Cauchy layer model. Infrared spectroscopy studies of polymer coated films were done using a Thermo-Nicolet model 6700 spectrometer equipped with a variable angle grazing angle attenuated total reflection (GATR-ATR) accessory (Harrick Scientific).

SNAP Leaching Study and NO-Release Profile

The percentage of SNAP discharged from the samples were quantified by noting the absorbance of the PBS solutions (used to soak the samples) at 340 nm (characteristic absorbance maxima of S—NO group of SNAP). Each sample was weighed before coating with non-SNAP polymer solutions to determine the initial amount of SNAP in each film. The films were then immersed in vials containing PBS (pH 7.4 with 100 µM EDTA to prevent catalysis of NO release by metal ions) and stored at 37° C. A UV-vis spectrophotometer (Thermoscientific Genesys 10S UV-vis) was utilized to quantify the absorbance of the buffer solutions in the required time intervals. The readings were converted to wt % of SNAP in the buffer utilizing the initial amount of SNAP present in each sample. 1 mL aliquots of the PBS solution in which the samples were soaked was used for each sample absorbance measurement to avoid any inconsistent readings and three replicates were utilized for each quantification. The calibration graph with known amounts of SNAP in PBS (with EDTA) was used to interpolate the absorbance quantifications recorded from the study and convert them to concentrations of SNAP in the quantified sample.

SNAP incorporated in the polymers release NO in physiological conditions and this release was measured and recorded in real time for the study using Sievers chemiluminescence NO Analyzers® (NOA 280i, GE Analytical, Boulder, CO, USA). The sample holder maintained dark conditions for the samples to prevent catalysis of the NO production by any light source. It was filled with 5 mL of PBS (pH 7.4 with 100 µM of EDTA) to soak the samples. EDTA acted as a chelating agent to prevent catalysis of NO production by metal ions in the PBS. This buffer solution was maintained at 37° C. by a temperature-regulated water jacket placed around the sample holder. Once a baseline of NO flux without the sample (prepared according to Example 2: Nitric Oxide release kinetics) is established, the sample is then placed in the sample holder. Nitric oxide released by the sample in the sample holder was pushed and purged towards the analyzer by a continuous supply of nitrogen gas maintained at a constant flow rate of 200 mL min$^{-1}$ through the sweep and bubble flows. The NO released by the sample is pushed towards the chemiluminescence detection chamber. The voltage signal produced is converted to concentration of NO and displayed on the analyzer's screen. Using the raw data in ppb form and NOA constant (mol ppb$^{-1}$ s$^{-1}$), the data in ppb is normalized for surface area of the sample and converted to NO flux units (×10$^{-10}$ mol cm$^{-2}$ min$^{-1}$). Data was collected in the time intervals mentioned and samples were stored in a PBS (with EDTA) solution at 37° C. in dark conditions between measurements. The PBS was replaced daily to avoid any accumulation of SNAP leached or NO released during the storage time. The instrument operating parameters were a cell pressure of 7.4 Torr, a supply pressure of 6.1 psig and a temperature of −12° C. Three replicates were used for each measurement.

Protein Adhesion Assay

Protein adsorption test is a significant important method for evaluating the blood adhesion. Therefore, the thickness change of substrates before and after incubation in protein solutions was monitored, as an indication of protein adsorption. Coated substrates were incubated in fibrinogen (1 mg mL$^{-1}$) and lysozyme (1 mg mL$^{-1}$) in PBS (pH 7.4, 0.01 M) solutions up to 14 days, followed by thickness measurement every day.

In the second approach, fluorescein isothiocyanate-bovine serum albumin (FITC-BSA, 2 mg mL$^{-1}$) in PBS solution was used to evaluate the protein adsorption behavior on the surface of CarboSil substrate modified by BPMPC.[42-43] Substrates were immersed in FITC-BSA solution for one and half hour at 37° C., then rinsed with distilled water and dried with nitrogen. The substrates with protein then analyzed by Nikon Eclipse NI-U fluorescence microscope (Nikon Instruments, Inc.), using a 5× objective lens, with filter set (Ex/Em 470/525 nm). To confirm the long-term resistance to protein adsorption, the substrates were incubated in BSA (1 mg ml$^{-1}$) PBS solution for up to 7 days at 37° C. before putting in FITC-BSA solution.

Bacterial Assay

Bacterial adhesion for each of the samples was calculated in terms of the bacterial cell viability using serial dilution after an incubation period of 24 hours. The method used to perform this assay was based on a modified version of the American Society for Testing and Materials E2180 protocol. S. aureus was used for antimicrobial evaluation of the samples. Bacteria were cultured in LB Broth (Lennox) at 37° C. and grown to ~10$^6$ colony-forming units (CFU) per mL as measured by optical density. The resulting overnight culture was collected by centrifugation (2500 g, 7 min) and resuspended in PBS. This resuspended bacterial suspension was used for incubation of polymer samples for 24 hours.

After incubation with the bacterial solution, samples were washed gently with PBS to remove any unbound bacteria. The samples were then placed in 1 mL of PBS and homogenized for 1 minute each to transfer any adhered bacteria to this new PBS solution. After homogenization, homogenate samples were serially diluted and plated onto LB Agar nutrient plates (37° C.). Bacterial viability was determined by counting the colonies on each plate manually. Calculation of bacterial adhesion was done by counting number of colonies per cm$^2$ of each sample.

Statistical Analysis. All data are quantified as mean±standard deviation with an n≥3 for all trials. The results between the control and test films were analyzed by a comparison of means using student's t-test. Values of p were obtained for the data analyzed and p<0.05 was considered significant.

Results and Discussion

The zwitterionic polymer (BPMPC) was synthesized by radical polymerization in ethanol. The copolymer composition was confirmed by $^1$H NMR spectroscopy, and consisted of 74:18:8 (MPC:nBMA:BP), which roughly matched the monomer feed ratio. This ratio provided the optimal antifouling result (discussed below) along with the most uniform coating on both hydrophobic and hydrophilic substrates. The polymer synthesis is simple and straightforward, no further purification is required besides precipitation, which makes large-scale production feasible. BPMPC is a hydrophilic polymer due to the high concentration of MPC, and has a high solubility in aqueous and alcohol solutions. The butyl methacrylate component in the terpolymer aids in uniformity and substrate wetting (both hydrophobic and hydrophilic), along with providing additional photochemical cross-linking sites. As described above, the benzophenone component of BPMPC acts as a cross-linker between the hydrophilic polymer and any organic substrate through C—H activation.

The cross-linking kinetics of BPMPC was investigated by UV-vis spectroscopy on isobutyltrichlorosilane (iBTS) functionalized quartz substrates. The polymer solution (10 µL, 10 mg mL$^{-1}$) was drop cast on alkylated quartz and the solvent allowed to evaporate. The UV crosslinking reaction was monitored by UV-vis, where the decreasing absorbance of the BP group at 255 nm occurs with increased irradiation time. FIG. 2 shows the UV-vis spectra, where the absorbance maxima at 255 nm decreased dramatically from 0 to 120 s, and after 240 s, no further absorbance change was observed, even after prolonged irradiation. This result demonstrates that BPMPC crosslinking occurs with rapid kinetics, and only a few seconds are needed to covalently bond BPMPC to a variety of different substrates.

To further confirm the deposition and cross-linking of the BPMPC polymer, FTIR was conducted on coated substrates. In the IR spectra, absorption peaks of the carbonyl (1720 cm$^{-1}$) and PC groups (1240, 1080, and 970 cm$^{-1}$) were observed and assigned to the MPC units. The peak at (1650 cm$^{-1}$) represents the C=O stretch of BP ketone. A significant reduction of this peak after irradiation further supports the formation of a network polymer of covalent linkage between BP and substrate.

To test the stability and durability of the coating, we monitored the water contact angle of the BPMPC coated silicon samples up to 14 days. The coated substrates were immersed in PBS solution and stirred in an incubator at 37° C., subsequently rinsed with H$_2$O and dried with nitrogen before measuring the water contact angle (FIG. 4). The initial static contact angle for the bare CarboSil substrate is about 110°. A significant decrease in contact angle was observed after coating with BPMPC, from 110° to 50°, and this value of contact angle was maintained over a period of 14 days immersed in an agitated PBS solution, which suggests the BPMPC coating was covalent bonded to the substrates and does not delaminate under physiological conditions.

The control samples used to test NO release behavior were coated only with CarboSil (the same polymer used to incorporate SNAP) while the test samples were coated with CarboSil and BPMPC. The samples were tested in lightly agitated conditions to simulate physiological conditions. The samples were tested for a period of two weeks to demonstrate sustainable release of NO from the combination of hydrophobic and hydrophilic polymers.

A SNAP leaching study was conducted first to measure the retention of SNAP in the control and test polymer films during the course of the study. Measurements were recorded every other day for 2 weeks of soaking in PBS (FIG. 5A). A high amount of SNAP retention in the polymers ensures sustained release of NO from the polymer matrix and minimizes the risks (if any) associated with SNAP leaching.[44] As seen in FIG. 5A, for the initial measurement (Day 0 on graph of FIG. 5A) of leaching after one hour of storage in 37° C. in PBS, a loss of 0.39±0.06% and 0.47±0.26% was recorded for the control and BPMPC-coated substrate, respectively. This initial higher leaching for the BPMPC-coated substrate is likely due to the hydrophilicity of the surface. However, SNAP leaching is almost identical between the control and test samples as supported by the data from 1 and 3 days of storage in 37° C. for BPMPC-coated test films (0.96±0.26% and 1.44±0.26% for day 1 and day 3, respectively) and control films (0.96±0.05% and 1.55±0.07% for day 1 and day 3, respectively).

This trend of lower leaching of the SNAP molecules from the test films was observed over a 14 day period. It is also to be noted that at no point during the 14-day period were the samples kept at a temperature below 37° C. or in dry conditions. This was done to closely simulate physiological conditions for a continuous duration. The leaching for both the control and test samples remained very low (<3.5%) over the experiment duration but it is worth noting here that despite the expectation that the hydrophilic coating could cause a higher leaching of SNAP molecules from the NO donor containing polymer by attracting water molecules to the polymer surface, this was not the case. This is likely due to the ultrathin nature of the coating, which influences the aqueous interface, but not the bulk of the polymer film.

NO release measurements of the control and test samples were also carried out for a period of 14 days (FIG. 5B). Measurements with a Sievers chemiluminescence NO analyzer is the standard characterization methodology accepted for polymers that release NO.[45-47] It measures NO release in real time via the measurement of voltage produced by the photons on the reaction of NO with ozone. In this study, samples were stored at a constant temperature of 37° C. and in PBS to simulate physiological conditions.

The results indicated a general trend of higher NO release from the test samples (SNAP-containing material coated with CarboSil and BPMPC) compared to the control samples (SNAP-containing material coated with only CarboSil). Day 0 measurements indicate that the test samples had a flux of $7.75 \pm 3.26$ ($\times 10^{-10}$) mol cm$^{-2}$ min$^{-1}$ while control samples had a flux of $3.76 \pm 1.50$ ($\times 10^{-10}$) mol cm$^{-2}$ min$^{-1}$ (Table 4). This burst of NO release from test samples results from the hydrophilicity of the topcoat which attracts water molecules to the sample surface. Water molecules on the surface can accommodate release of NO as SNAP is more soluble (and prone to S—N=O bond cleavage) in aqueous conditions. After a day of storage, the control samples show a sharp decrease in NO flux ($0.34 \pm 0.03 \times 10^{-10}$ mol cm$^{-2}$ min$^{-1}$). This is seen because of the initial loss in SNAP molecules on day 0 and inability to maintain a hydrated state for day 1. In contrast, BPMPC-coated substrates show three times the NO flux at $1.02 \pm 0.02 \times 10^{-10}$ mol cm$^{-2}$ min$^{-1}$. This difference in NO flux can result from the hydrophilic topcoat of test samples that maintains a hydrated surface layer, which facilitates the release of more NO. This trend of higher NO flux from test samples when compared to control samples can be seen through the 14-day study in Table 4 and the graph in FIG. 5B.

TABLE 4

Comparison of nitric oxide release kinetics between control and coated samples

| | 10% SNAP with only CarboSil topcoat (NO flux ($\times 10^{-10}$ mol min$^{-1}$ cm$^{-2}$) | 10% SNAP with CarboSil and BPMPC topcoat (NO flux ($\times 10^{-10}$ mol min$^{-1}$ cm$^{-2}$) |
|---|---|---|
| Day 0 | 3.759 ± 1.491 | 7.746 ± 3.263 |
| Day 1 | 0.335 ± 0.032 | 1.016 ± 0.198 |
| Day 3 | 0.141 ± 0.023 | 0.706 ± 0.157 |
| Day 5 | 0.110 ± 0.045 | 0.395 ± 0.208 |
| Day 7 | 0.105 ± 0.008 | 0.498 ± 0.173 |
| Day 10 | 0.247 ± 0.324 | 0.383 ± 0.040 |
| Day 14 | 0.127 ± 0.035 | 0.380 ± 0.125 |

At the end of the 14-day study, test samples ($0.38 \pm 0.13$) ($\times 10^{-10}$) mol cm$^{-2}$ min$^{-1}$) still release three times the NO flux compared to the control samples ($0.13 \pm 0.03$ ($\times 10^{-10}$) mol cm$^{-2}$ min$^{-1}$). This propensity of higher release of NO from CarboSil top-coated with BPMPC along with the reduction in leaching of SNAP is very beneficial and combines the material properties of CarboSil (low SNAP leaching) with a higher, sustained release of NO due to the hydrophilic BPMPC topcoat.

As mentioned earlier, the BPMPC coating has excellent hydrophilicity, which helps inhibit the adsorption of proteins from solution. Fibrinogen and lysozyme were used as model proteins to evaluate the antifouling properties of the BPMPC coatings. Fibrinogen is a large (340 kD, pI=6.0) protein, and a key biomacromolecule in the coagulation cascade that rapidly adsorbs to foreign surfaces and binds to and activates platelets. Lysozyme is a small protein (14 kD, pI=12) that is positively charged under physiological pH. FIG. 6A shows the adsorption thickness increase of Fibrinogen on CarboSil, CarboSil with 10% SNAP, BPMPC coated CarboSil, and BPMPC coated CarboSil with 10% SNAP substrates respectively. On the bare CarboSil films used as a control, the thickness increased about 3 nm after incubation for 24 hours, and increased over 30 nm after 2 weeks. The similar phenomenon was observed for CarboSil with 10% SNAP films, which indicated a high amount of protein adsorption on surface, and protein accumulation over time. On the other hand, for the CarboSil films coated with BPMPC, the adsorption amount is significantly lower, only a 2 nm increase was observed after incubation for 2 weeks. The large difference in adsorption thickness confirmed that BPMPC coating has an excellent protein resistance properties, even after UV activation. As expected, the BPMPC coated CarboSil with 10% SNAP films also shows low adsorption for Fibrinogen. Moreover, similar behavior was observed when films were subjected to lysozyme solution (FIG. 6B). The thickness increase in control group was over 14 nm, while the coated group was less than 3 nm. The protein adsorption results indicate that the hydrophilic BPMPC surface layer provides excellent protein-resistant properties.

To further confirm the antifouling effectiveness of the durable BPMPC coating, fluorescence microscopy was utilized to evaluate the protein adsorption on the uncoated and coated CarboSil films using FITC labeled BSA protein. The fouling levels were compared between uncoated and BPMPC coated CarboSil films using the same excitation light intensity and exposure time. The results indicated protein adsorption on the control samples, and enhanced fluorescent signal was observed in the samples pretreated with BSA PBS solution. These results demonstrate that after incubation in protein solution, a large amount of BSA was attached to the CarboSil samples, which facilitate the aggregation of FITC-BSA. On the contrary, protein adhesion to the surface of BPMPC modified samples was not observed, even after incubation in BSA solution for 7 days. From all of these results collectively, the control films demonstrate large amounts of protein adsorption, while the BPMPC coated films display excellent antifouling properties.

Bacterial adhesion, which often results in biofilm formation, is a prevalent issue in moist and humid environments, including implanted devices. The basic nutrients important for bacterial growth may be resourced from the device material, bodily proteins that attach post-implantation, or other bodily macromolecular contaminants that adhere to the surface of the device. Antimicrobial efficacy of the designed test samples was compared to the control samples to confirm their superior bactericidal and bacterial repulsion properties.

The samples were soaked in bacterial solutions containing ~$10^6$ CFU/mL of S. aureus. S. aureus is a commonly found nosocomial infection bacteria. It has been increasingly linked with healthcare-associated infections in the last two decades.[48] They are most commonly associated with cardiac devices, intravascular catheters and urinary catheters, among other prosthetic devices. This high prevalence of S. aureus along with its known affinity to proteins[49-50] that foul medical devices has made it a very important pathogen used to evaluate the antimicrobial efficacy of medical device materials. For these reasons, bacterial adhesion study of the antifouling-biocide releasing polymer developed was done with S. aureus.

As mentioned in the introduction, the NO molecules liberated by the decomposition of SNAP actively kill bacteria while the zwitterion topcoat repels protein adsorption, leading to enhanced antimicrobial efficacy. After 24-hours of incubation, the antimicrobial effect of the test samples was clearly observed. NO releasing polymers with a top-coat of BPMPC showed a bactericidal efficiency of 99.91±0.06% (~3 log reduction, FIG. 8) compared to the control samples where a growth of ~$10^6$ CFU/cm$^2$ was observed. This reduction is greater compared to films with only a BPMPC topcoat (70.15±14.13%) and also films with only NO-releasing moieties (98.88±0.54%). It can also be concluded from the results that BPMPC alone only reduces bacteria adhesion. However, because NO is not a contact active antimicrobial but a diffusing biocide, the SNAP-loaded samples also reduce bacterial adhesion significantly.

These results are consistent with the theoretical expectations underlying the surface chemistry of BPMPC and bactericidal properties of NO. In summary, the synergistic effect of the modifiable NO-release kinetics from CarboSil's surface and prevention of protein and/or bacterial adhesion due to BPMPC's surface chemistry will significantly reduce undesired clinical consequences for implanted medical devices.

Conclusions

In conclusion, we have demonstrated a combination of NO release and BPMPC can produce a material with antimicrobial ability and excellent antifouling properties. The formation of the covalent polymer network is rapid (less than 1 min) under mild UV conditions, and can be applied to various substrates, from hydrophilic to hydrophobic. More importantly, even though the BPMPC coating is around 50 nm, it resists moderate abrasion for over a week with retention of its antifouling property. Moreover, the NO release profile indicated a higher NO release from the BPMPC coated sample when compared to the control, with lower leaching of SNAP. The coatings were also challenged with protein adsorption tests for an extended time (up to 2 weeks), where antifouling properties remain. It is noteworthy that, the high killing efficiency of SNAP to *S. aureus* is enhanced by BPMPC coating. This one step photochemical attachment process of an antifouling coating to NO-releasing antimicrobial polyurethanes is a simple and scalable process that has application in both medical devices and other industrial applications where antifouling and antimicrobial properties are desired.

References for Example 3

1. Woo Kyung Cho, B. K., Insung S. Choi, High Wfficient Non-biofouling Coating of Zwitterionic Polymer: Poly ((3-(methacryloylamino)propyl)-dimethyl(3-sulfopropyl) ammonium hydroxide). *Langmuir* 2007, 23, 5678.
2. Nguyen, A. T.; Baggerman, J.; Paulusse, J. M.; van Rijn, C. J.; Zuilhof, H., Stable Protein-repellent Zwitterionic Polymer Brushes Grafted from Silicon Nitride. *Langmuir* 2011, 27 (6), 2587-94.
3. Kenawy el, R.; Worley, S. D.; Broughton, R., The chemistry and applications of antimicrobial polymers: a state-of-the-art review. *Biomacromolecules* 2007, 8 (5), 1359-84.
4. Dastjerdi, R.; Montazer, M., A Review on the Application of Inorganic Nano-structured Materials in the Modification of Textiles: Focus on Anti-microbial Properties. *Colloids Surf B Biointerfaces* 2010, 79 (1), 5-18.
5. Hetrick, E. M.; Schoenfisch, M. H., Reducing Implant-related Infections: Active Release Strategies. *Chem Soc Rev* 2006, 35 (9), 780-9.
6. Yatvin, J.; Gao, J.; Locklin, J., Durable defense: robust and varied attachment of non-leaching poly"-onium" bactericidal coatings to reactive and inert surfaces. *Chem Commun (Camb)* 2014, 50 (67), 9433-42.
7. Magill, S. S.; Edwards, J. R.; Bamberg, W.; Beldavs, Z. G.; Dumyati, G.; Kainer, M. A.; Lynfield, R.; Maloney, M.; McAllister-Hollod, L.; Nadle, J.; Ray, S. M.; Thompson, D. L.; Wilson, L. E.; Fridkin, S. K.; Emerging Infections Program Healthcare-Associated, I.; Antimicrobial Use Prevalence Survey, T., Multistate Point-prevalence Survey of Health Care-associated Infections. *N Engl J Med* 2014, 370 (13), 1198-208.
8. Lowe, S.; O'Brien-Simpson, N. M.; Connal, L. A., Antibiofouling Polymer Interfaces: Poly(ethylene glycol) and Other Promising Candidates. *Polym. Chem.* 2015, 6 (2), 198-212.
9. Jiang, S.; Cao, Z., Ultralow-fouling, Functionalizable, and Hydrolyzable Zwitterionic Materials and their Derivatives for Biological Applications. *Adv Mater* 2010, 22 (9), 920-32.
10. Wayne R. Gombotx, W. G., Thomas A. Horbett, Allan S. Hoffman, Protein Adsorption to Poly(ethylene oxide) Surfaces. *J. Biomed. Mater. Res.* 1991, 25, 1547-1562.
11. Shao, Q.; Jiang, S., Molecular Understanding and Design of Zwitterionic Materials. *Adv Mater* 2015, 27 (1), 15-26.
12. Zhang, Z.; Chao, T.; Chen, S. F.; Jiang, S. Y., Superlow Fouling Sulfobetaine and Carboxybetaine Polymers on Glass Slides. *Langmuir* 2006, 22 (24), 10072-10077.
13. Hucknall, A.; Rangarajan, S.; Chilkoti, A., In Pursuit of Zero: Polymer Brushes that Resist the Adsorption of Proteins. *Advanced Materials* 2009, 21 (23), 2441-2446.
14. Ladd, J.; Zhang, Z.; Chen, S.; Hower, J. C.; Jiang, S., Zwitterionic Polymers Exhibiting High Resistance to Nonspecific Protein Adsorption from Human Serum and Plasma. *Biomacromolecules* 2008, 9 (5), 1357-1361.
15. Holmlin, R. E.; Chen, X. X.; Chapman, R. G.; Takayama, S.; Whitesides, G. M., Zwitterionic SAMs that Resist Nonspecific Adsorption of Protein from Aqueous Buffer. *Langmuir* 2001, 17 (9), 2841-2850.
16. He, Y.; Hower, J.; Chen, S. F.; Bernards, M. T.; Chang, Y.; Jiang, S. Y., Molecular Simulation Studies of Protein Interactions with Zwitterionic Phosphorylcholine Self-assembled Monolayers in the Presence of Water. *Langmuir* 2008, 24 (18), 10358-10364.
17. Singha, P.; Locklin, J.; Handa, H., A review of the recent advances in antimicrobial coatings for urinary catheters. *Acta Biomaterialia* 2017, 50, 20-40.
18. Ren, P. F.; Yang, H. C.; Liang, H. Q.; Xu, X. L.; Wan, L. S.; Xu, Z. K., Highly Stable, Protein-Resistant Surfaces via the Layer-by-Layer Assembly of Poly(sulfobetaine methacrylate) and Tannic Acid. *Langmuir* 2015, 31 (21), 5851-8.
19. Turro, N. J., *Modern Molecular Photochemistry*. Benjamin/Cummings Pub Co.: Menlo Park, Calif., 1978.
20. Lin, A. A.; Sastri, V. R.; Tesoro, G.; Reiser, A.; Eachus, R., On the Crosslinking Mechanism of Benzophenone-containing Polyimides. *Macromolecules* 1988, 21 (4), 1165-1169.
21. Park, M.-K.; Deng, S.; Advincula, R. C., pH-Sensitive Bipolar Ion-Permselective Ultrathin Films. *Journal of the American Chemical Society* 2004, 126 (42), 13723-13731.

22. Higuchi, H.; Yamashita, T.; Horie, K.; Mita, I., Photo-cross-linking Reaction of Benzophenone-containing Polyimide and Its Model Compounds. *Chemistry of Materials* 1991, 3 (1), 188-194.

23. Braeuchle, C.; Burland, D. M.; Bjorklund, G. C., Hydrogen Abstraction by Benzophenone Studied by Holographic Photochemistry. *The Journal of Physical Chemistry* 1981, 85 (2), 123-127.

24. Lin, X.; Fukazawa, K.; Ishihara, K., Photoreactive Polymers Bearing a Zwitterionic Phosphorylcholine Group for Surface Modification of Biomaterials. *ACS Appl Mater Interfaces* 2015, 7 (31), 17489-98.

25. Samuel, J. D. J. S.; Brenner, T.; Prucker, O.; Grumann, M.; Ducree, J.; Zengerle, R.; Rühe, J., Tailormade Microfluidic Devices Through Photochemical Surface Modification. *Macromolecular Chemistry and Physics* 2010, 211 (2), 195-203.

26. Hu, S.; Ren, X.; Bachman, M.; Sims, C. E.; Li, G. P.; Allbritton, N. L., Surface-Directed, Graft Polymerization within Microfluidic Channels. *Analytical Chemistry* 2004, 76 (7), 1865-1870.

27. Virkar, A.; Ling, M.-M.; Locklin, J.; Bao, Z., Oligothiophene Based Organic Semiconductors with Cross-linkable Benzophenone Moieties. *Synthetic Metals* 2008, 158 (21-24), 958-963.

28. Bunte, C.; Prucker, O.; Konig, T.; Ruhe, J., Enzyme Containing Redox Polymer Networks for Biosensors or Biofuel Cells: A Photochemical Approach. *Langmuir* 2010, 26 (8), 6019-6027.

29. Bunte, C.; Ruhe, J., Photochemical Generation of Ferrocene-Based Redox-Polymer Networks. *Macromol Rapid Comm* 2009, 30 (21), 1817-1822.

30. Gao, J.; Martin, A.; Yatvin, J.; White, E.; Locklin, J., Permanently Grafted Icephobic Nanocomposites with High Abrasion Resistance. *J. Mater. Chem. A* 2016, 4 (30), 11719-11728.

31. Abu-Rabeah, K.; Atias, D.; Herrmann, S.; Frenkel, J.; Tavor, D.; Cosnier, S.; Marks, R. S., Characterization of Electrogenerated Polypyrrole-Benzophenone Films Coated on Poly(pyrrole-methyl metacrylate) Optic-Conductive Fibers. *Langmuir* 2009, 25 (17), 10384-10389.

32. Brandstetter, T.; Bohmer, S.; Prucker, O.; Bisse, E.; zur Hausen, A.; Alt-Morbe, J.; Ruhe, J., A Polymer-based DNA Biochip Platform for Human Papilloma Virus Genotyping. *J Virol Methods* 2010, 163 (1), 40-48.

33. Brisbois, E. J.; Bayliss, J.; Wu, J.; Major, T. C.; Xi, C.; Wang, S. C.; Bartlett, R. H.; Handa, H.; Meyerhoff, M. E., Optimized polymeric film-based nitric oxide delivery inhibits bacterial growth in a mouse burn wound model. *Acta biomaterialia* 2014, 10 (10), 4136-4142.

34. Pegalajar-Jurado, A.; Wold, K. A.; Joslin, J. M.; Neufeld, B. H.; Arabea, K. A.; Suazo, L. A.; McDaniel, S. L.; Bowen, R. A.; Reynolds, M. M., Nitric oxide-releasing polysaccharide derivative exhibits 8-log reduction against *Escherichia coli, Acinetobacter baumannii* and *Staphylococcus aureus. Journal of Controlled Release* 2015, 217, 228-234.

35. Backlund, C. J.; Worley, B. V.; Schoenfisch, M. H., Anti-biofilm action of nitric oxide-releasing alkyl-modified poly (amidoamine) dendrimers against *Streptococcus mutans. Acta biomaterialia* 2016, 29, 198-205.

36. Fang, F. C., Antimicrobial actions of nitric oxide. *Nitric oxide: biology and chemistry/official journal of the Nitric Oxide Society* 2012, 27, Supplement, S10.

37. Wang, P. G.; Xian, M.; Tang, X.; Wu, X.; Wen, Z.; Cai, T.; Janczuk, A. J., Nitric Oxide Donors: Chemical Activities and Biological Applications. *Chemical Reviews* 2002, 102 (4), 1091-1134.

38. Brisbois, E. J.; Handa, H.; Major, T. C.; Bartlett, R. H.; Meyerhoff, M. E., Long-term nitric oxide release and elevated temperature stability with S-nitroso-N-acetylpenicillamine (SNAP)-doped Elast-eon E2As polymer. *Biomaterials* 2013, 34 (28), 6957-66.

39. Broniowska, K. A.; Hogg, N., The Chemical Biology of S-Nitrosothiols. *Antioxidants & Redox Signaling* 2012, 17 (7), 969-980.

40. Singha, P.; Pant, J.; Goudie, M. J.; Workman, C. D.; Handa, H., Enhanced antibacterial efficacy of nitric oxide releasing thermoplastic polyurethanes with antifouling hydrophilic topcoats. *Biomaterials Science* 2017.

41. Brisbois, E. J.; Davis, R. P.; Jones, A. M.; Major, T. C.; Bartlett, R. H.; Meyerhoff, M. E.; Handa, H., Reduction in Thrombosis and Bacterial Adhesion with 7 Day Implantation of -Nitroso-acetylpenicillamine (SNAP)-Doped Elast-eon E2As Catheters in Sheep. *J Mater Chem B Mater Biol Med* 2015, 3 (8), 1639-1645.

42. Sundaram, H. S.; Han, X.; Nowinski, A. K.; Ella-Menye, J. R.; Wimbish, C.; Marek, P.; Senecal, K.; Jiang, S., One-step dip coating of zwitterionic sulfobetaine polymers on hydrophobic and hydrophilic surfaces. *ACS Appl Mater Interfaces* 2014, 6 (9), 6664-71.

43. Diaz Blanco, C.; Ortner, A.; Dimitrov, R.; Navarro, A.; Mendoza, E.; Tzanov, T., Building an antifouling zwitterionic coating on urinary catheters using an enzymatically triggered bottom-up approach. *ACS Appl Mater Interfaces* 2014, 6 (14), 11385-93.

44. Scatena, R.; Bottoni, P.; Pontoglio, A.; Giardina, B., Pharmacological modulation of nitric oxide release: new pharmacological perspectives, potential benefits and risks. *Curr Med Chem* 2010, 17 (1), 61-73.

45. Wo, Y.; Li, Z.; Brisbois, E. J.; Colletta, A.; Wu, J.; Major, T. C.; Xi, C.; Bartlett, R. H.; Matzger, A. J.; Meyerhoff, M. E., Origin of Long-Term Storage Stability and Nitric Oxide Release Behavior of CarboSil Polymer Doped with S-Nitroso-N-acetyl-d-penicillamine. *ACS Applied Materials & Interfaces* 2015, 7 (40), 22218-22227.

46. Joslin, J. M.; Lantvit, S. M.; Reynolds, M. M., Nitric Oxide Releasing Tygon Materials: Studies in Donor Leaching and Localized Nitric Oxide Release at a Polymer-Buffer Interface. *ACS Applied Materials & Interfaces* 2013, 5 (19), 9285-9294.

47. Privett, B. J.; Broadnax, A. D.; Bauman, S. J.; Riccio, D. A.; Schoenfisch, M. H., Examination of bacterial resistance to exogenous nitric oxide. *Nitric oxide: biology and chemistry/official journal of the Nitric Oxide Society* 2012, 26 (3), 169-73.

48. Tong, S. Y.; Davis, J. S.; Eichenberger, E.; Holland, T. L.; Fowler, V. G., *Staphylococcus aureus* infections: epidemiology, pathophysiology, clinical manifestations, and management. *Clinical microbiology reviews* 2015, 28 (3), 603-661.

49. Ní Eidhin, D.; Perkins, S.; Francois, P.; Vaudaux, P.; Höök, M.; Foster, T. J., Clumping factor B (ClfB), a new surface-located fibrinogen-binding adhesin of *Staphylococcus aureus. Molecular Microbiology* 1998, 30 (2), 245-257.

50. Boland, T.; Latour, R. A.; Stutzenberger, F. J., Molecular basis of bacterial adhesion. In *Handbook of Bacterial Adhesion*, Springer: 2000, pp 29-41.

Example 4

Materials and Methods

Synthesis of SIM Material

Figure 16:
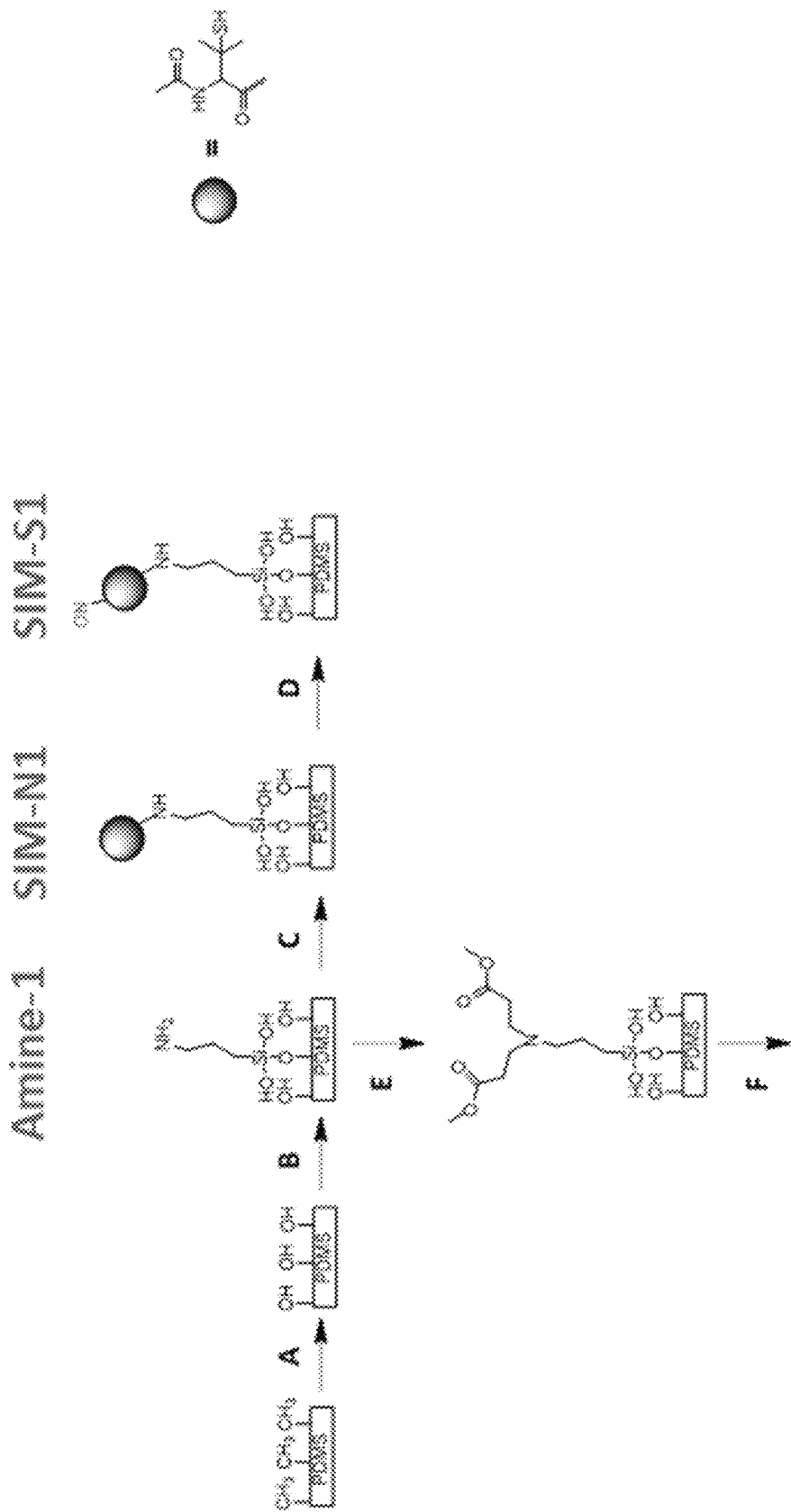
FIG. 16 shows preparation of surface immobilized S-nitroso-N-acetyl-d-penicillamine (SIM-S1, SIM-S2, SIM-S4) A) Functionalization of PDMS surface with hydroxyl groups by submerging it in 50:50 ratio of 13 N HCl:30 wt. % H2O2 in H2O B) Treatment with APTMES for amine functionalization C) Ring-opening reaction of NAP-thiolactone with free amine groups to produce free thiol groups (repeated for step G and K for SIM-N2 and SIM-N4, respectively) D) Nitrosation of thiol groups with tert-butyl nitrite (repeated for step H and L for SIM-S2 and SIM-S4, respectively) E) Branching of primary amine via reaction with methyl acrylate (repeated for step I) F) Amine functionalization of branched site using ethylene diamine (repeated for step J).

Silicone films were first fabricated by mixing Sylgard 184 base to curing agent (ratio of 10:1). The solution was cast into Teflon molds and placed under vacuum for degassing. The casted solution was then placed in an oven (80° C., 90 min) for curing. Surface modification was performed in steps, illustrated in FIG. 16, as referred to below. To create a hydroxyl group functionalized surface (step A), the silicone films were submerged in a mixture of 13 N HCl:30 wt. % $H_2O_2$ (50:50) in $H_2O$ under mild agitation (15 min). The surfaces were then rinsed with DI $H_2O$ and dried under vacuum. The amine functionalization (step B) was then achieved by submerging the hydroxyl-functionalized surfaces in 5 wt. % APTMES in extra dry acetone for 2 h. Films were then rinsed with extra dry acetone to remove any non-covalently attached silane from the surface, and vacuum dried for 24 h. Branching of the immobilized moieties was achieved through incubation of the amine functionalized surface in 2:1 (v/v) methanol:methyl acrylate (24 h) (steps E and I) followed by 2:1 (v/v) methanol:ethylenediamine (24 h) (steps F and J) as shown in FIG. 16. Samples were rinsed twice with methanol (20 mL) between incubating solutions. Amine-functionalized surfaces were then submerged in 10 mg $mL^{-1}$ NAP-thiolactone in toluene for 24 h (steps C, G, and K), allowing for the ring opening reaction of thiolactone to bind to free amines.[24, 25] The samples were then air-dried for 5 h to completely remove any residual solvent. Nitrosation of the immobilized NAP (steps D, H, and L) was achieved by incubation in neat tert-Butyl nitrite for 2 h. The resultant SIMS samples were stored at −20° C. for further experiments.

Contact Angle and FTIR Analysis

Surface properties and proof of attachment of nitric oxide donors to silicone surfaces was analyzed using contact angle measurements and FTIR. Static contact angle was measured using a DSA 100 drop shape analysis system (KRU¨SS) with a computer-controlled liquid dispensing system (Krüss). A 3 μL droplet of water was placed on various silicone films, and the average of left and right contact angles were measured via the Krüss software. Infrared spectroscopy studies of the samples were done using a Thermo-Nicolet model 6700 spectrometer.

Free Amine Quantification

Quantification of APTMES attachment to the surface of the PDMS was done using an ATTO-TAG (3-2-(furoyl quinoline-2-carboxaldehyde)) (FQ) Amine-derivatization kit (ThermoFisher Scientific, Waltham, MA). Each primary amine forms a conjugate with the FQ reagent which can then be fluorescently detected. Fluorescent count was measured using a Biotek Synergy microplate reader (Winooski, VT). The tested samples of APTMES functionalized PDMS were first carefully measured before being placed in a solution containing 15 μL of 10 mM potassium cyanide (KCN), 25 μL of 0.01 M PBS (pH=7.4), and 10 μL of 10 mM FQ solution (in methanol). The samples were then protected from light and allowed to react for 1 h. The solutions containing the samples were then gently agitated to ensure all of the florescent product is removed from the surface. The sample pieces were then discarded and the solutions with the fluorescent product were placed in a 96-well plate to be measured at excitation and emission wavelengths of 480 nm and 590 nm, respectively. Calibration curves were done using prepared glycine to directly relate the fluorescent count with primary amine concentration.

Nitric Oxide Release Characteristics

Nitric oxide release from the films containing SNAP was measured using a Sievers Chemiluminescence Nitric Oxide Analyzer (NOA) 280i (Boulder, CO). The Sievers chemiluminescence Nitric Oxide analyzer is considered as the gold standard for detecting nitric oxide and is widely used due to its ability to limit interfering species, such as nitrates and nitrites, as they are not transferred from the sample vessel to the reaction cell. Films were then placed in the sample vessel immersed in PBS (pH 7.4) containing 100 mM EDTA. Nitric oxide was continuously purged from the buffer and swept from the headspace using nitrogen sweep gas and bubbler into the chemiluminescence detection chamber.

Protein Repulsion Quantification

Levels of protein adhesion were quantified for the various materials using a modified version of a previously reported method.[7] FITC-human fibrinogen (13 mg/mL, Molecular Innovations) was diluted to achieve 2 mg $mL^{-1}$ in PBS (pH 7.4). Silicone disks were incubated at 37° C. for 30 min in a 96-well plate, followed by the addition of the stock protein solution to achieve a concentration of 2 mg $mL^{-1}$.[7] Following 2 h of incubation, infinite dilution of the well contents was carried out to wash away the bulk and any loosely bound protein from the materials. The fluorescence of each well (n=8) was then measured using a 96-well plate reader (Biotek), and the amount of protein adsorbed was determined via a calibration curve.

Bacterial Adhesion Assay

The ability of the samples to inhibit growth and promote killing of the adhered bacteria on the polymer surface was tested following guidelines based on American Society for Testing and Materials E2180 protocol with the commonly found nosocomial pathogen, Gram-positive S. aureus (ATCC 6538). A single colony of bacteria was isolated from a previously cultured LB-agar plate and incubated in LB Broth (37° C., 150 rpm, 14-16 h). The optical density of the culture was measured at a wavelength of 600 nm using a UV-vis spectrophotometer (Thermoscientific Genesys 10S UV-Vis) to ensure the presence of ~$10^6$-$10^8$ CFU $mL^{-1}$. The overnight culture was then centrifuged at 2500 rpm for 7 min to obtain the bacterial pellet. The bacterial pellet obtained was resuspended in sterile PBS. The polymer samples (SR control, SIM-N1, SIM-S1, SIM-N2 and SIM-S2) were then incubated in the bacterial suspension (37° C., 24 h, 200 rpm). After incubation, samples were removed from the bacterial suspension and rinsed with sterile PBS to remove any unbound bacteria. Each sample was then sonicated for 1 min using an Omni Tip homogenizer to collect adhered bacteria in sterile PBS. To ensure proper homogenization of the collected bacteria, the samples were vortexed for 45 s each. The solutions were serially diluted, plated on LB agar medium and incubated at 37° C. After 24 h, the total CFUs for serially diluted and plated bacterial solutions were counted.

Platelet Adhesion Assay

Freshly drawn porcine blood was purchased from Lampire Biologicals. The anticoagulated blood was centrifuged (1100 rpm, 12 min) using the Eppendorf Centrifuge 5702. The platelet rich plasma (PRP) portion was collected carefully with a pipet as to not disturb the buffy coat. The remaining samples were then centrifuged (4000 rpm, 20 min) to retrieve platelet poor plasma (PPP). Total platelet counts in both PRP and PPP fractions were determined using a hemocytometer (Fisher). The PRP and PPP were combined in a ratio to give a final platelet concentration ca. $2 \times 10^8$ platelets $mL^{-1}$. Calcium chloride ($CaCl_2$) was added to the final platelet solution to achieve a final concentration of 2.5 mM.[7] Disks of each respective surface were placed in a 5 mL blood tube. Approximately 4 mL of the calcified PRP was added to each tube and incubated (37° C., 90 min) with mild rocking (25 rpm). Following the incubation, the tubes were infinitely diluted with normal saline. The degree of platelet adhesion was determined using the lactate dehydrogenase (LDH) released when the adherent platelets were lysed with a Triton-PBS buffer using a Roche Cytotoxicity Detection Kit (LDH). The silicone disks were then incubated in 1 mL of Triton-PBS buffer. After 25 min, 100 μL was transferred to a 96-well plate and combined with 100 μL of the LDH reagent buffer per the supplier specifications. The absorbance of each well (duplicates of n=6) was then measured using a 96-well plate reader (Biotek), and the number of platelets adhered was determined using the calibration curve.

Results and Discussion

To take advantage of the antimicrobial and platelet activation prevention properties of nitric oxide (NO), NO-donors (e.g. s-nitrosothiols or diazeniumdiolates) have been developed to provide storage and localized delivery of NO. Such NO-donors are adaptable for incorporation into polymeric materials typically used for medical devices, such as polyurethanes, silicones, or polyvinyl chloride.[26, 27] The addition of these donors at various levels also provides the ability to control the level of NO that is delivered from the materials.[28] NO-releasing materials have been used for reducing thrombus formation and bacterial growth during catheterization. However, once all or most of the NO has been released, the antibacterial properties of the materials are significantly diminished. Thus, the present example provides examples of coatings and coated surfaces that provide both passive and active mechanisms of inhibiting thrombosis, bacterial growth, and surface fouling.

The present example demonstrates the ability of a material to not only offer an increase in steric ability to prevent bacterial and protein adhesion through a passive mechanism but also utilize the active biocidal mechanism of NO. In addition to combining these mechanisms, the antifouling capability of the material is retained after all NO has been released from the surface, making it attractive for long term applications. Specifically, this is done by the immobilization of the NO-donor precursor N-acetyl-D-penicillamine (NAP) to silicone surfaces using an alkylamine spacer (FIG. 16). As shown in FIG. 16, increasing the grafting density of free amines was done through branching of the initial spacer (steps E, F, I, J of FIG. 16) Following immobilization of the NO-donor precursor (steps C, G, K of FIG. 16), the grafted donor is nitrosated to its NO-rich form S-nitroso-N-acetyl-D-penicillamine (SNAP) (steps, D, H, L of FIG. 16).

Figure 17:
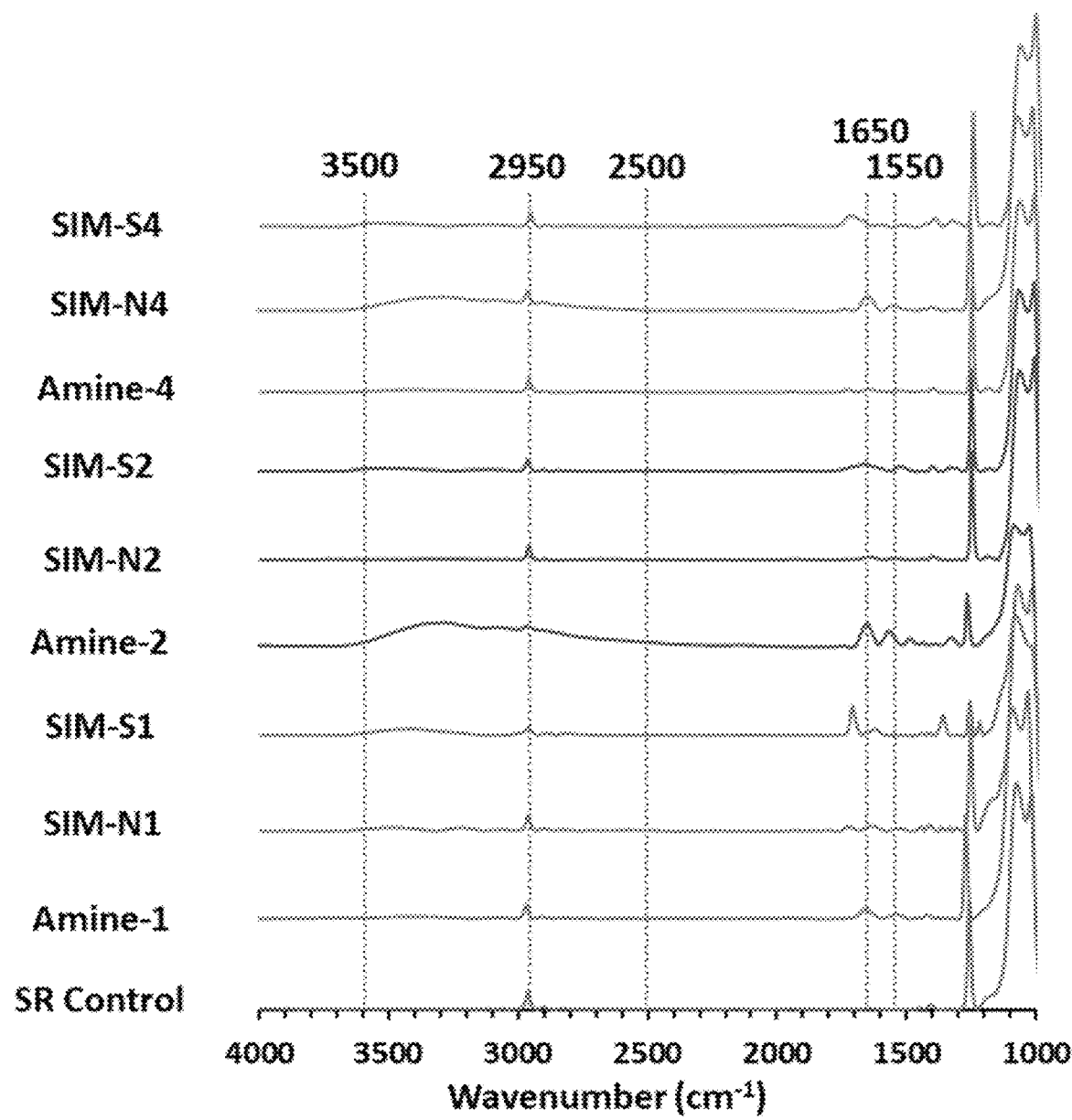
FIG. 17 shows FTIR spectra for different samples. Amine-1, Amine-2 and Amine-4 correspond to amine functionalized surfaces with unbranched and branched surfaces. 3500-2500 represents unreacted —COOH groups present after amine-functionalization for SIM-N4 and Amine-2. 2950 represents alkyl groups present in abundance in SR and aminated surfaces of SR. Double peaks of 1650, 1550 represent primary amine groups in Amine-1, Amine-2 and Amine-4. 1650 represents saturated amide groups in SIM-N1, SIM-N2, SIM-N4, SIM-S1, SIM-S2 and SIM-S4. 1550 in SIM-S2 represents nitroso group of the NO-donor attached.
Figure 18:
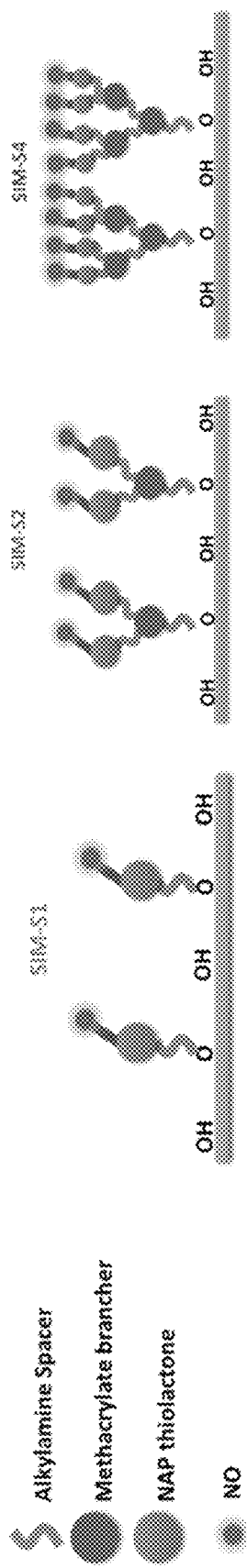
FIG. 18 shows an illustration of embodiments of unbranched (SIM-S1) and branched (SIM-S2 and SIM-S4) surface immobilized NO-donor surfaces of the present disclosure.

SIM-N1 and SIM-S1 correspond to unbranched polymers that are non-nitrosated (product of C on FIG. 16) and nitrosated (product of D on FIG. 16), respectively. SIM-N2 and SIM-S2 correspond to branched polymers that are non-nitrosated (product of G on FIG. 16) and nitrosated (product of H on FIG. 16), respectively. Finally, SIM-N4 and SIM-S4 correspond to branched polymers that are non-nitrosated (product of K on FIG. 16) and nitrosated (product of L on FIG. 16), respectively. FIG. 18 provides a schematic illustration of the branched (SIM-S2 and SIM-S4) and unbranched (SIM-S1) functionalized surfaces. In the present example, these materials will be referred to as abbreviated above for all the experiments, in addition to the bare silicone surface which will be considered as the control. To ensure covalent bonding of the surface modifications, FTIR measurements were carried out (FIG. 17). Since nitrogen atoms overlap in terms of FTIR peaks, appearance and disappearance of amide and primary amines was seen as the reaction steps were completed. This was followed by measurement of water contact angle to check for any significant differences in hydrophilicity of the functionalized surface. It is interesting to note here that hydrophilicity of the surfaces increased with increased NO-release (discussed in greater detail below). This could be attributed to lower availability of amine functionalized surfaces as the reaction is more complete.

TABLE 8 shows the ability of various surface modified SR substrates to reduce nonspecific protein adsorption over 2 h.

| | SR | SIM-N1 | SIM-S1 | SIM-N2 | SIM-S2 |
|---|---|---|---|---|---|
| Fg Adsorption ($\mu g\ cm^{-2}$) | 72.4 ± 16.4 | 74.5 ± 13.7 | 51.0 ± 15.5 | 33.0 ± 11.0 | 24.7 ± 3.2 |
| Reduction (%) | — | — | 29.6 ± 26.7 | 54.4 ± 18.3 | 65.8 ± 8.9 |
| p value vs control | — | NS | 0.024 | $1.94 \times 10^{-4}$ | $6.59 \times 10^{-4}$ |
| p value vs SIM-S2 | $6.59 \times 10^{-5}$ | $1.43 \times 10^{-5}$ | 0.027 | NS | — |

As seen in the design strategy, the NO-load and release capacity of the materials was varied by branching of the initial alkyl spacer to increase the number of free amines. This variation in NO-load and release capacity was measured by using a chemiluminescence nitric oxide analyzer (NOA). NOA is the gold standard for measurement of NO flux from materials and is a very efficient and sensitive instrument that can analyze NO release down to 1/10th of ppb.[29] To ensure NO release was only from the surface functionalization and not from the bulk material due to possible swelling of the diamine group during the reaction period, control measurements were done on samples using the same reaction scheme without immobilization of the aminosilane.

Figure 19A:
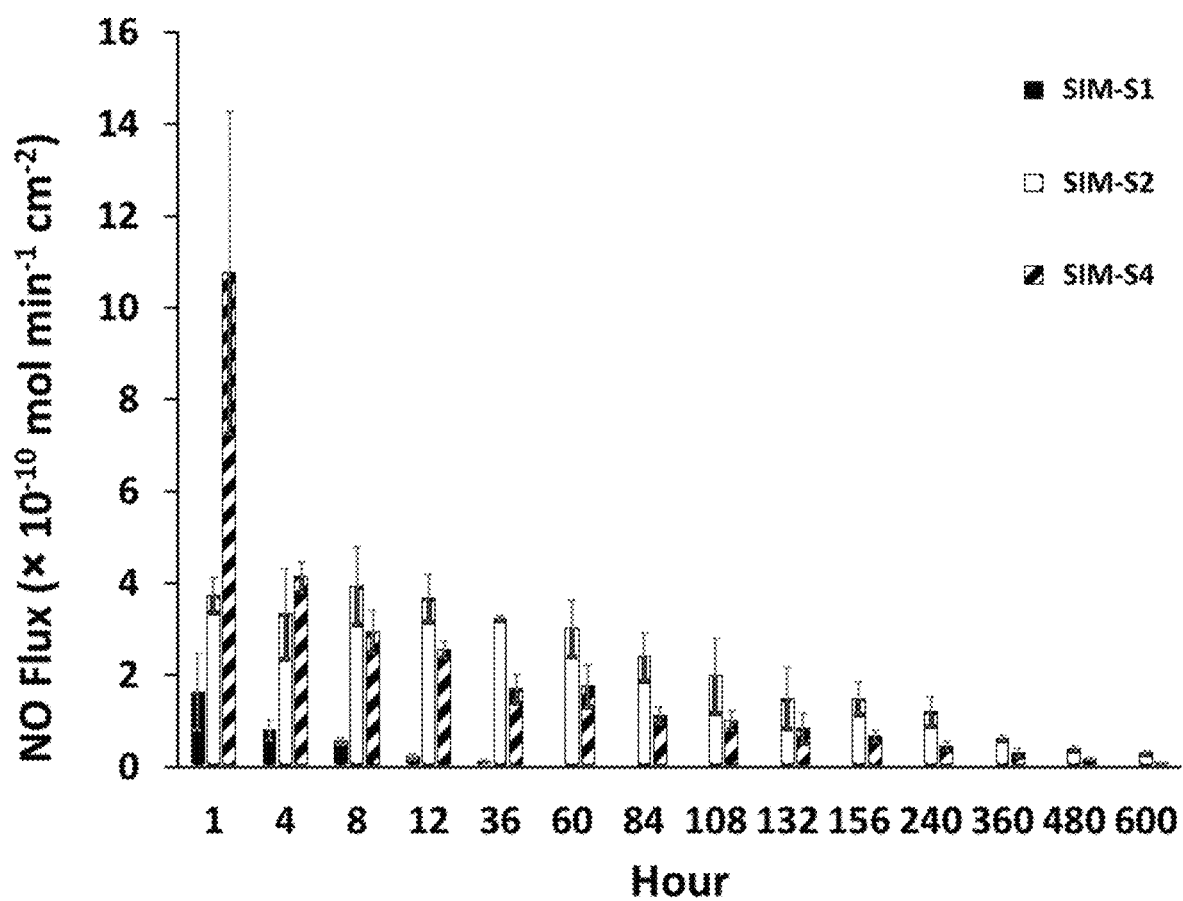
FIGS. 19A-19B show (FIG. 19A) day by day NO release measurements for 600 h/25 d and (FIG. 19B) Cumulative NO release over 600 h/25 d.
Figure 19B:
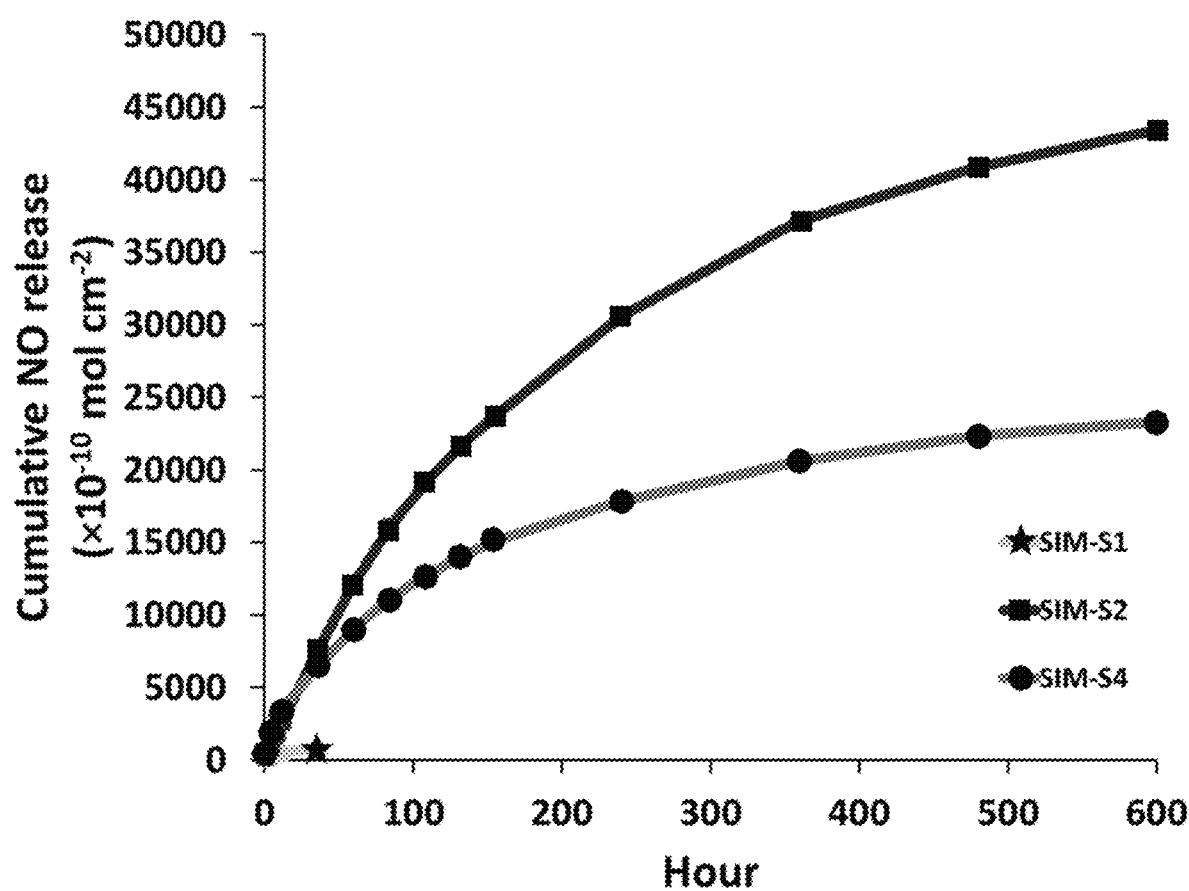

One of the theoretical expectations of this study was to see increasing NO-load and release measurements with an increase in branching. However, as demonstrated in FIGS. 19A-19B, NO release measurements were significantly higher for SIM-S2 (cumulative release: $43442.53 \times 10_{-10}$ mol $cm_{-2}$) when compared to SIM-S4 (cumulative release: $23319.98 \times 10_{-10}$ mol $cm_{-2}$) (FIG. 19B, Table 7) over the 25-d period. There could be two possible explanations for this: steric hindrance in case of higher branching and hence NAP thiolactone was not able to completely bind to the amine groups, and/or more branching increased the probability of chain interactions within the polymer before the free amine groups could react with NAP thiolactone. Therefore, it could be concluded that branching increasingly doesn't necessarily keep increasing the NO-load or release. This study also demonstrates the design of a surface that can release NO up to 25 days at endogenous flux levels. This increasing branching method is a technique to increase NO release characteristics, much like the function of metal ions when added to NO releasing polymers. However, beyond the increased NO release properties, this material proved to offer additional advantages as it also imparts antifouling characteristics to the material, as demonstrated by the data described below.

TABLE 5

Contact angle measurements compared between all NAP-thiolactone and nitroso group functionalized surfaces.

| Material | Static Water Contact Angle (°) |
|---|---|
| SR | 106.77 ± 3.36 |
| SIM-N1 | 94.36 ± 3.36 |
| SIM-S1 | 101.56 ± 4.48 |
| SIM-N2 | 64.95 ± 11.87 |
| SIM-S2 | 53.78 ± 5.23 |
| SIM-N4 | 93.09 ± 2.91 |
| SIM-S4 | 90.90 ± 7.97 | drastic improvements in the overall hemocompatibility and antibacterial nature of these materials.[30]

Figure 20:
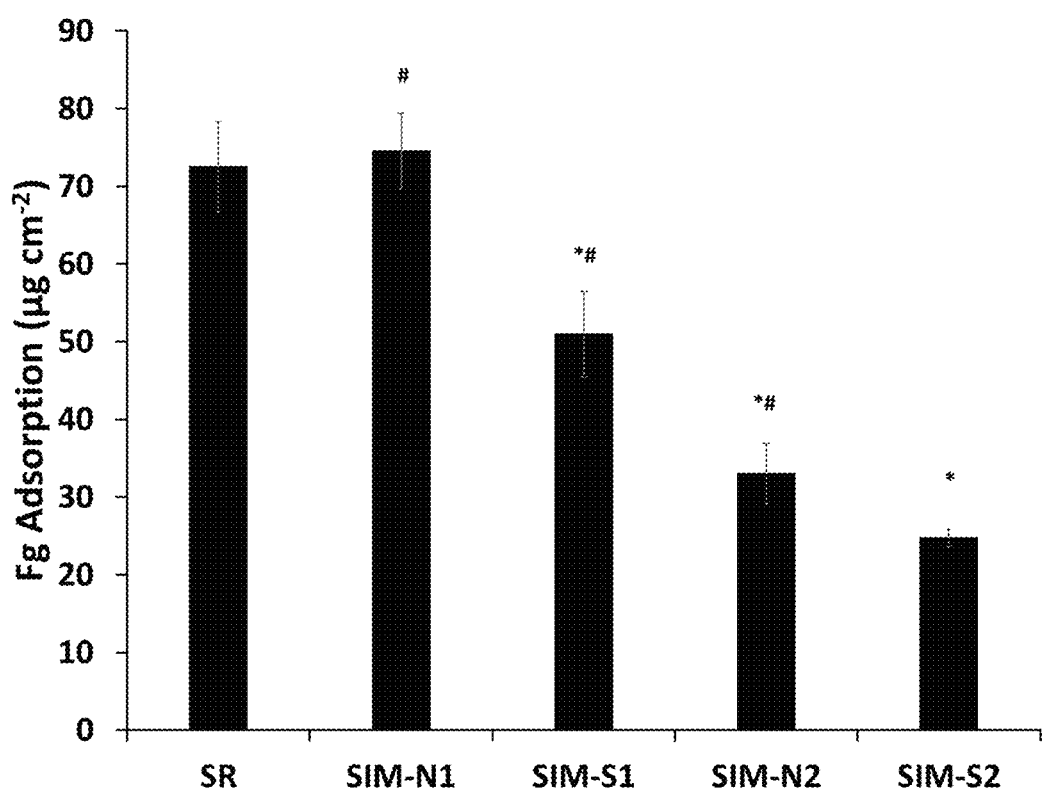
FIG. 20 shows adsorption of fibrinogen to modified SR surfaces over a 2 h period. Values are expressed as mean±standard error. Measurements were conducted using n=8 per group. *—significantly different compared to unmodified SR. #—significantly different compared to SIMS-2 configuration.

To examine if the surface immobilized NO-donors (both nitrosated and non-nitrosated) can provide a decrease in protein adhesion observed on NO-releasing materials, 2 h exposure to FITC-labeled fibrinogen (2 mg $mL^{-1}$) was conducted at 37° C. (Table 8 and FIG. 20). While minimal changes in contact angle were observed, increasing the branched nature of the surface grafted NAP groups between SIM-N1 and SIM-N2 decreased the degree of Fg adsorption, and is believed to result from increases in steric hindrance.[29] However, altering the chemistry of the linkages to the amine functionalized surface further increases the non-fouling ability of these materials. Overall, reductions in protein adsorption were observed to reach 65.8±8.9% for SIM-S2 when compared to the unmodified SR. It is also interesting to note that the release of NO from the surface had no significant effect on the amount of adsorbed Fg.

Figure 21:
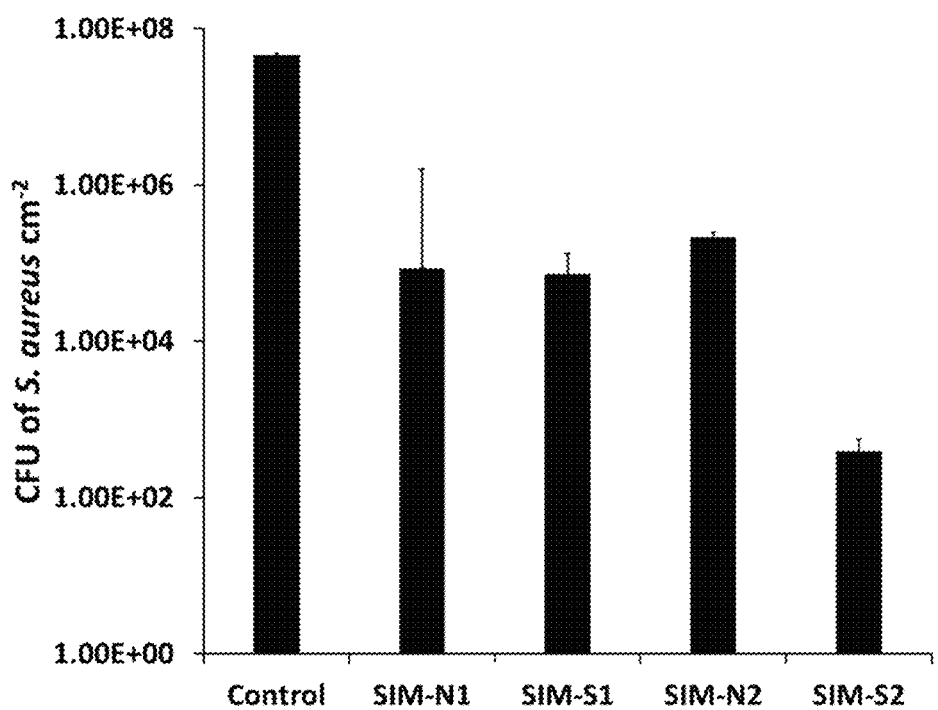
FIG. 21 shows that SIM-S2 was able to reduce bacteria adhesion by ~2.5 logs when compared to control samples.

Bacterial adhesion, which ultimately results in biofilm formation, is a predominant issue in implanted devices aided by the moist and microbiome sustaining milieu. Coupled with fouling proteins, implants can become hosts to several pathogens that ultimately lead to medical device failure, infection (including bloodstream infection) and sometimes death.[8] Antimicrobial efficacy of the designed non-fouling antimicrobial coating material was compared to the SR control samples (Table 9 and FIG. 21) to confirm their

TABLE 6

NO Flux release measurements for SIM-S1, SIM-S2, and SIM-S4 up to 600 h.

| NO Flux ($\times 10^{-10}$ mol $min^{-1}$ $cm^{-2}$) | 1 h | 4 h | 8 h | 12 h | 36 h | 60 h | 84 h | 108 h | 132 h | 156 h | 240 h | 360 h | 480 h | 600 h |
|---|---|---|---|---|---|---|---|---|---|---|---|---|---|---|
| SIM-S1 | 1.633 ± .835 | 0.795 ± .228 | 0.566 ± .076 | 0.216 ± .060 | 0.108 ± .035 | | | | | | | | | |
| SIM-S2 | 3.733 ± .375 | 3.335 ± .986 | 3.935 ± .849 | 3.677 ± .515 | 3.228 ± .053 | 3.013 ± .614 | 2.391 ± .524 | 1.976± .822 | 1.493 ± .659 | 1.496 ± .349 | 1.203 ± .331 | .626 ± .060 | 0.404 ± .049 | 0.305 ± .032 |
| SIM-S4 | 10.753 ± 3.509 | 4.126 ± .338 | 2.946± .466 | 2.547 ± .186 | 1.706 ± .317 | 1.763 ± .449 | 1.122 ± .180 | 1.012 ± .204 | 0.836 ± .324 | 0.673 ± .132 | 0.441 ± .096 | 0.316 ± .090 | 0.174 ± .027 | 0.085 ± .008 |

TABLE 7

Cumulative NO release measurements for SIM-S1, SIM-S2, and SIM-S4 up to 600 h.

| Cumulative NO Release ($\times 10^{-10}$ mol $cm^{-2}$) | 1 h | 4 h | 8 h | 12 h | 36 h | 60 h | 84 h | 108 h | 132 h | 156 h | 240 h | 360 h | 480 h | 600 h |
|---|---|---|---|---|---|---|---|---|---|---|---|---|---|---|
| SIM-S1 | 98 | 316 | 479 | 573 | 807 | | | | | | | | | |
| SIM-S2 | 223 | 860 | 1732 | 2645 | 7617 | 12110 | 16002 | 13147 | 21645 | 23798 | 30599 | 37183 | 40889 | 43442 |
| SIM-S4 | 645 | 1984 | 2833 | 3452 | 6554 | 9052 | 11129 | 12666 | 13997 | 15084 | 17894 | 20621 | 22386 | 23320 |

One common method for assessing the fouling of materials in vitro is to examine the ability of the material to resist non-specific protein adhesion. If intended for blood contacting applications, more specifically, fibrinogen (Fg) adhesion can be assessed. The adsorption of Fg to the material surface greatly increases the ability for activated platelets or bacteria to bind to the surface, leading to higher risks of thrombus formation or infection.[6] While the orientation of Fg adsorption has been shown to determine the degree of platelet adhesion, limiting protein adhesion regardless of orientation is generally considered to be an improvement in the hemocompatibility of a material.[7] Developing NO-releasing materials that can reduce protein adsorption could provide superior bacterial repulsion properties. The samples were incubated in bacterial solutions containing ~$10^7$-$10^8$ CFU $mL^{-1}$ of S. aureus, which is one of the most commonly found nosocomial infection bacteria.[30, 31] These infections are most commonly associated with catheters, stents and prosthetic devices among other implants. As mentioned above, it was believed that the NO molecules would actively kill bacteria, while the immobilized structure would passively repel proteins and enhance the biocompatibility of the material even after all the NO load was exhausted. The antimicrobial efficacy of the designed test samples was clearly observed after 24 h of incubation, the crucial time for initiation of bacterial infection. The CFU $cm^{-2}$ of S. aureus adhered to each material is shown on Table 9. While the non-nitrosated surfaces (SIM-N1 and SIM-N2) demonstrated some reduction in bacterial activity over the control, SIM-S2 showed the highest bactericidal efficiency with a reduction of 99.91±0.06% (FIG. 21) when compared to the SR samples where a growth of ~$10_8$ CFU $cm_{-2}$ was observed. This reduction is higher compared to samples with only NAP thiolactone functionalization (SIM-N1=82.14±22.20% and SIM-N2=96.86±0.49%) and SIM-S1 (85.71±24.74%). It can also be concluded from the results that NAP thiolactone functionalized surfaces (SIM-N1 and SIM-N2) alone could only reduce bacterial adhesion because they cannot kill bacteria as it does not have any bactericidal property. The surfaces functionalized with NO releasing property reduce adhesion through passive mechanisms as well as having active antibacterial activity, thus producing a synergistic effect which enhances the antimicrobial efficacy. In summary, the synergistic effect of the modifiable NO-release kinetics from the SR surface and prevention of protein and bacterial adhesion due to the surface immobilized structures can help significantly reduce undesired clinical consequences of a medical implantation.

($p=0.001$). It is believed that this may stem from the chemical structure of the methacrylate and diamine linkages. Variation of the composition of these to provide a more hydrophilic surface (such as using an amine-terminated polyethylene-glycol silane, or the presence/addition of hydroxyl or carboxylic acid side chains) may possibly allow for further reduction in protein adhesion as the degree of polymerization at the surface increases. The addition of these side chains may also provide alternative chemistries for branching. Other non- limiting options may include diethylenetriamine in place of the purely alkane backbone of ethylenediamine. While the SIM-S2 configuration did not provide significant reductions in platelet adhesion when compared to SIM-N1 or SIM-S1, the significant increase in NO release can provide increased bactericidal activity for extended durations.

TABLE 9 shows the ability of various surfaces to decrease bacterial adhesion over 24 h.

| | SR | SIM-N1 | SIM-S1 | SIM-N2 | SIM-S2 |
|---|---|---|---|---|---|
| Average CFU of *S. aureus* $cm^{-2}$ | $4.63 \times 10^7$ | $8.58 \times 10^4$ | $7.15 \times 10^4$ | $2.14 \times 10^5$ | $3.89 \times 10^2$ |
| Reduction (%) | — | 82.14 ± 22.20 | 85.71 ± 24.74 | 96.86 ± 0.49 | 99.99 ± .002 |

Figure 22:
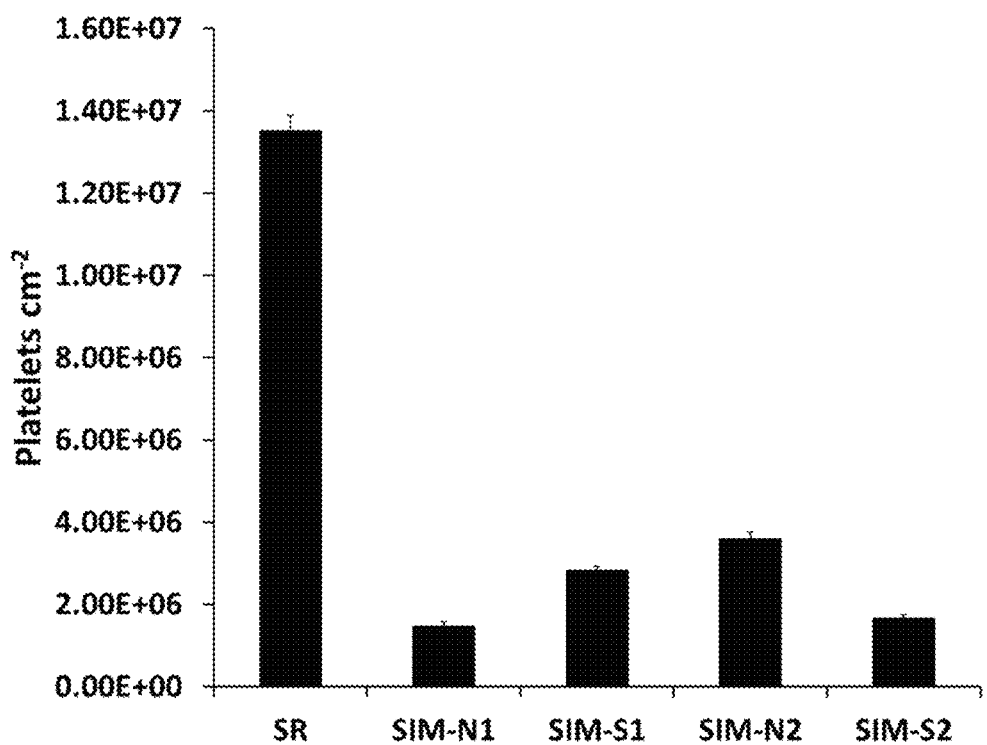
FIG. 22 show platelets adsorbed per surface area over a period of 90 mins.

Platelet activation and adhesion are important considerations when determining the hemocompatibility of materials. Upon activation, platelets release several coagulation agonists such as phospholipase $A_2$ (which is then converted into thromboxane $A_2$), furthering platelet activation and the coagulation cascade and increasing thrombin generation.[32] One key predecessor of platelet activation is the adsorption of fibrinogen to the materials surface, where changes in the protein confirmation allows for binding to the platelets Gp IIb/IIIa receptors. Therefore, reducing protein adhesion alone can act as a mechanism to reduce platelet activation. Thus, it was demonstrated that while NO releasing materials have been shown to significantly reduce platelet adhesion, the functionality of the modified surface is not lost after all the loaded NO has been released. In fact, small molecules with free thiol groups (similar to NAP) have been shown to provide potent thrombolytic effects when administered systemically by binding to von Willebrand factor crosslinks of adhered platelets in arterial thrombi.[33] Both nitrosated and non-nitrosated surfaces were incubated in porcine platelet rich plasma for 90 min, where platelet adhesion was then determined using a lactate dehydrogenase (LDH) assay. The degree of platelet adhesion for all materials is shown in FIG. 22. Each variation of the surface modifications was able to provide significant reductions in platelet adhesion when compared to unmodified SR controls (Table 10). The SIM-N1 and SIM-S2 modifications provided the highest reductions, but were not statistically significant when compared to each other (p value>0.5). However, as the branching increased from the SIM-N1 to the SIM-N2 configuration, the ability to prevent adhesion appeared to decrease

TABLE 10 shows the ability of various surfaces to reduce the platelets adsorbed per surface area over a period of 90 mins.

| | SR | SIM-N1 | SIM-S1 | SIM-N2 | SIM-S2 |
|---|---|---|---|---|---|
| Platelets $cm^{-2}$ ($\times 10^6$) | 13.5 ± 0.4 | 1.5 ± 0.1 | 2.8 ± 0.1 | 3.6 ± 0.2 | 1.6 ± 0.1 |
| Reduction (%) | — | 89.1 ± 0.9 0.1 | 79.1 ± 1.0 1.7 | 73.4 ± 1.3 0.5 | 87.7 ± 0.7 0.2 |

In summary, the present example describes embodiments of the present disclosure to attach various amounts of the nitric oxide releasing donor, SNAP to any polymer material to provide both bactericidal/antiplatelet activity while simultaneously providing a non-fouling nature to the material surface. This method will be highly applicable for biomedical device materials that are prone to infections and thrombosis related failures, and can easily be coupled with other existing NO-releasing polymers.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

References for Example 4

1. B. D. Ratner, *Biomaterials*, 2007, 28, 5144-5147.
2. E. J. Brisbois, R. P. Davis, A. M. Jones, et al., *Journal of Materials Chemistry B*, 2015.
3. R. E. Cronin and R. F. Reilly, 2010.

4. N. Høiby, O. Ciofu, H. K. Johansen, et al., *International journal of oral science*, 2011, 3, 55.
5. P. Singha, J. Pant, M. J. Goudie, et al., *Biomaterials Science*, 2017, DOI: 10.1039/C6BM00948D.
6. G. W. Charville, E. M. Hetrick, C. B. Geer, et al., *Biomaterials*, 2008, 29, 4039-4044.
7. B. Sivaraman and R. A. Latour, *Biomaterials*, 2010, 31, 832-839.
8. P. Singha, J. Locklin and H. Handa, *Acta Biomaterialia*, 2017, 50, 20-40.
9. L.-C. Xu and C. A. Siedlecki, *Biomaterials*, 2007, 28, 3273-3283.
10. X. Hou, X. Wang, Q. Zhu, et al., *Colloids and Surfaces B: Biointerfaces*, 2010, 80, 247-250.
11. E. Ueda and P. A. Levkin, *Advanced healthcare materials*, 2013, 2, 1425-1429.
12. L. C. Xu and C. A. Siedlecki, *Journal of Biomedical Materials Research Part B: Applied Biomaterials*, 2017, 105, 668-678.
13. E. J. Falde, S. T. Yohe, Y. L. Colson, et al., *Biomaterials*, 2016, 104, 87-103.
14. N. MacCallum, C. Howell, P. Kim, et al., *ACS Biomaterials Science & Engineering*, 2014, 1, 43-51.
15. D. C. Leslie, A. Waterhouse, J. B. Berthet, et al., *Nature biotechnology*, 2014, 32, 1134-1140.
16. N. A. Alcantar, E. S. Aydil and J. N. Israelachvili, *Journal of biomedical materials research*, 2000, 51, 343-351.
17. K. Holmberg, K. Bergstrom and M.-B. Stark, in *Poly (Ethylene Glycol) Chemistry*, Springer, 1992, pp. 303-324.
18. C.-G. Gölander, J. N. Herron, K. Lim, et al., in *Poly (ethylene glycol) Chemistry*, Springer, 1992, pp. 221-245.
19. J. H. Lee, H. B. Lee and J. D. Andrade, *Progress in Polymer Science*, 1995, 20, 1043-1079.
20. J. Andrade, V. Hlady and S.-I. Jeon, *Polymeric Materials: Science and Engineering*, 1993, 60-61.
21. J. M. Harris, *Poly (ethylene glycol) chemistry: biotechnical and biomedical applications*, Springer Science & Business Media, 1992.
22. E. J. Brisbois, H. Handa and M. E. Meyerhoff, in *Advanced Polymers in Medicine*, Springer, 2015, pp. 481-511.
23. T. Kolobow, E. Stool, P. Weathersby, et al., *Transactions—American Society for Artificial Internal Organs*, 1974, 20, 269.
24. H. A. Moynihan and S. M. Roberts, *Journal of the Chemical Society, Perkin Transactions 1*, 1994, 797-805.
25. Z. Paryzek and I. Skiera, *Organic preparations and procedures international*, 2007, 39, 203-296.
26. M. J. Goudie, E. J. Brisbois, J. Pant, et al., *International Journal of Polymeric Materials and Polymeric Biomaterials*, 2016, 65, 769-778.
27. E. J. Brisbois, T. C. Major, M. J. Goudie, et al., *Acta Biomaterialia*, 2016, 44, 304-312.
28. M. W. Vaughn, L. Kuo and J. C. Liao, *American Journal of Physiology—Heart and Circulatory Physiology*, 1998, 274, H2163-H2176.
29. E. J. Brisbois, H. Handa and M. E. Meyerhoff, in *Advanced Polymers in Medicine*, ed. F. Puoci, Springer International Publishing Switzerland, Switzerland, 2015.
30. Q. Liu, P. Singha, H. Handa, et al., *Langmuir*, 2017, DOI: 10.1021/acs.langmuir.7b02970.
31. S. Y. Tong, J. S. Davis, E. Eichenberger, et al., *Clinical microbiology reviews*, 2015, 28, 603-661.
32. J. J. Ferguson, R. A. Harrington and N. A. Chronos, *Antiplatelet Therapy in Clinical Practice*, Taylor & Francis, 1999.
33. S. M. de Lizarrondo, C. Gakuba, B. A. Herbig, et al., *Circulation*, 2017, CIRCULATIONAHA. 117.027290.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:
1. A method of coating a substrate, comprising:
exposing at least one surface of a NO-donor substrate to a polymer, wherein the polymer has a structure according to the following formula:

where each occurrence of Z is a zwitterionic moiety;
where, in each instance, either (i) $A^1$ is none and $A^2$ is $=$O or (ii) $A^1$ is a covalent bond to the at least one surface of the substrate and $A^2$ is —OH;
where each occurrence of $R^1$ is independently a covalent bond or a linear or branched, substituted or unsubstituted alkyl diradical having from 1 to 12 carbon atoms;
where each occurrence of $R^2$, $R^3$, and $R^4$ is independently a linear or branched, substituted or unsubstituted alkyl having from 1 to 12 carbon atoms; and
where a, b, and c are real number such that $0<a<1$, $0\leq b<1$, $0<c<1$, and $a+b+c=1$, and exposing the polymer to light energy, thereby causing the polymer to covalently attach to the at least one surface of the NO-donor substrate to form the coating on the NO-donor substrate.

2. The method of claim 1, wherein the light energy is ultraviolet light.

3. The method of claim 1, wherein the polymer is selected from one or more of the following:

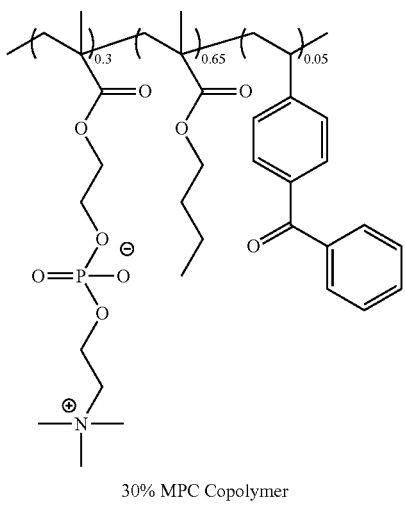

30% MPC Copolymer

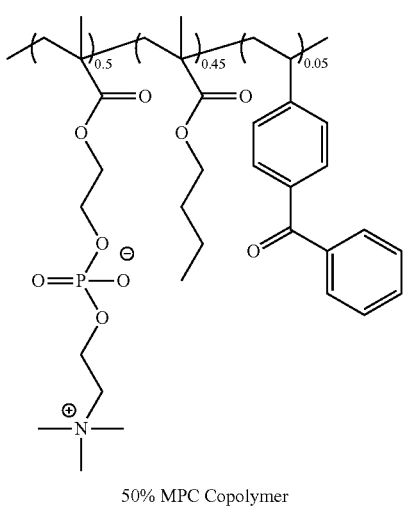

50% MPC Copolymer

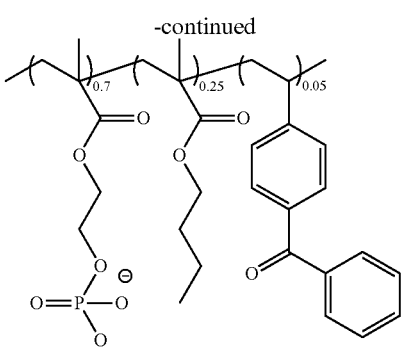

70% MPC Copolymer

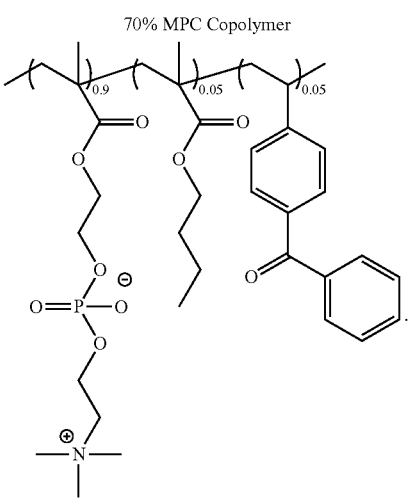

90% MPC Copolymer

4. The method of claim 1, wherein the NO-donor substrate comprises: an organic nitrate, a metal-NO complex, an N-nitrosamine, a S-nitrosothiol, or a combination thereof.

5. The method of claim 1, wherein the NO-donor substrate comprises a polymer doped with S-nitroso-N-acetylpenicillamine.

6. The method of claim 5, wherein polymer doped with S-nitroso-N-acetylpenicillamine includes about 6% to about 11% wt S-nitroso-N-acetylpenicillamine.

7. The method of claim 1, further comprising coating the NO-donor substrate in at least one layer of polymer film prior to combining the NO-donor substrate with the photo cross-linkable moiety.

* * * * *